(12) United States Patent
Yang-Woytowitz et al.

(10) Patent No.: US 10,767,146 B2
(45) Date of Patent: Sep. 8, 2020

(54) BLOOD CULTURE BOTTLES WITH MECHANISMS FOR CONTROLLED RELEASE OF SUBSTANCES INTO CULTURE MEDIA

(71) Applicant: Becton, Dickinson and Company, Franklin Lakes, NJ (US)

(72) Inventors: Mei Yang-Woytowitz, Baltimore, MD (US); Brent Pohl, Timonium, MD (US); Gary F. Hershner, Red Lion, PA (US); Eric Ursprung, Camp Hill, PA (US); Michael A. Brasch, Gaithersburg, MD (US); Ming-hsiung Yeh, New Freedom, PA (US); Patrick Shawn Beaty, Dallastown, PA (US); Charles C. Yu, Lutherville, MD (US); Timothy M. Wiles, Manchester, MD (US); Liping Feng, Baltimore, MD (US); Ben Turng, Tucson, AZ (US); Xiaofei Chang, Timonium, MD (US); Patrick R. Murray, Gibson Island, MD (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 15/031,958

(22) PCT Filed: Oct. 24, 2014

(86) PCT No.: PCT/US2014/062216
§ 371 (c)(1),
(2) Date: Apr. 25, 2016

(87) PCT Pub. No.: WO2015/061711
PCT Pub. Date: Apr. 30, 2015

(65) Prior Publication Data
US 2016/0265022 A1     Sep. 15, 2016

Related U.S. Application Data

(60) Provisional application No. 62/032,329, filed on Aug. 1, 2014, provisional application No. 61/895,760, filed on Oct. 25, 2013.

(51) Int. Cl.
*C12Q 1/02*     (2006.01)
*C12M 1/00*     (2006.01)
(Continued)

(52) U.S. Cl.
CPC ...... *C12C 1/02* (2013.01); *A61J 1/05* (2013.01); *A61J 1/1406* (2013.01); *A61J 1/1418* (2015.05);
(Continued)

(58) Field of Classification Search
CPC ......... C12Q 1/02; A61J 1/1418; A61J 1/2006; A61J 1/05; A61J 1/1406; A61J 1/2089;
(Continued)

(56) References Cited

U.S. PATENT DOCUMENTS 2,449,968 A    9/1948   Smith
3,932,222 A    1/1976   Dorn
(Continued)

FOREIGN PATENT DOCUMENTS

CN     103045466 A    4/2013
CN     103289988 A    9/2013
(Continued)

OTHER PUBLICATIONS

Chinese Office Action for Application No. 201480070070.2 dated Jan. 19, 2017.
(Continued)

*Primary Examiner* — Jill A Warden
*Assistant Examiner* — Jacqueline Brazin
(74) *Attorney, Agent, or Firm* — Botos Churchill IP Law LLP

(57) ABSTRACT

An apparatus and associated methods of use for a controlled combination of reagents is disclosed. The apparatus includes
(Continued)

a vessel 400, a vessel insert 220, and a cap element 200. The vessel 400 has a body portion 410 for receiving a biological sample. The vessel insert 220 receives at least one reagent therein. Preferably, the vessel insert 220 is received in a portion 420 of the vessel 400. The cap element 200 is attached to the vessel 400 to secure the vessel insert 220 in the vessel 400. During use, the vessel insert 220 is adapted to release its contents when the biological sample is introduced into the body portion 410 of the vessel 400 upon application of an intermixing force to the vessel insert 220. A variety of intermixing forces may be applied, depending upon the embodiment of the present invention and its associated methods of use.

17 Claims, 51 Drawing Sheets

(51) Int. Cl.
| | |
|---|---|
| *A61J 1/20* | (2006.01) |
| *C12M 1/24* | (2006.01) |
| *A61J 1/05* | (2006.01) |
| *A61J 1/14* | (2006.01) |
| *C12C 1/02* | (2006.01) |
| *B01L 3/00* | (2006.01) |

(52) U.S. Cl.
CPC ............ *A61J 1/2006* (2015.05); *A61J 1/2089* (2013.01); *A61J 1/2093* (2013.01); *B01L 3/502* (2013.01); *C12M 23/08* (2013.01); *C12M 23/38* (2013.01); *C12M 29/00* (2013.01); *B01L 2200/0621* (2013.01); *B01L 2200/16* (2013.01); *B01L 2300/044* (2013.01); *B01L 2300/047* (2013.01); *B01L 2300/087* (2013.01); *B01L 2300/0832* (2013.01); *G01N 2800/26* (2013.01)

(58) Field of Classification Search
CPC ....... A61J 1/2093; B01L 3/502; C12M 23/08; C12M 23/38; C12M 29/00
USPC ........................................................ 422/550
See application file for complete search history.

(56) References Cited

U.S. PATENT DOCUMENTS

| | | | |
|---|---|---|---|
| 4,134,512 A | 1/1979 | Nugent | |
| 4,279,863 A | 7/1981 | Friehler | |
| 4,410,630 A | 10/1983 | Zierdt | |
| 4,675,159 A | 6/1987 | Al-Sioufi | |
| 4,812,408 A * | 3/1989 | Hammann | C12M 23/08 215/276 |
| 5,024,237 A * | 6/1991 | Guirguis | A61B 5/150213 422/913 |
| 5,511,558 A * | 4/1996 | Shepard | B01L 3/50825 600/573 |
| 5,658,531 A | 8/1997 | Cope et al. | |
| 5,738,670 A | 4/1998 | Grippi | |
| 6,001,087 A | 12/1999 | Zurcher | |
| 6,821,785 B1 * | 11/2004 | Anraku | A61B 5/15003 422/410 |
| 2007/0087431 A1 | 4/2007 | Ching et al. | |
| 2008/0202950 A1 * | 8/2008 | Anderson | B65D 51/2842 206/219 |
| 2011/0174642 A1 * | 7/2011 | Coon | B65D 51/2835 206/222 |
| 2011/0243816 A1 | 10/2011 | Shimada | |
| 2015/0060389 A1 * | 3/2015 | Bolger | B65D 39/0052 215/355 |
| 2015/0231626 A1 * | 8/2015 | Shi | B01L 3/50 435/288.2 |
| 2016/0265022 A1 | 9/2016 | Yang-Woytowitz et al. | |

FOREIGN PATENT DOCUMENTS

| | | |
|---|---|---|
| CN | 204803311 U | 11/2015 |
| DE | 19519886 A1 | 5/1998 |
| EP | 0073551 A2 | 3/1983 |
| EP | 0728522 B1 | 1/2002 |
| EP | 0832690 B1 | 7/2003 |
| JP | H07-333216 A | 12/1995 |
| JP | H10-108856 A | 4/1998 |
| WO | 2007068094 A1 | 6/2007 |

OTHER PUBLICATIONS

International Search Report for Application No. PCT/US2014/062216 dated Feb. 4, 2015.
European Communication issued in corresponding EP Application No. 14854991.8 dated May 19, 2017.
Canadian Office Action dated Feb. 21, 2018 for CA Application No. 2,928,589.
Japanese Office Action issued in corresponding JP application No. 2016-526158 dated Jul. 31, 2018.

* cited by examiner

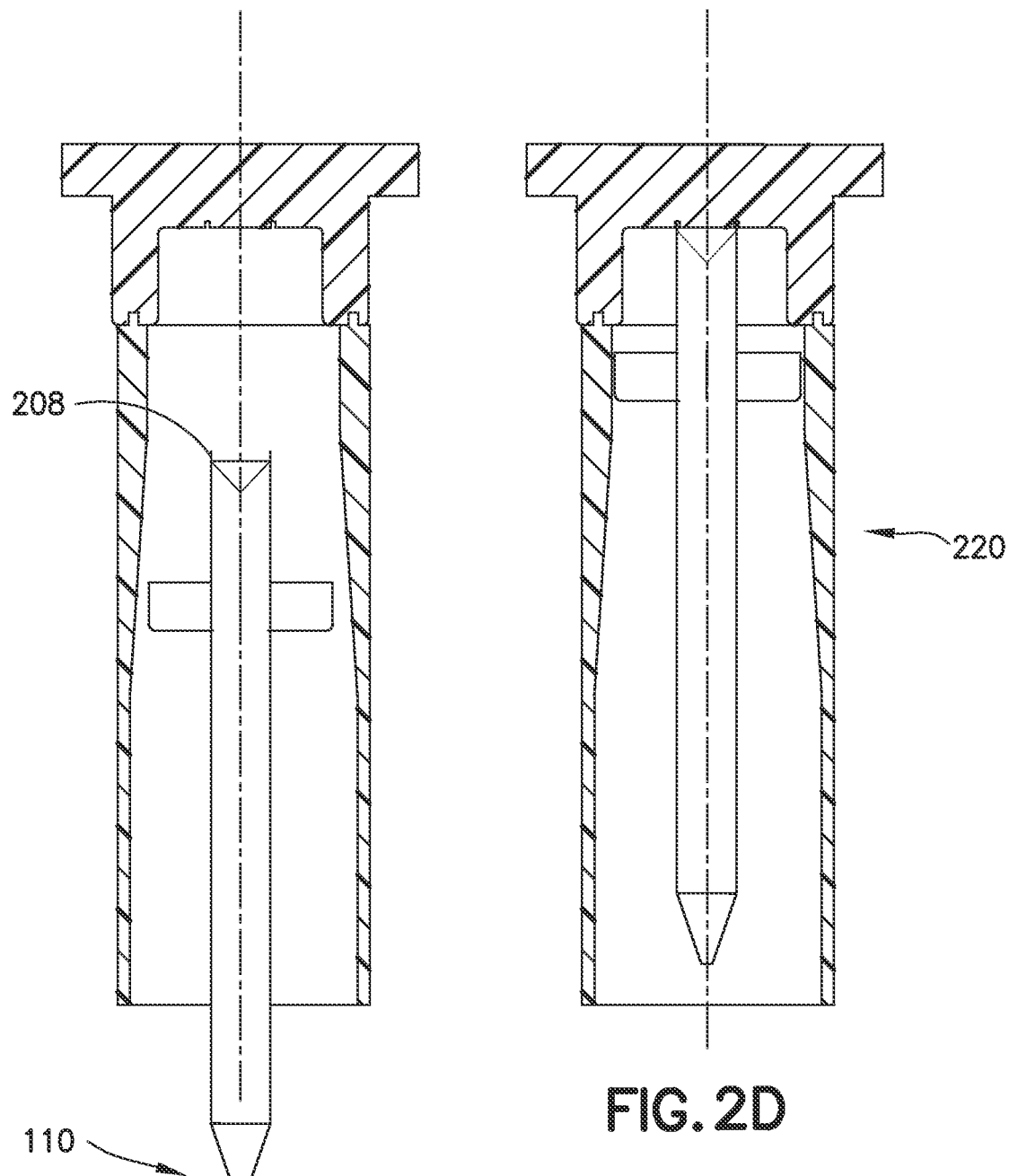

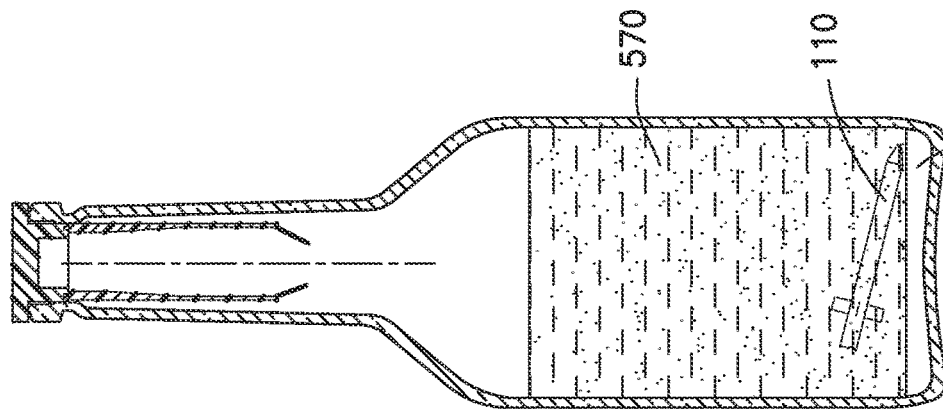
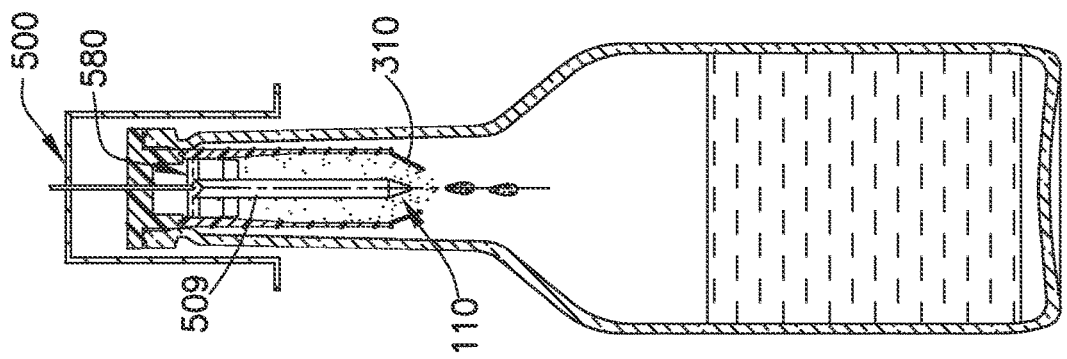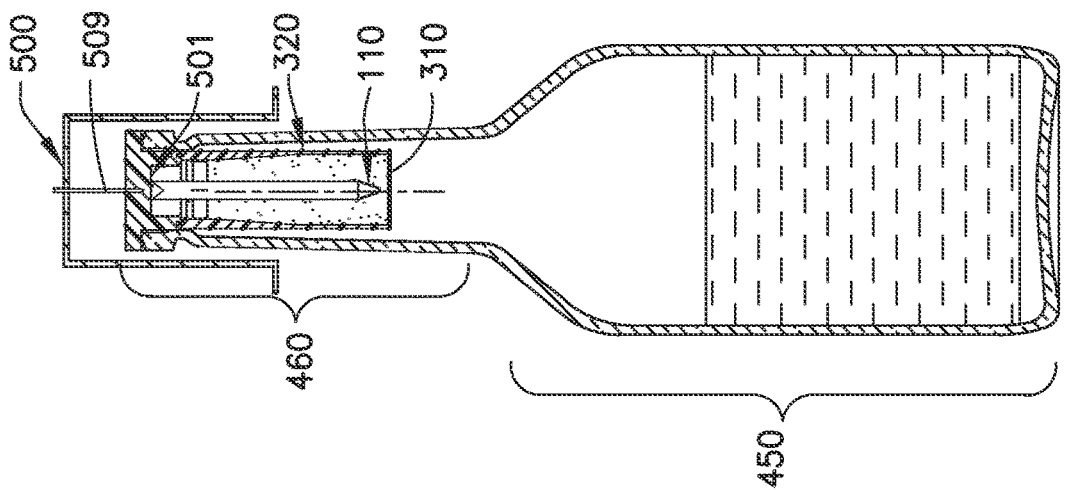

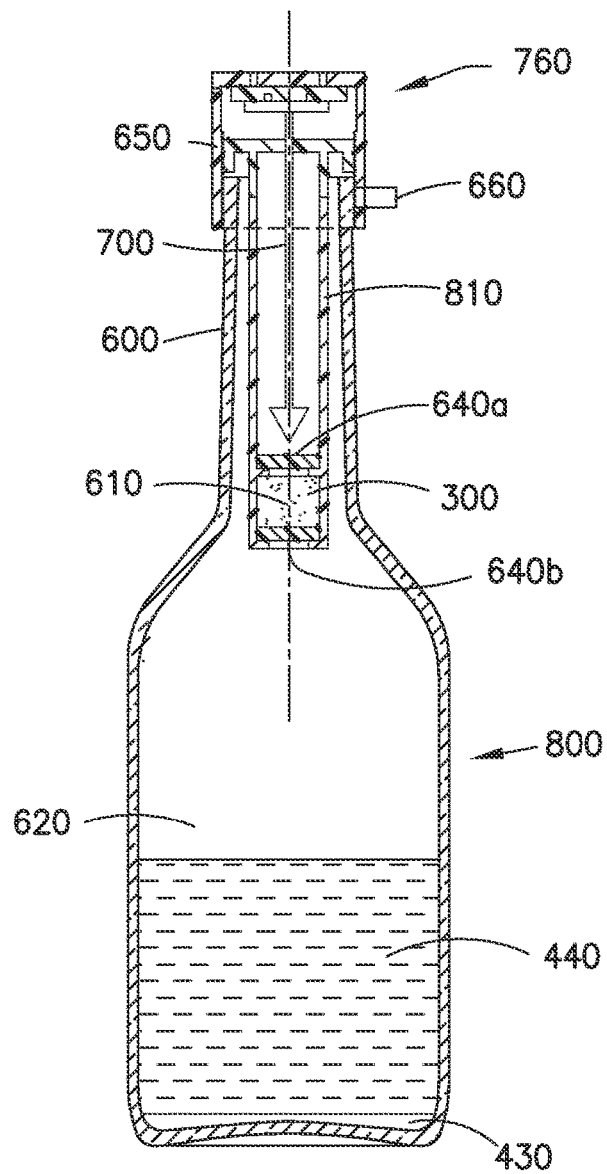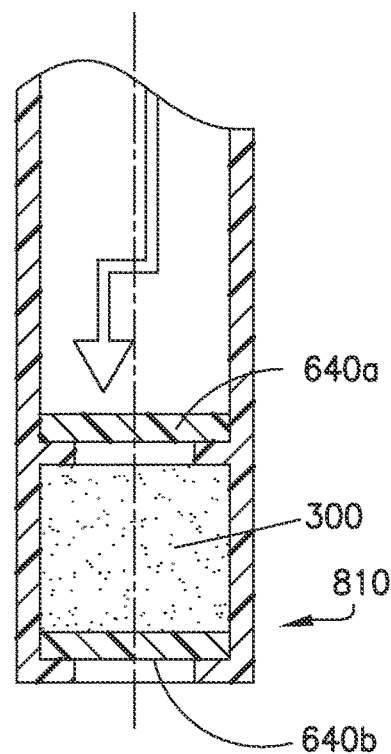
FIG.10A
FIG.10B

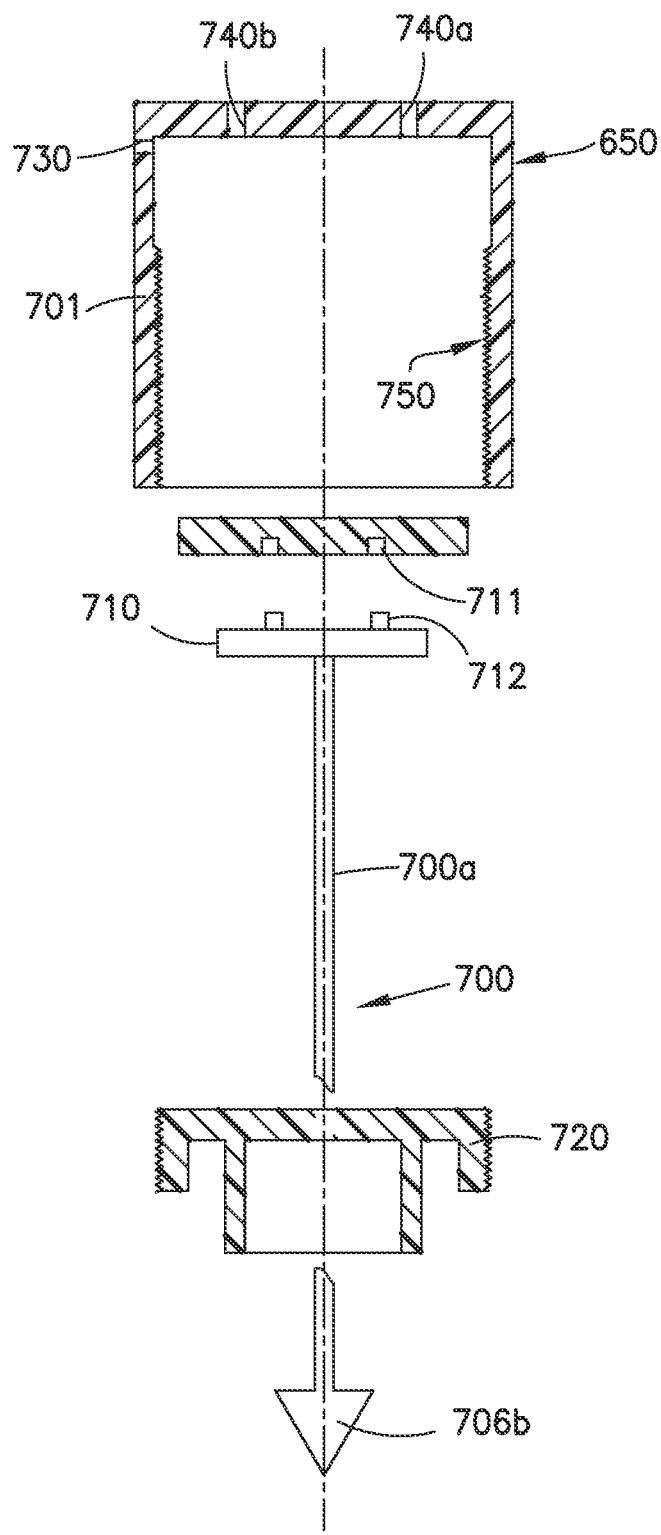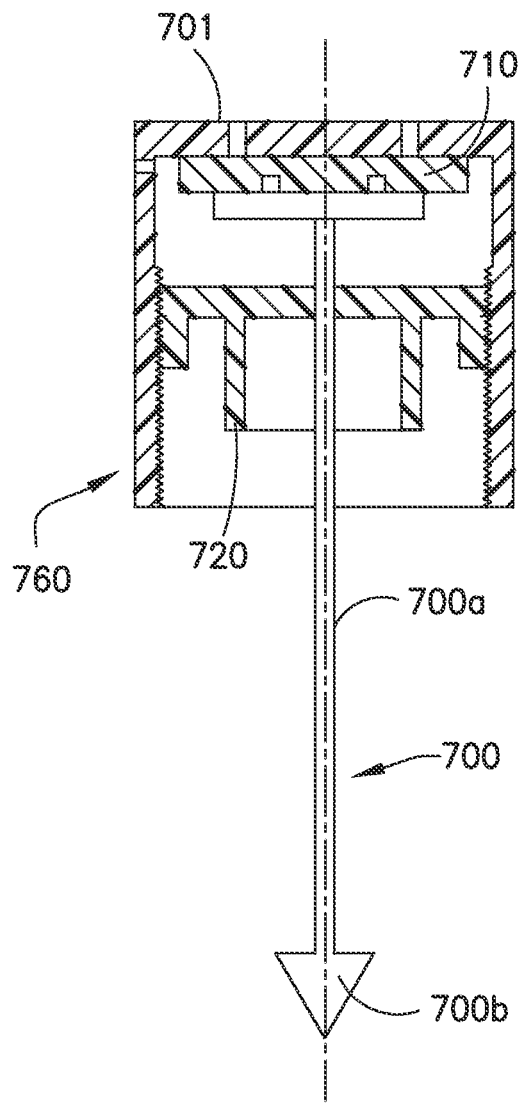
FIG.11A
FIG.11B

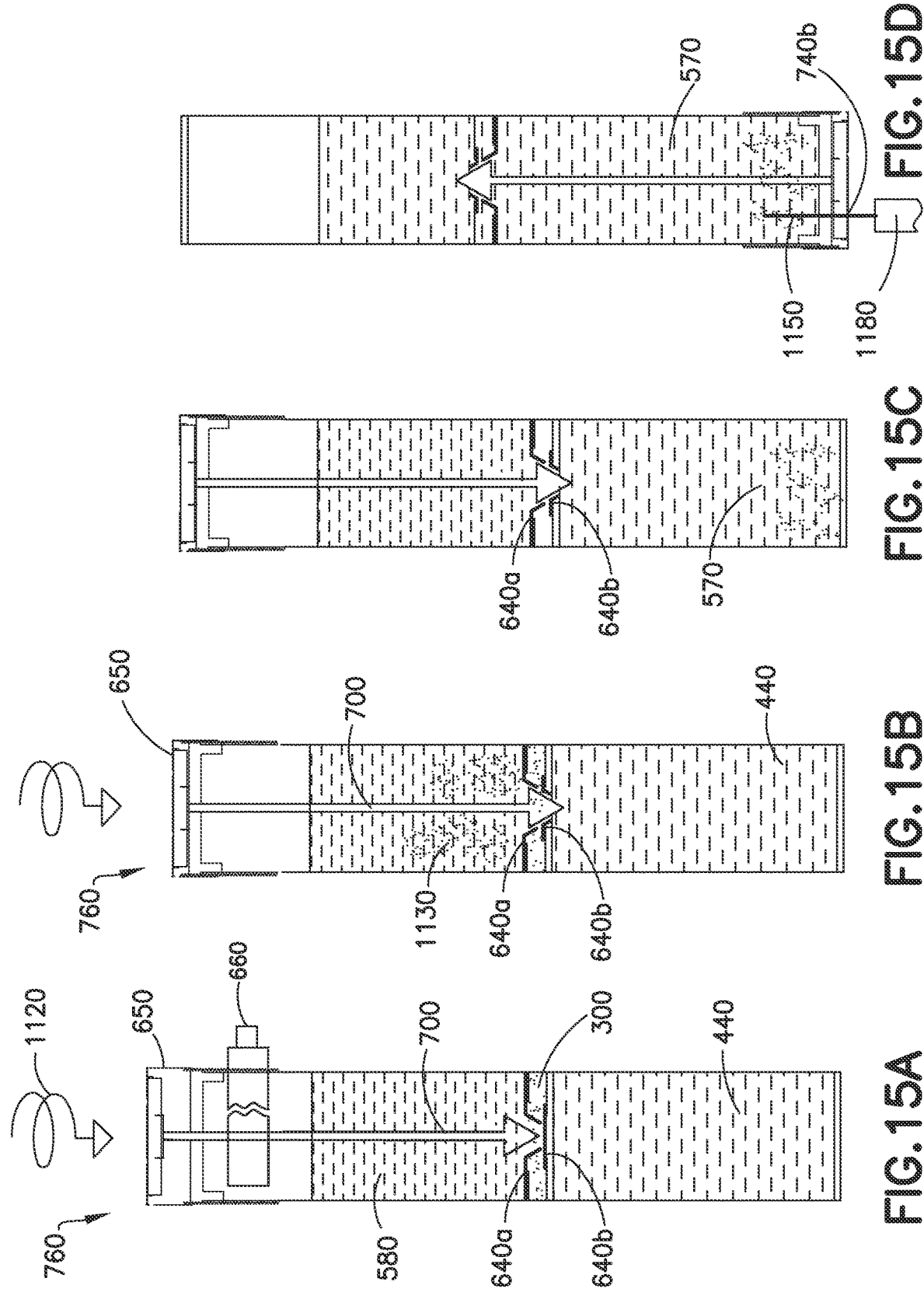

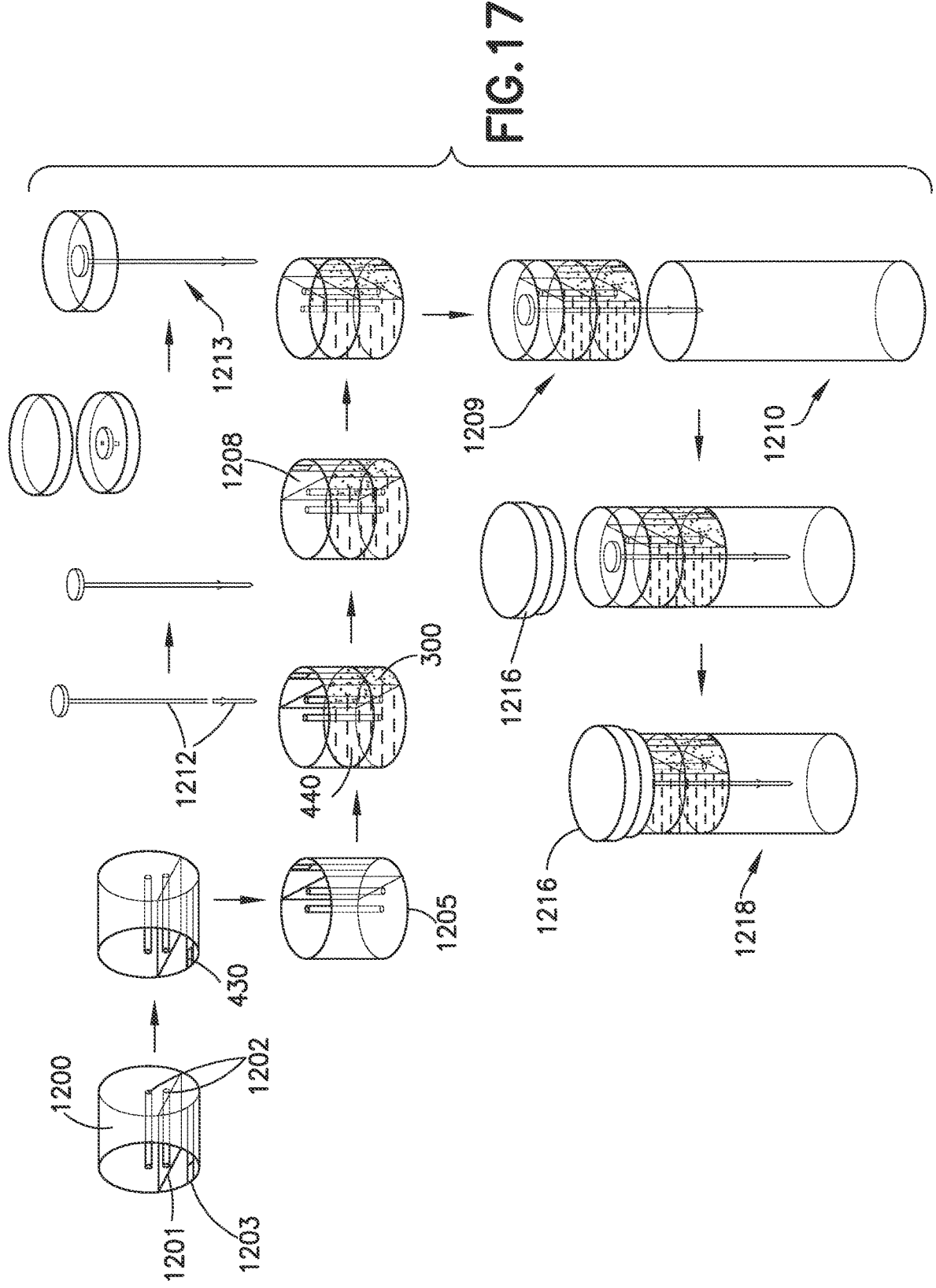

1604          1604

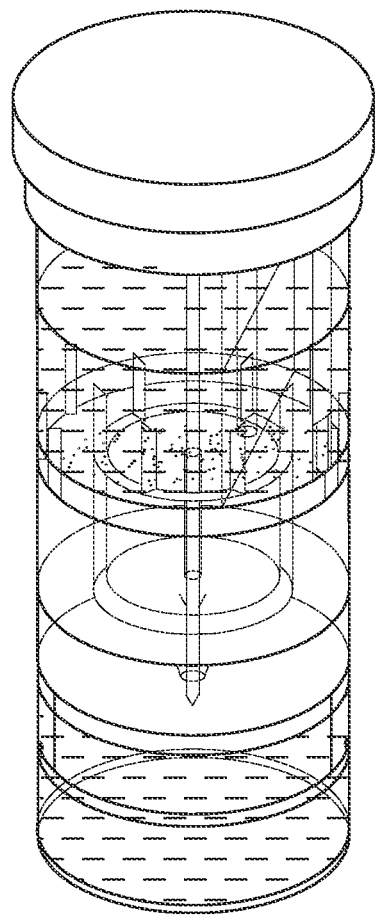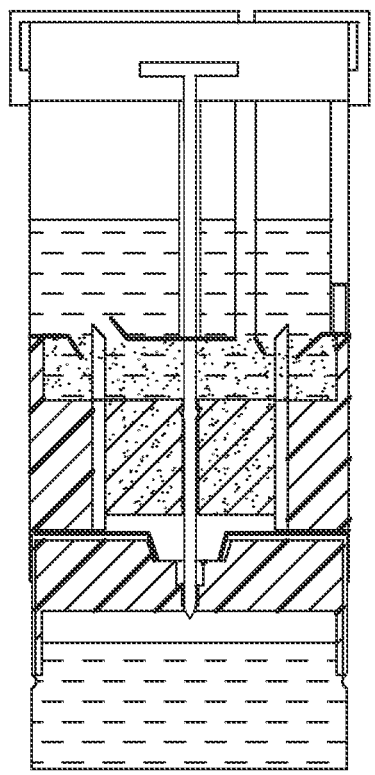
1615
FIG.22C
1615
FIG.22D

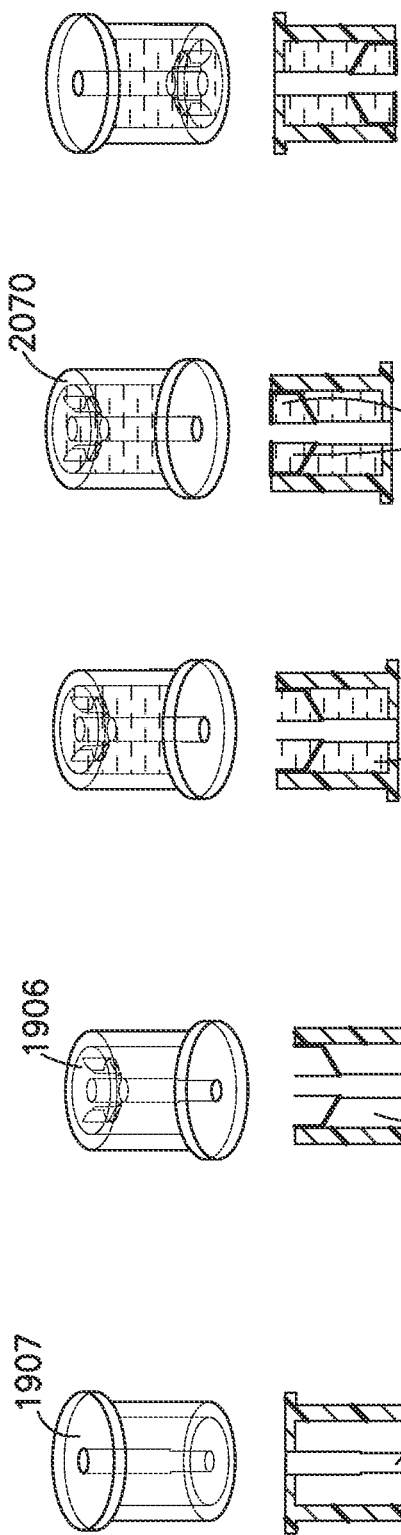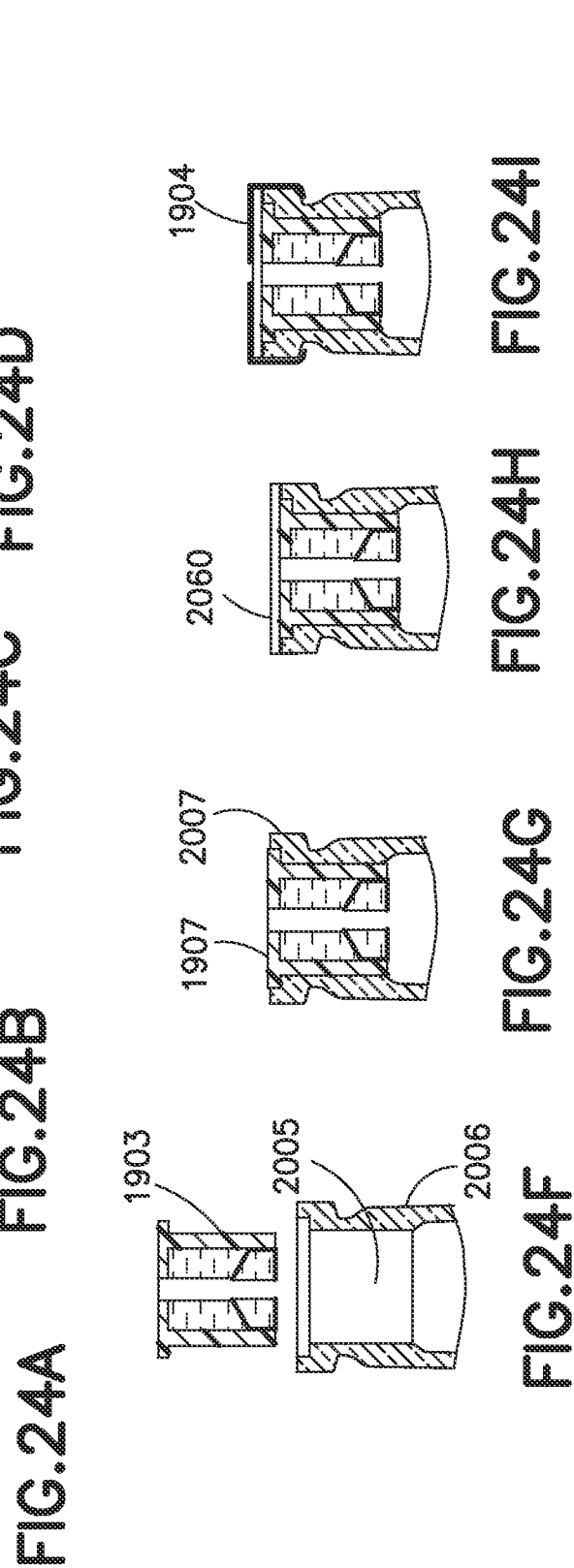

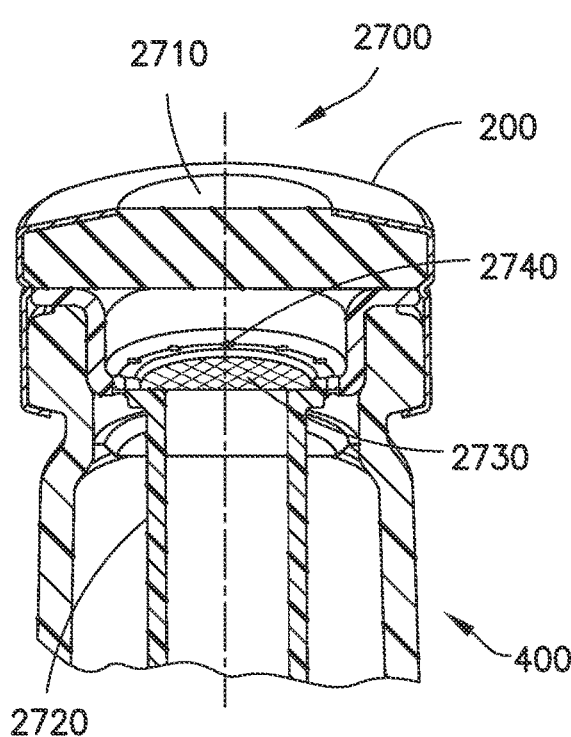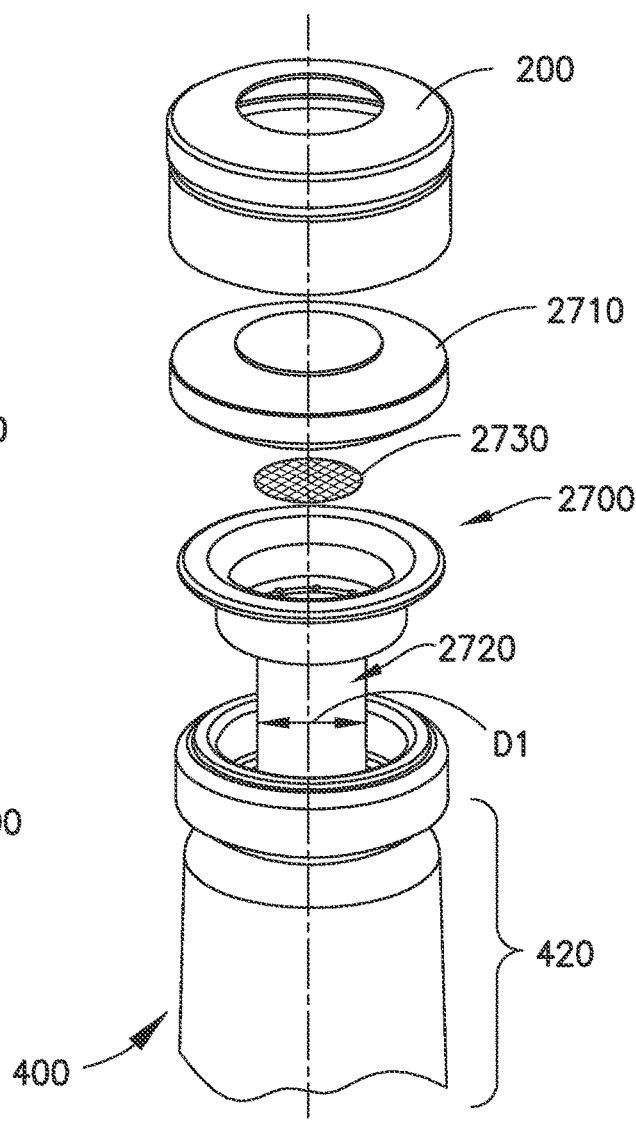
FIG.27A
FIG.27B

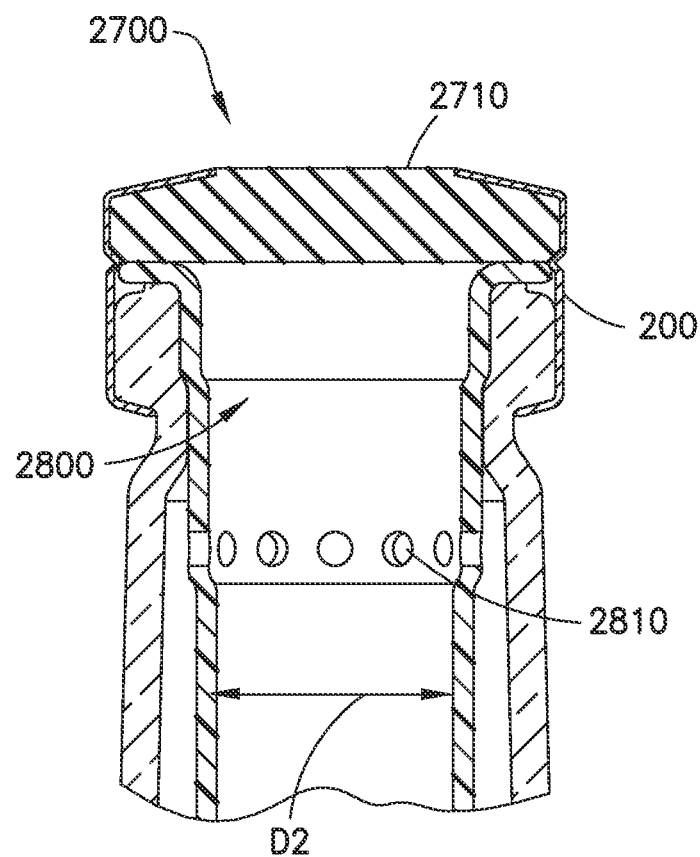
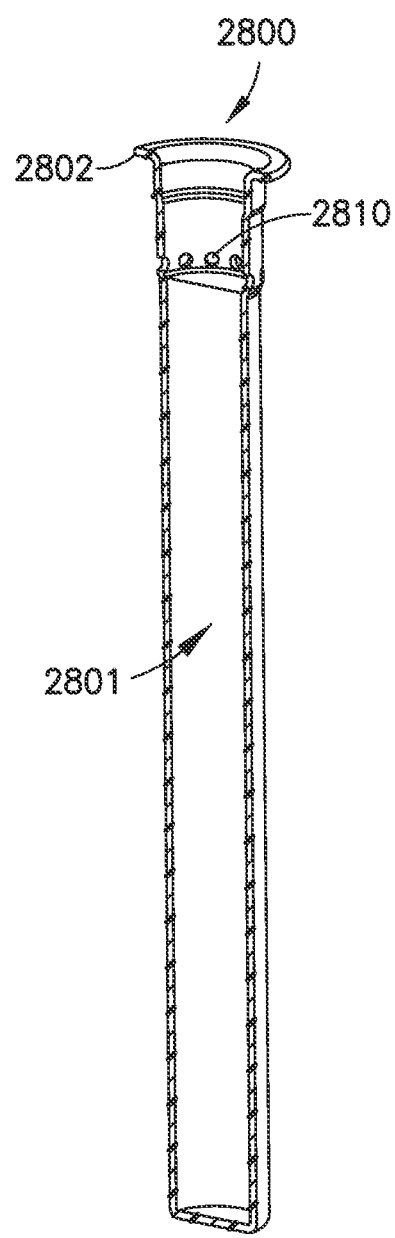
FIG.28A
FIG.28B

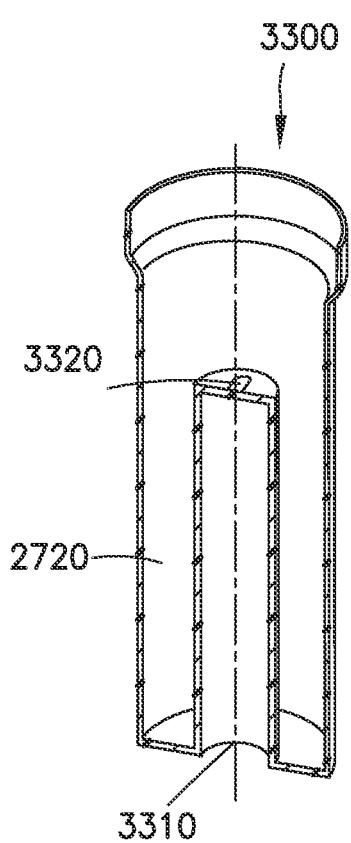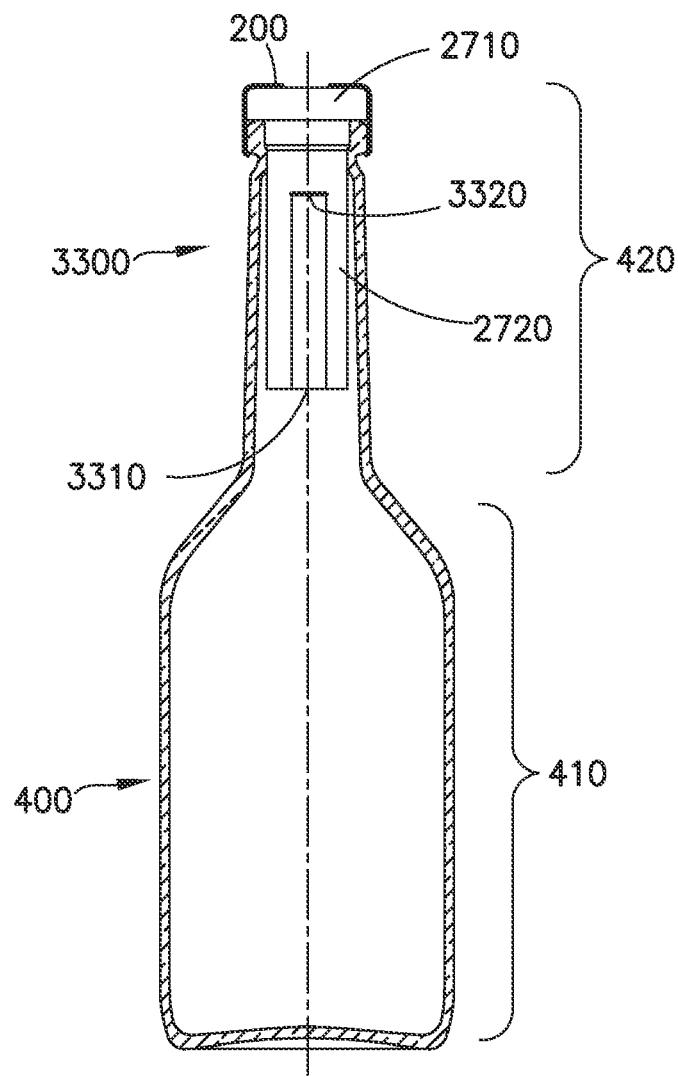
FIG.33A
FIG.33B

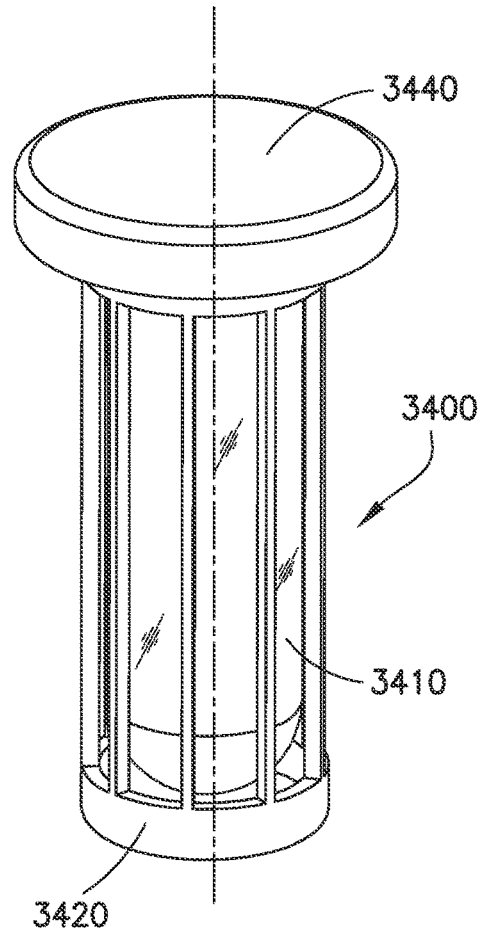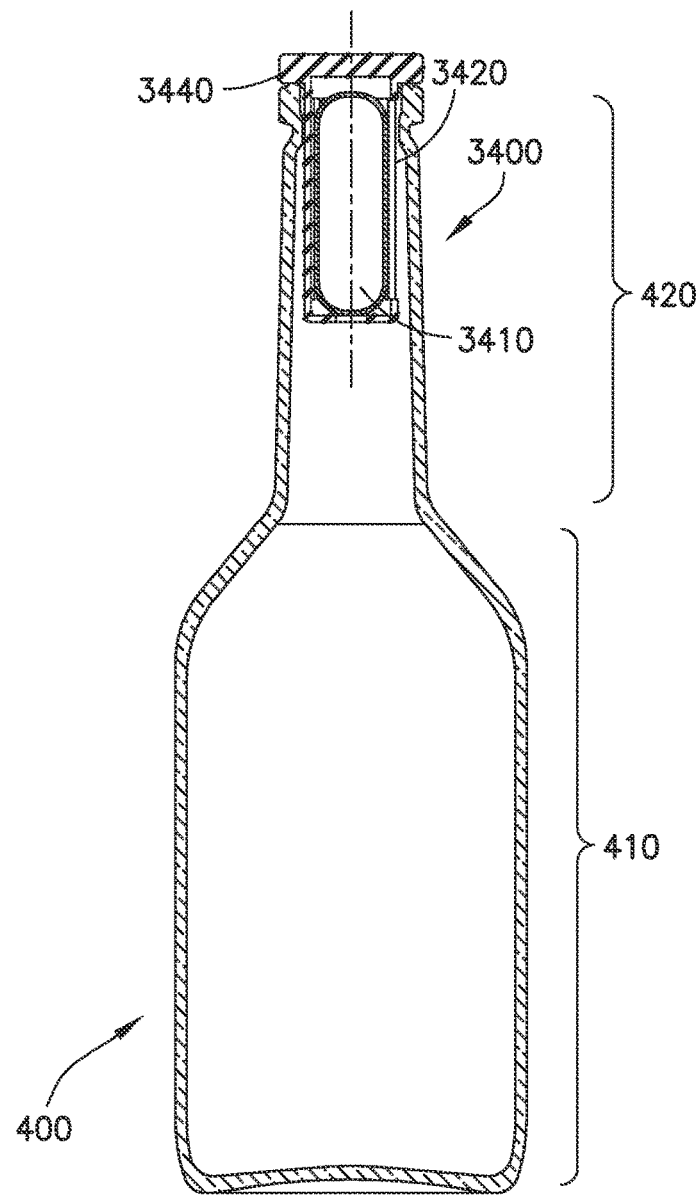
FIG.34A
FIG.34B

BLOOD CULTURE BOTTLES WITH MECHANISMS FOR CONTROLLED RELEASE OF SUBSTANCES INTO CULTURE MEDIA

CROSS-REFERENCE TO RELATED APPLICATIONS

The present application is a national phase entry under 35 U.S.C. § 371 of International Application No. PCT/US2014/062216 filed Oct. 24, 2014, published in English, which claims priority from U.S. Provisional Application No. 61/895,760, filed Oct. 25, 2013, and U.S. Provisional Application No. 62/032,329, filed Aug. 1, 2014, the disclosures of which are hereby incorporated herein by reference.

BACKGROUND OF THE INVENTION

Sepsis is a significant healthcare issue due to its high frequency of occurrence and high mortality rate in hospitals. One of the leading causes of sepsis is a bloodstream infection (BSI). BSI is most commonly diagnosed by a blood culture, in which a sample of blood is incubated with a microorganism growth media in an atmosphere controlled to promote bacterial growth. Current automated blood culture systems can take 12-48 hours to detect the presence of infectious microorganisms in blood and can take up to 5 days to rule out the presence of any infectious microorganisms. Often times, additives must be combined with the blood culture to ensure that the presence or absence of a BSI is determined as quickly and accurately as possible. For example, a patient's blood at the time of sampling already contains antibiotics. The presence of antibiotics can further increase the time required to detect the presence of infectious microorganisms. Furthermore, it can take up to an additional 12-48 hours to identify the infection microorganisms by sub-culturing the positive blood culture and performing identification and antimicrobial susceptibility tests. These results can be too late to alter the treatment course and result in the death of the patient.

Adsorption resins of various kinds can be used to adsorb the presence of antibiotics in a patient's blood sample in order to reduce the time required to detect the presence of infectious microorganisms. In addition, adsorption of antibiotics from the patient's blood sample allows the microorganisms to recover and grow, thereby confirming the presence of those microorganisms in the sample. The adsorption resin and microorganism growth media are typically present in one mixture disposed in a sealed container. In addition to reducing the time of microorganism detection by mitigating the effects of antibiotics on microorganism growth, blood samples are often filtered to capture any microorganisms if present, for a faster bacterial time to detection. However, the practice is currently performed in a general microbiology laboratory with multiple tools and steps.

It has been discovered that certain components of an optimized media formulation are incompatible with resins. For example, when a lytic media is present in the mixture containing adsorption resin and a growth media, the adsorption resin may adsorb components of the lytic reagent. Such adsorption results in a loss of lytic function. Separating the lysis reagent from the resin and culture media in a single closed system is desired in order to enhance the stability of the media and to minimize non-specific adsorption of the media components that are necessary for microorganism growth (e.g., nutrients, detergents, etc.). Therefore, improved methods and apparatuses for combining additives to blood cultures, and processing blood samples for diagnosis of BSI continue to be sought.

BRIEF SUMMARY OF THE INVENTION

Described herein are methods and apparatuses for releasing various sample constituents into a blood sample/blood culture. In one embodiment a time-controlled release mechanism is contemplated that allows mixing of certain constituents into a blood sample/blood culture at a preferred time interval. The methods relate particularly to BSI detection and are described in that context. However, one skilled in the art will appreciate that the methods and apparatuses described herein can be used in a variety of contexts where controlled combination of constituents for downstream analysis is sought. Likewise, one skilled in the art would also recognize that the methods and apparatus described herein are also suitable for use with any type of biological sample, including any sterile body fluid such as blood, lactate, spinal fluid, urine, etc.

In embodiments of the methods and apparatus described herein, blood culture bottles such as BACTEC FX™ 9000 series manufactured by Becton Dickinson Diagnostic Instrument Systems may be used. These aforementioned bottles may have a plurality of separate chambers for separating various elements, e.g., one chamber may contain a microorganism growth media, while another chamber may contain an adsorption resin or a lytic reagent. Each chamber may separate each element from each other element and have various means of releasing the contents of the chambers at desired times either by manual or automated control using, for example, a system such as the BACTEC FX 9000 series instruments. By controlling the combination of chamber constituents such as adsorption reagent (e.g., resin), lytic reagent and growth media, the adsorption of the antibiotics in the blood sample by the resin can be controlled. As used herein, manual control or manual operation requires some operator participation or intervention to achieve beyond control of the automated systems themselves. Automated control or automated operation, in contrast, requires no physical intervention by the operator beyond control of the systems and apparatus used to perform the automated function.

In another embodiment, a method and apparatus for inoculating the sample through a time-controlled process in a single system is described. In one embodiment, the apparatus described herein has two chambers and a release mechanism that is controlled by a pushing or pressing force. The release mechanism allows the chamber contents to be combined.

In one embodiment, the chambers are disposed in a bottle. A rod having a pointed tip is attached to a cap affixed to the bottle. The rod points downward from the cap. A sensor is located at the bottom of the blood culture bottle. Alternatively, the sensor may be located anywhere in the blood culture bottle, be suspended inside the bottle or be soluble in the culture media. The sensor monitors environmental conditions in the blood culture that are indicative of the presence or absence of microorganisms. In other embodiments, the conditions of the culture can be monitored by measuring cell density or cell impendence properties in lieu of a sensor. The blood sample is disposed in a chamber above the chamber in which the growth media is disposed. The tip of the rod pierces the chamber allowing the blood sample to combine with the growth media. The apparatus for releasing the blood sample into the growth media and adsorption chamber can also control the distance to which the blood sample penetrates into the blood culture bottle. In other words, the penetration force can be calibrated to control the extent to which the sample is dispensed into the media. Such control can be manual or automatic.

In other embodiments, more than one chamber is present. The pushing motion can be controlled so that only the seal of the first chamber is breached. At a later time, a second push will breach one or more additional chamber seals. Alternatively, one push can breach multiple chamber seals simultaneously. Once the seals are broken, the contents of the chamber in which the seal was breached are brought into communication with the contents of the adjacent chamber. Once all of the seals are broken, the tapered rod extends into the bottom most chamber. In one embodiment, the extended rod acts as a stirrer, and is stirred either by automated or manual internal or external force, such as ferromagnetism.

In another embodiment, the release mechanism is a screw mechanism which is operated by a twisting force. A cap containing internal screw threads and a rod feature having a sharpened end point is inserted into a blood culture bottle having external screw threads and containing one or more separate sealed chambers. A blood sample is deposited into a first chamber through a cap aperture or a stopper made of resilient material (e.g. a septum stopper). At a preferred time, the cap is twisted downward, either automatically or manually, forcing the tapered end of the rod to break through the seal separating first and second chambers allowing the blood sample of the first chamber to combine with the contents of the second chamber. The screw release mechanism can be controlled, automatically or manually, to breach individual compartment seals sequentially or virtually simultaneously. Once all of the chamber seals have been breached and their contents are combined with each other for a desired or predetermined time, the apparatus may be inverted, automatically or manually, to release the combined contents into a separate receptacle for further testing.

In yet another embodiment, the apparatus has more than one puncture mechanism. In this embodiment, top and bottom receptacles are joined together and advanced toward each other to cause the mechanism to puncture seals between the receptacle chambers. Specifically, one insert having one or more chambers is placed into a top receptacle of the bottle, which is fitted over a bottom receptacle of the bottle that contains a filter and a filtration collection chamber. The top receptacle has a puncture mechanism (e.g., a rod with a tapered point) fitted in the cap of the top receptacle while the bottom receptacle has spikes pointing toward the top receptacle.

The top receptacle is placed over the bottom receptacle which forms an additional chamber between the top and bottom receptacles. In one embodiment, this chamber has a pressure that is less than the normal atmospheric pressure. Alternatively, the chamber can be empty or can contain a substance such as a lysing reagent. Empty chamber(s) and empty portions of chamber(s) described herein are referred to as the chamber or device headspace as appropriate.

The blood sample is introduced into the chamber between the top and bottom receptacles through an aperture or septum in the cap of the top receptacle. The top and bottom receptacles are advanced toward each other, either manually or automatically. As the receptacles are advanced, the tapered end of the rod in the top receptacle punctures the seal separating the filtration chamber from the adjacent chamber. Also, the spikes of the bottom receptacle puncture the seal separating the chamber insert from the adjacent chamber. Advancing the top and the bottom receptacles toward each other can be a controlled advance that allows only the filtration seal to be broken initially and the other chamber seals broken subsequently, or breaking both the filtration seal and the chamber seal simultaneously. Once the seals between the chambers are broken, the contents of the chambers combine, forming a concentrate in the top portion of the chamber, while the excess liquid by-product is filtered as it flows into and through the filtration collection chamber.

In an alternative embodiment, the receptacles are advanced using a screw mechanism, where the top receptacle and the bottom receptacle are advanced toward each other by twisting one or both receptacles relative to the other.

In yet another embodiment, a ferromagnetic cutter is used to puncture one or more seals to combine the contents of one or more chambers in support of processing the sample. One or more separately sealed inserts containing a chamber and a ferromagnetic cutter are placed into the blood culture bottle and enclosed by a cap containing a fluid passage running the length of at least one insert. An additional bottom chamber may be formed by fitting the insert into the blood culture bottle. The blood sample is introduced into the blood culture bottle through the fluid passage. Other embodiments may have the blood sample initially introduced into one of the chambers in the insert before or after placing the insert in the bottle.

The ferromagnetic cutter is activated either manually or automatically. The cutter is advanced along the shaft formed by the fluid passage puncturing seals between the chambers causing the contents of a chamber to combine with the contents of an adjacent chamber. Advancing the ferromagnetic cutter is controlled to break through seals sequentially or break through multiple seals virtually simultaneously. The ferromagnetic cutter can be controlled to continue to rotate after it emerges from the fluid passage and is introduced into the culture bottle, further mixing the contents from separate chambers in the culture until a preferred mixture is reached.

In an alternative embodiment a tapered rod is advanced through the passage, either automatically or manually. In automatic mode, a magnetic force is used to advance the rod. Other release mechanisms, such as those discussed above (e.g., twisting, pushing) are used to advance the tapered rod through the fluid passage.

In another embodiment, a magnetic bead is used to abrade a biologically inert polymer (e.g., silicone barrier) that separates a resin from the media. The magnetic bead is disposed in a bottom chamber, which contains a silicone sensor, a resin, a barrier and a culture media. The magnetic bead abrades the silicone barrier to combine the resin with the media and blood culture when activated by an external force. The blood sample is introduced into the blood culture bottle through a pierceable cap used to seal the bottle. The external force can be a magnetic force that is activated other manually or automatically. In other embodiments, external forces such as sonic, electrical and gravitational forces can be used to fully or partially disrupt the biologically inert polymer. Mechanically-induced forces (e.g., agitation, centrifugation, etc.) are also contemplated.

Alternative embodiments contemplate the use of a molded insert placed in the blood culture bottle. In these embodiments, the chamber described above is provided in the insert. The molded insert is suspended in the culture bottle from the neck or detached and suspended inside the culture bottle such that it can be agitated by way of an external force. Various types of flanges and caps are used to secure the insert in the culture bottle. A septum stopper or septum cap is also provided through which the bottle is inoculated with the blood sample to be cultured. In some embodiments, the cap is detached from the culture bottle by a pierceable needle. In other embodiment, the cap is detached by means such as pulling twisting, etc., before the needle penetrates through the septum.

In one embodiment, the insert has a tubular-shaped chamber in which reagents for blood culture (e.g., resin and/or lytic media) are disposed for delivery into the culture bottle for combination with culture media and other reagents. The insert has a body and a wider top portion to secure the insert to the neck of the culture bottle. The tubular chamber of the insert is sealed with a membrane. The insert is secured to the culture bottle by a septum/cap assembly. The wider top portion of the insert contains openings that are in fluid communication with the culture bottle. As such, blood introduced into the insert will flow from the insert into the culture bottle. Once the seal membrane is ruptured, the contents of the insert (e.g., the resin and/or lytic media) will also flow through the openings into the lower chamber of the culture bottle when the bottle/insert assembly is inverted. The blood sample is introduced into the culture bottle by way of a needle which pierces the cap and breaks the membrane.

In another embodiment, the molded insert has a uniform body portion that extends through the neck of the culture bottle and is secured to the culture bottle by a septum or by a flange. There are openings near the top that permit fluid communication between the interior of the insert and the blood culture bottle. There is a seal disposed below the openings that, when broken, places the contents of insert in fluid communication with the contents of the culture bottle if the bottle/insert assembly is inverted to facilitate intermixing of the contents of the insert with the contents of the culture bottle.

In yet another embodiment, the insert is configured as a stopper having a head portion, a hollow body portion and a base portion. The head portion rests on and above the neck of the culture bottle. The hollow body portion is the chamber that contains the compositions/reagents to be combined with the blood and blood culture media (e.g., resin and/or lytic media). The base portion is a membrane for keeping the contents of the insert from intermixing with the contents of the culture bottle. The insert is secured to the culture bottle by a septum cap that covers the head portion of the stopper insert and fastens to the neck of the culture bottle. The large cap and the septum are pierceable. The blood sample may be introduced into the culture bottle by a sample delivery device having a cannula within a needle through which the blood can flow. Preferably, the needle punctures the pierceable cap/septum and tears or breaks the base membrane thereby allowing the blood sample and the content of the insert to flow into the culture bottle through the cannula and mix with those contents. As is known to the skilled person, a septum stopper or septum cap is a resilient stopper or cap that is pierceable by a needle yet adapted to maintain the seal, and continue to maintain the seal, even after the needle is withdrawn.

In an alternative embodiment, the insert is configured to be received through the neck of the culture bottle. The insert is secured to the culture bottle by a septum having a top diameter that allows the septum to rest on the top of the culture bottle neck. The bottom portion of the septum is convex and is secured in a concave portion of the insert, allowing the insert to be suspended in the culture bottle and secured to the neck by the septum. Beneath the septum is a barrier between the septum and the upper portion of the insert that defines a chamber. In some embodiments, action of the needle causes the insert to disengage and fall into the culture bottle, facilitating intermixing of the contents of the insert, the contents of the culture bottle and the blood. In other embodiments, a seal at the bottom portion of the insert is held in place by vacuum. When the needle pierces the seal and introduces blood into the insert, the seal falls off, allowing the contents of the insert to flow into the blood culture bottle. Either way, the contents of the insert are intermixed with the contents of the blood culture bottle and blood as a consequence of the advancing needle.

In another embodiment, the insert, again is received through and fastened on the neck of the blood culture bottle. The portion of the insert that extends into the blood culture bottle has a raised central portion that forms a tube in the bottom portion of the insert. The top of this tube has a pierceable seal, keeping the contents of the chamber from flowing into the culture bottle while the seal remains intact. When the bottle is inoculated with blood delivered by syringe, the needle pierces the seal, allowing the blood to flow through the tube of the insert and into the culture bottle. The contents of the chamber are intermixed with the contents of the bottle either by inverting the bottle to allow the contents of the chamber to flow through the ruptured seal into the culture bottle, or by having the bottom portion of the chamber break from the top portion, causing the contents of the chamber to mix with the contents of the blood culture bottle.

In yet another embodiment, the chamber is a septum cage. The cage can hold one or more capsules having reagents (e.g., resin) inside. The capsules are not soluble in the contents of the blood culture bottle and are positioned so that they are fragmented when the needle used to inoculate the blood culture with blood pierces the cage and its contents, releasing the capsule contents into the blood culture bottle.

In an alternative embodiment, the chamber is made of a non-molded material that is fully or partially disrupted by an addition of a chemical (e.g., a small molecule, a protein, etc.). The chamber may be suspended inside the culture bottle unsecured. Alternatively, the chamber may be disrupted by a change in environmental conditions such as a change in pH and/or ionic strength or by an external force.

BRIEF DESCRIPTION OF THE DRAWINGS

To assist those of ordinary skill in the relevant art in making and using the subject matter thereof, reference is made to the appended drawings.

FIGS. 2A-D are cut away side views of a chamber and rod assembly.

FIGS. 5A-C are a cut away side views illustrating the operation of the insert to release resin into blood culture.

FIG. 10A is a cut away side view of another embodiment of a blood culture bottle having a chamber and piercing mechanism. FIG. 10B is a cut away side view of an alternative embodiment of the piercing mechanism.

FIGS. 11A-B are schematic side views illustrating the operation of a piercing mechanism by screwing or twisting a cap.

FIGS. 15A-D are schematic side views illustrating the combination of the chamber contents in the device of FIGS. 14A-D with blood and blood culture media.

FIG. 17 is a series of perspective views of the insert configurations of FIGS. 16A-B.

FIGS. 22A-D are perspective and side views of the device of FIG. 17 at various stages of operation.

FIGS. 24A-I illustrate the assembly of the ferromagnetic cutter of FIGS. 23A-C.

FIGS. 27A-D illustrate cut away side views (27A and 27C) and perspective views (27B and 27D) of an alternative embodiment of a molded insert assembly having a tubular-shaped chamber for housing reagents that is suspended from the neck of a culture bottle.

FIGS. 28A-D are cut away side views of an alternative embodiment of a molded insert having a uniform body portion and openings near the top of the insert.

FIGS. 33A-B are cut away side views of the insert having a raised central portion.

FIG. 34A-B are perspective views of an alternative embodiment of the insert where the chamber is a septum cage for hosing a capsule. FIG. 34B is a cut away side view of the insert disposed inside a culture bottle.

FIG. 36E illustrates the culture bottle that houses the barrel/plunger insert assembly.

FIGS. 37E-F are perspective views of the barrel/plunger insert assembly disposed inside the culture bottle.

DETAILED DESCRIPTION

Described herein are methods and an apparatus, configured to control the timing and sequence for combining constituents of a sample assay. In one embodiment, the method and apparatus is configured for the controlled release of various blood culture components. In those embodiments, a blood culture bottle is provided having one or more separate sealed chambers. The blood culture bottle is fitted with a mechanism that punctures the seal between the chambers. Optionally, the mechanism is activated, automatically or manually, by a time-controlled mechanism. The mechanism breaches the one or more seals of a first chamber allowing the blood sample to come into communication with the chamber contents. The mechanism can be further advanced to pierce additional (optional) seals causing the constituents combined first to be further combined with the constituents of another adjacent chamber or the blood culture itself. Although embodiments are described herein in the context of a BSI assay, the apparatus and methods described herein can be used to effect controlled combination of constituents for a wide variety of tests, investigations and processes such as, for example, chemical reactions and composite blending.

Figure 1A:
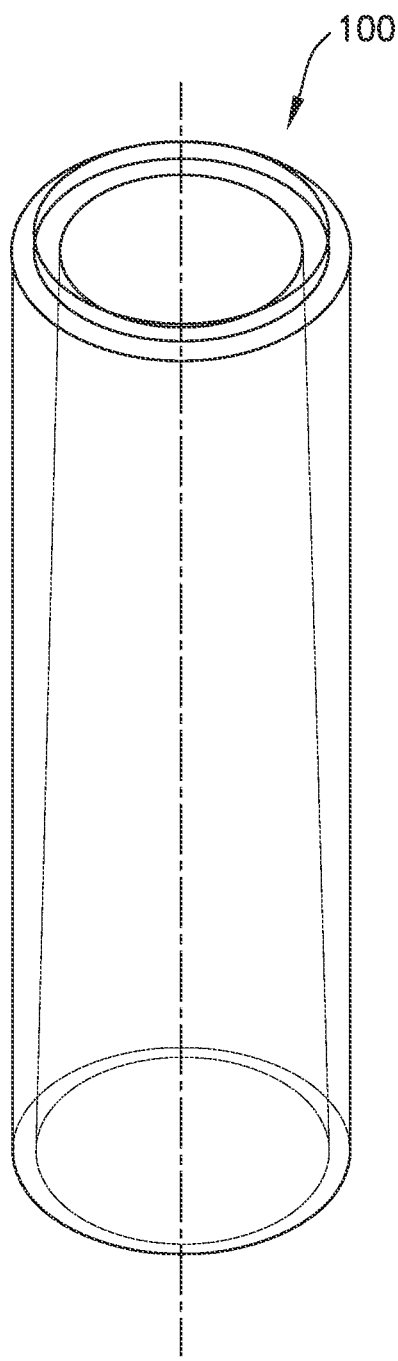
FIGS. 1A-B are perspective views of an adsorption resin chamber and a tapered rod.
Figure 1B:
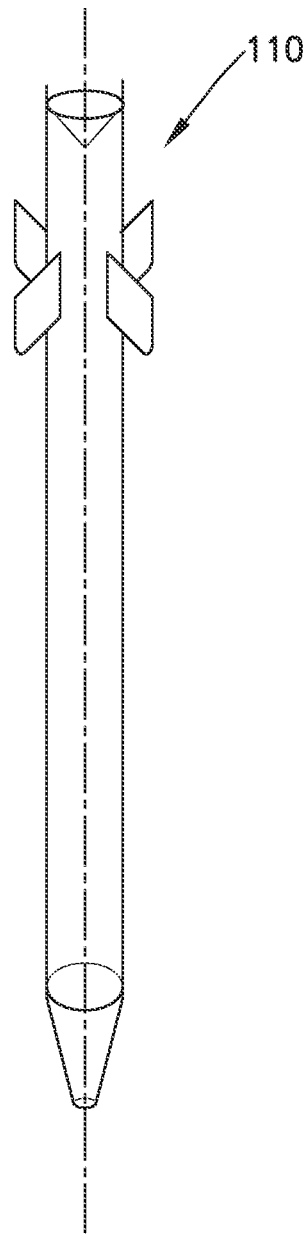
Figure 2A:
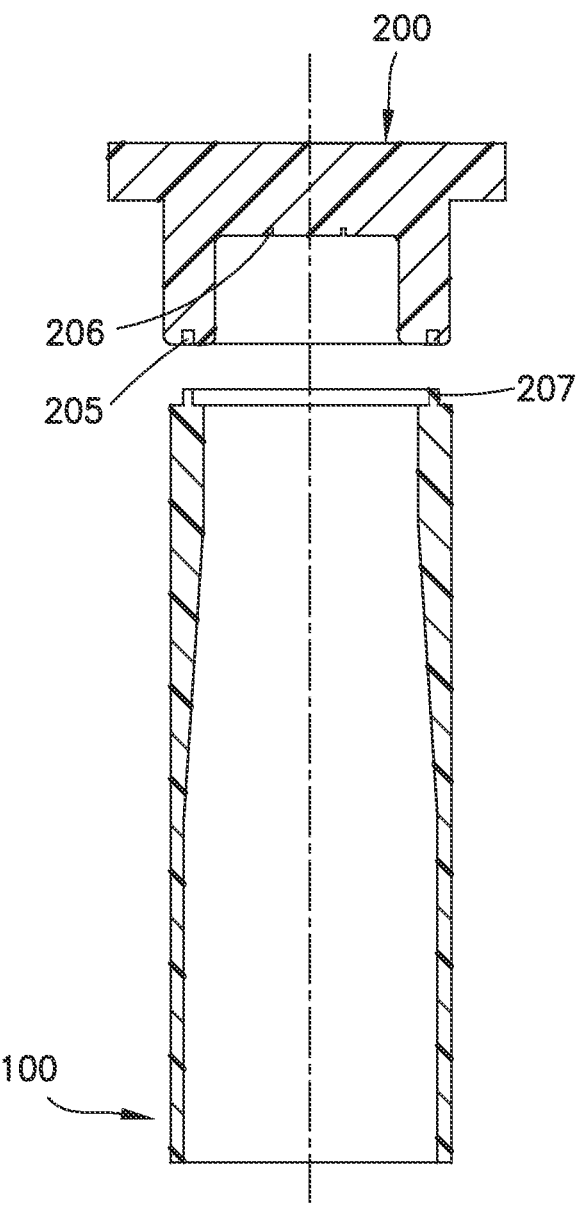
Figure 2B:
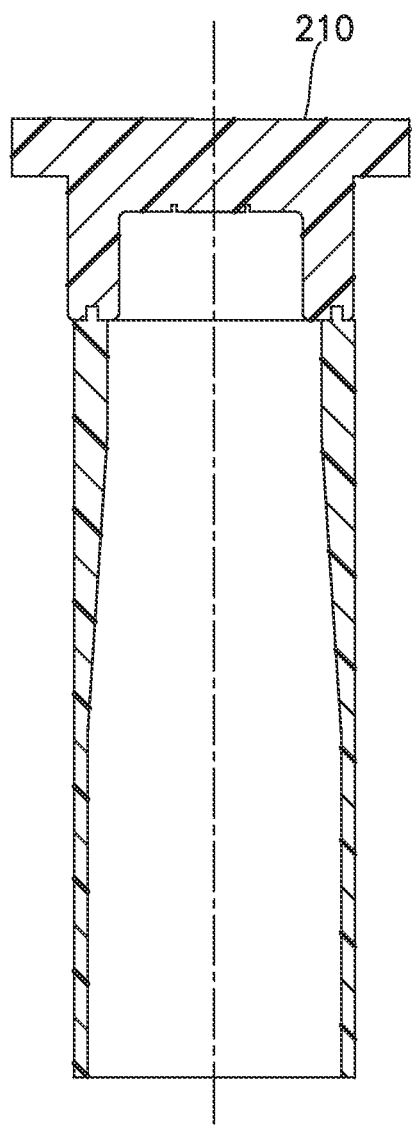

FIG. 5A illustrates one embodiment of a sealed chamber insert 320 situated above a lower chamber 450 of a blood culture bottle. A blood sample is delivered from a sample delivery device through an aperture or septum. For example, the sample delivery device may have a cannula within a needle through which the blood sample can flow. Suitable commercially available blood culture bottles include BACTEC FX 9000 series manufactured by Becton Dickinson. FIG. 1 shows two parts of the sealed chamber insert 320, a tubular vestibule 100 and tapered rod 110 having intersecting bars.

Figures 3A, 3B:
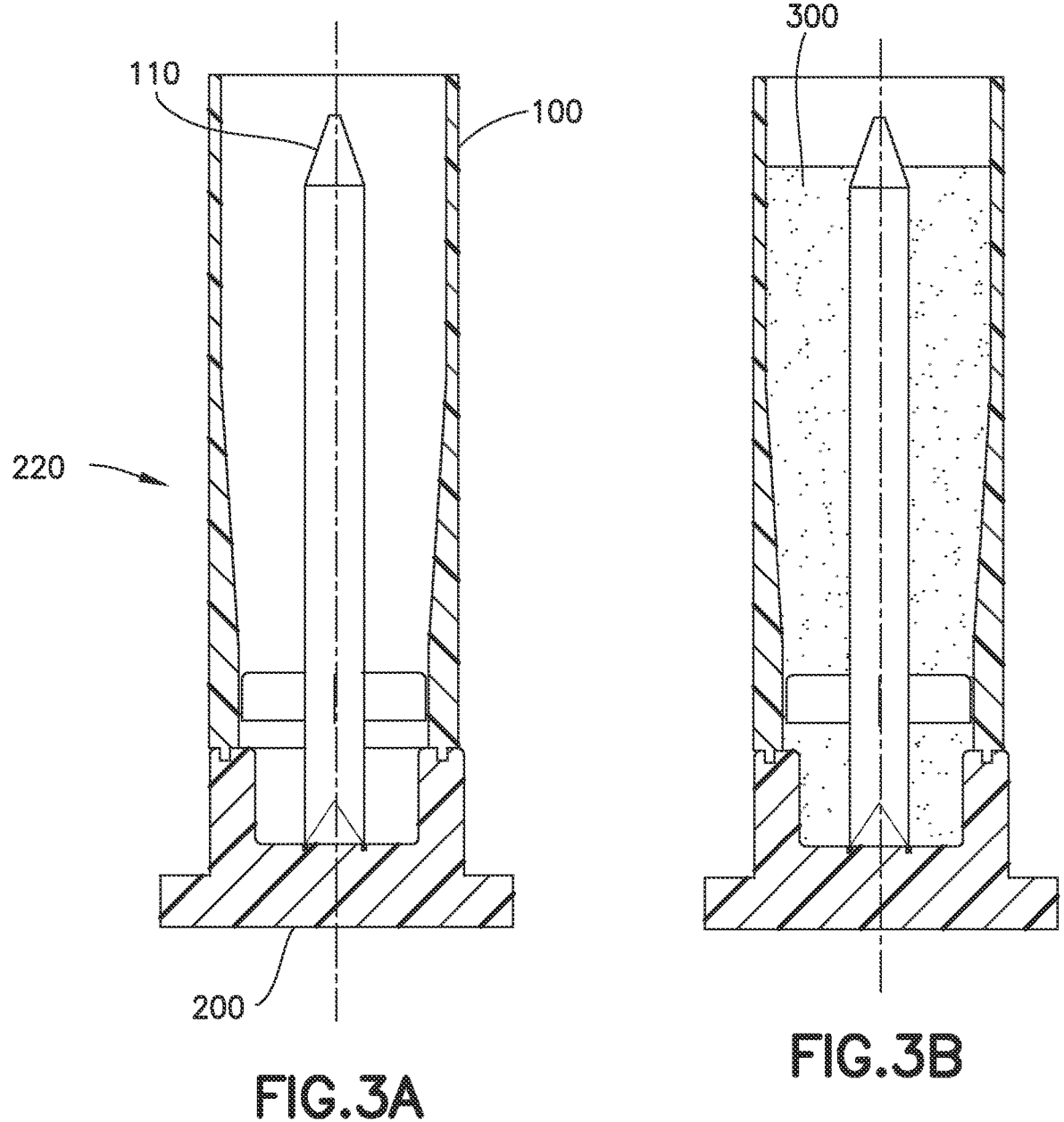
FIGS. 3A-D are cut away side views of a sealed rod/chamber assembly with the chamber containing resin.
Figure 3C:
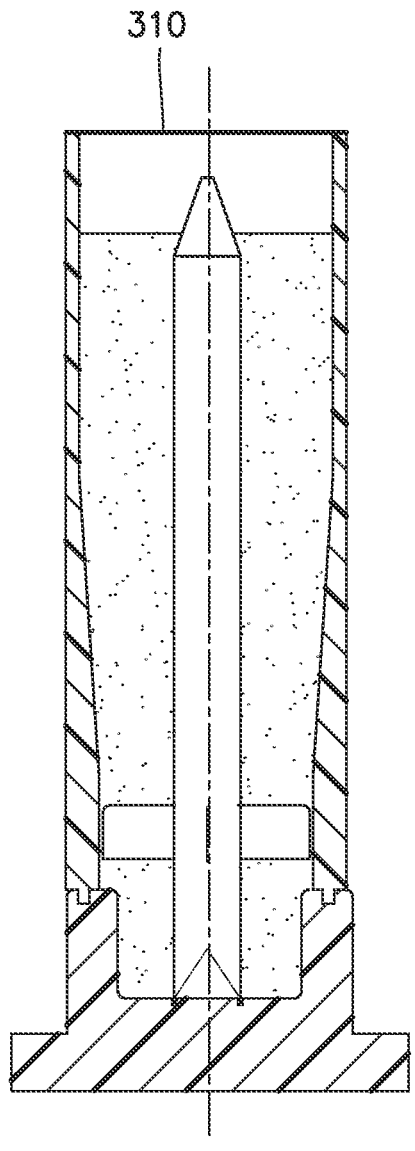
Figure 3D:
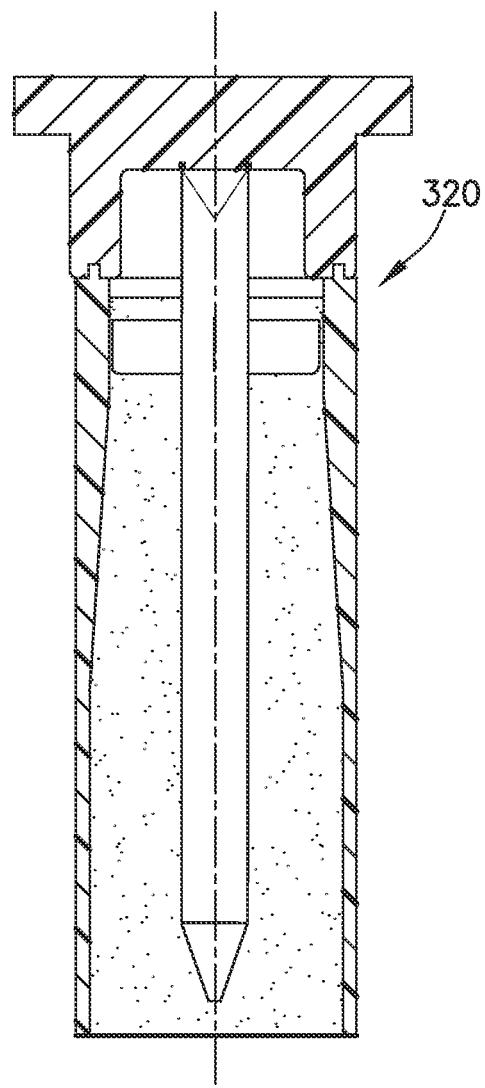

FIGS. 2A-D illustrate how the rod 110 and tubular vestibule 100 are assembled with the cap 200. The cap 200 contains lower inlets 205 and upper inlets 206. The lower inlets 205 are sized to allow the cap 200 to be fitted over the tubular vestibule 100 by receiving tabs 207; thereby creating the housing portion 210 of the chamber insert. The upper inlets 206 are sized to receive the tabs 208 on the rod 110. As in FIG. 2C, the rod 110 is positioned so that the intersecting bars are free from contact with the walls of the tubular vestibule 100. Once the rod 110 and the tubular vestibule 100 are fitted into the cap 200, the resulting assembly 220 is inverted as in FIGS. 3A-B.

FIGS. 3A-D illustrate how the assembly 220 is filled and sealed. The assembly 220 is first inverted and then filled with a desired constituent or additive, which in this embodiment, is an adsorption resin 300. In other embodiments, the resin 300 may be mixed with media. After the assembly 220 is filled, a seal 310 (FIG. 3C) is affixed to the bottom of the assembly distal to the cap 200. Seal 310 may be a foil seal. The seal material is largely a matter of design choice; however, rod 110 must be able to puncture the chosen material. The filled assembly 320 (FIG. 3D) is then ready for placement in a container which will receive the adsorption resin 300 when the seal 310 is punctured.

Figure 4A:
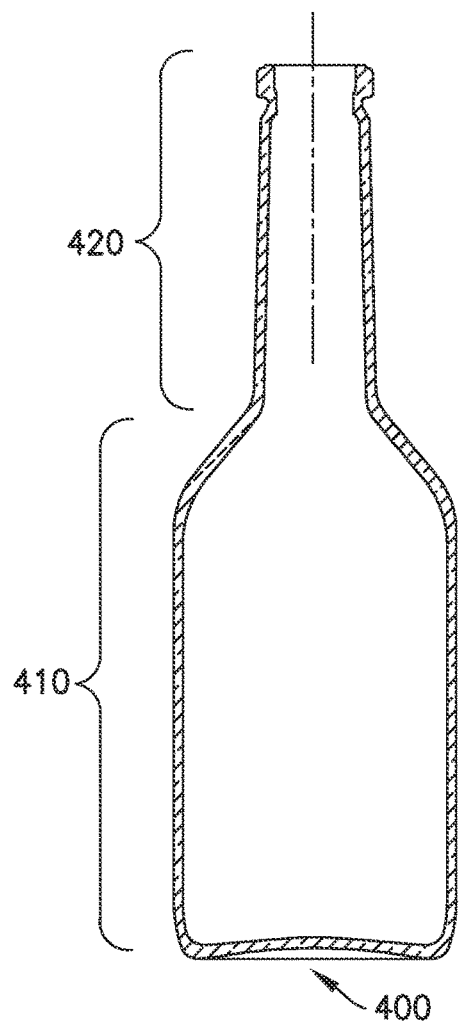
FIGS. 4A-B are cut away side views of assembly depicted in FIGS. 3A-D placed in a blood culture bottle containing a sensor.
Figure 4B:
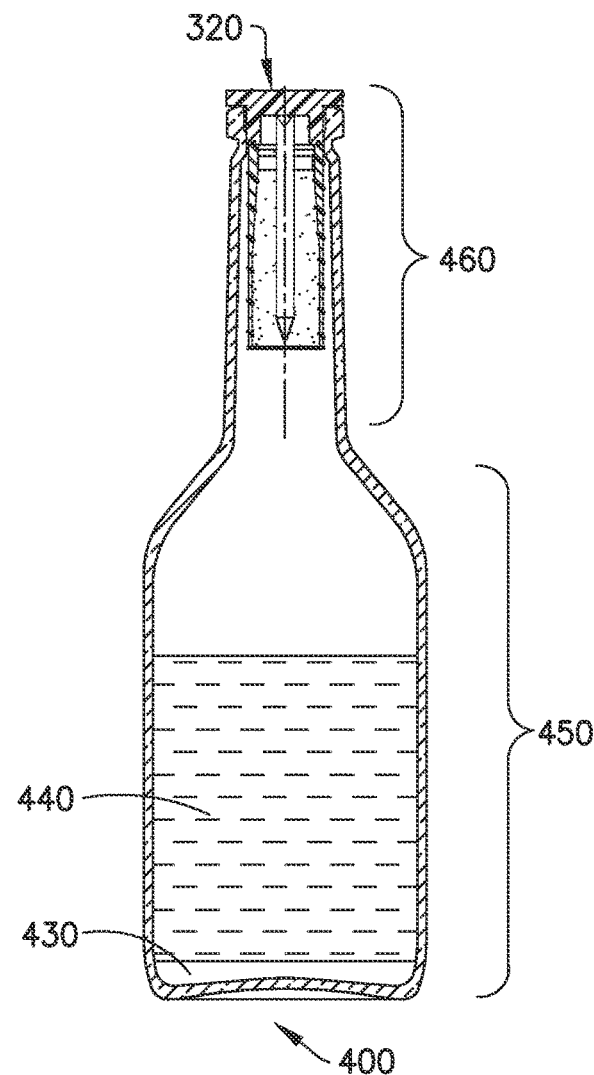

FIGS. 4A-B illustrate how the filled assembly 320 is placed in a blood culture bottle 400. The blood culture bottle 400 has a lower chamber 410 and a narrower upper chamber 420. The lower chamber has a sensor 430 located at the bottom of the blood culture bottle 400. Other embodiments may have more than one sensor and the sensor(s) may be located in other areas of the blood culture bottle 400. In this embodiment, the lower chamber 410 of the blood culture bottle 400 is filled with a media 440. Examples of media 440 can be found commercially in Becton Dickinson's BACTEC® Plus Aerobic/F, Plus Anaerobic/F, PEDS Plus/F, Lytic/10 Anaerobic/F, Standard/10 Aerobic/F, Standard Anaerobic/F, Myco/F Lytic and Mycosis IC/F culture media. After media 440 is introduced into the lower chamber 410, (the filled chamber 410 is 450), the resin chamber insert 320, is fitted into the upper chamber 420 through the top opening of the culture bottle 400.

FIGS. 5A-5C illustrate the release of various constituents into a culture media. In FIG. 5A, the insert 320 is in the first position in which it will receive sample (e.g., blood). A blood withdrawing device 500 is fitted over the culture bottle 400/insert 320 assembly in a first position. Next, the blood withdrawing device 500 is moved into a position where the needle 509 of the blood withdrawing device 500 pushes the rod 110 downward. When the needle 509 of the blood withdrawing device 500 pushes the rod 110 downward, the tapered end of the rod 110 pierces and punctures the foil seal 310 releasing the contents of the resin chamber insert 320 into the liquid media 440 (FIG. 5B). Optionally, rod 110—after being dispensed into the culture media 440, is activated either automatically or manually by ferromagnetism to stir the combined blood sample, resin, and media mixture 570 as shown in FIG. 5C.

The shape of the blood culture bottle 400 may vary so long as a chamber insert, such as the sealed resin chamber insert 320, is receivable therein. The number of chambers in a given insert within the blood culture bottle 400 may also vary depending on specific needs. The chambers can contain different substances in addition to or in place of resin 300 and media 440. The substances disposed in the chambers can be a solid, liquid, or gas or any combination of a solid, gas and/or liquid. For example, the media 440 can be supplied in a liquid or lyophilized form. The sensor is optional and its location is largely a matter of design choice so long as it can be detected by its corresponding detection element, such as, but not limited to, an optical device.

Figures 6A, 6B, 6C:
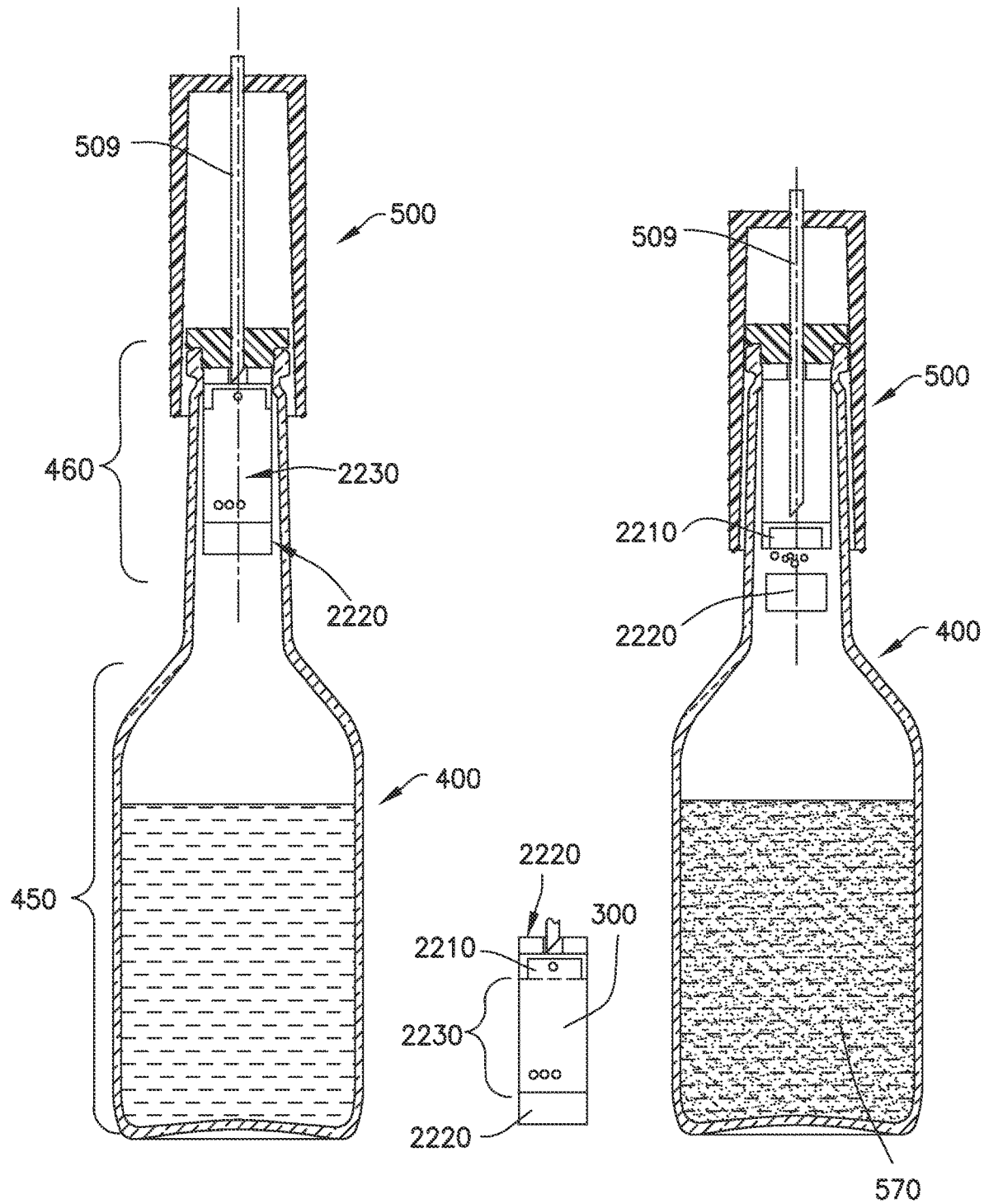
FIGS. 6A-C illustrates an alternative embodiment of the FIGS. 3A-D chamber in a cut away side views.

FIGS. 6A-C illustrate an alternative embodiment of the invention having a different resin release assembly. A resin release assembly 2200 is situated above a lower chamber 450 of a blood culture bottle 400. The assembly 2200 has a top movable seal element 2210, a bottom movable seal element 2220, and a compartment 2230 to hold the resin 300 (FIG. 6B). The bottom movable seal 2220 isolates the resin 300 from the media 440 disposed in the bottom chamber 410 of the culture bottle 400 (the bottom chamber 410 filled with media 440 is 450; the narrower upper chamber 420 with the insert is 460). The top and bottom movable seal elements can be of any form suitable to seal the chamber contents. In an exemplary embodiment, the compartment 2230 is a cylinder and the movable seals are disks. A blood sample is delivered through a needle 509 that is housed in cap assembly 500. Repressing the cap assembly 500 advances the needle 509 into the culture bottle 400. The compartment 2230 is first filled with resin 300 prior to both movable seal elements 2210, 2220 being placed to seal the resin 300 in the compartment 2230. Once assembled, the resin release assembly 2200 is placed into the upper chamber 420 of the blood culture bottle (shown as 460).

FIG. 6C further illustrates the operation of the resin release assembly 2200. The top 2210 and bottom 2220 movable seals are movably engaged within the chamber. A breakable seal (not shown) is placed directly above the resin release assembly 2200 such that it does not interfere with the advancement of the movable seal elements 2210 and 2220 by the needle 509. After the cap assembly 500 is securely placed on top of the blood culture bottle 400, the cap is depressed into the bottle 400 thereby advancing the needle 509 through the breakable seal (not shown) and into the chamber 2200. Advancing the needle 509 into the chamber 2200 also advances the top movable seal element 2210 downward through the resin compartment 2230 thereby advancing the resin downward. The bottom movable seal element 2220 is also advanced downward and, eventually, out of compartment 2230. Optionally, the top 2210 and/or the bottom 2220 movable seal elements may thereafter detach and fall into compartment 450. Movable seal element 2210 is advanced downward until all the resin and blood are forced out of the chamber 2230 and into the bottom portion 450 of the culture bottle allowing the blood and resin mixture (not shown) to be combined with the media 440 creating a blood, resin, and media mixture 570. The release of resin 300 can be timed and controlled automatically or manually.

In those embodiments where an additional reagent such as a lytic reagent are to be added to the culture bottle, an additional chamber or pouch can be placed either above or below the resin release assembly. For example, a pouch containing the additional reagent (e.g., a lytic reagent (not shown)) may be attached to the top or bottom movable seal elements 2210, 2220. Advancing the top and bottom movable elements by way of the needle 509 will puncture the pouch and release its content into the media 440 along with the resin. In preferred embodiments the reagent is a lytic reagent that is preferably concentrated saponin. In those embodiments where the media is a lytic media, the additional pouch containing the lytic reagent is optional.

FIGS. 27A-D illustrate an alternative embodiment of the invention having a different resin and/or lytic reagent release assembly. A molded insert 2720 is placed in a blood culture bottle 400. The insert 2720 has a body portion 2721 (FIG. 27C) that is a tubular-shaped chamber for housing reagents and a top portion 2722 that is adjacent to the septum/cap assembly 2700 and secures insert 2720 to the neck of the culture bottle. Chamber 2721 houses blood culture reagents, e.g., resin and/or lytic media, that are deliverable into the culture bottle for combination with culture media and other reagents. The top portion 2722 is wider in diameter than the body 2721 and the neck of the culture bottle 400.

A septum/cap assembly 2700 is situated above the narrow upper chamber 420 of the blood culture bottle 400 (FIGS. 27A-B). The cap assembly 2700 has a cap 200 for securing a septum 2710 and the molded insert 2720 to the neck of the culture bottle 400. A membrane 2730 seals the insert 2720 at the top and prevents reagents disposed inside the chamber from flowing through the openings 2740 and into the culture bottle 400. Preferably, the membrane 2730 is made of material that can be easily pierced or shattered by a needle 509. Suitable materials for the membrane include glass and molded polymers, which may be optionally filled with carbon or glass. The molded insert 2720 is suspended in the culture bottle 400 from the neck and secured to the culture bottle by the septum/cap assembly 2700.

The wider top portion 2722 of the insert 2720 contains the openings 2740 that are in fluid communication with the culture bottle 400 (FIG. 27A). The size and the shape (e.g., circles, diamond shape, triangle, etc.) of openings 2740 may be designed to accommodate various blood and liquid flow rates. The blood sample is introduced into the culture bottle by way of a needle which pierces the cap 200 and breaks the membrane 2730. As such, blood introduced into the insert 2720 will flow from the insert into the culture bottle through the openings 2740. Once the seal membrane 2730 is ruptured, the contents of the insert (e.g., the resin and/or lytic media) will also flow through the openings into the lower chamber 410 of the culture bottle 400 when the bottle/insert assembly is inverted.

Figure 27C:
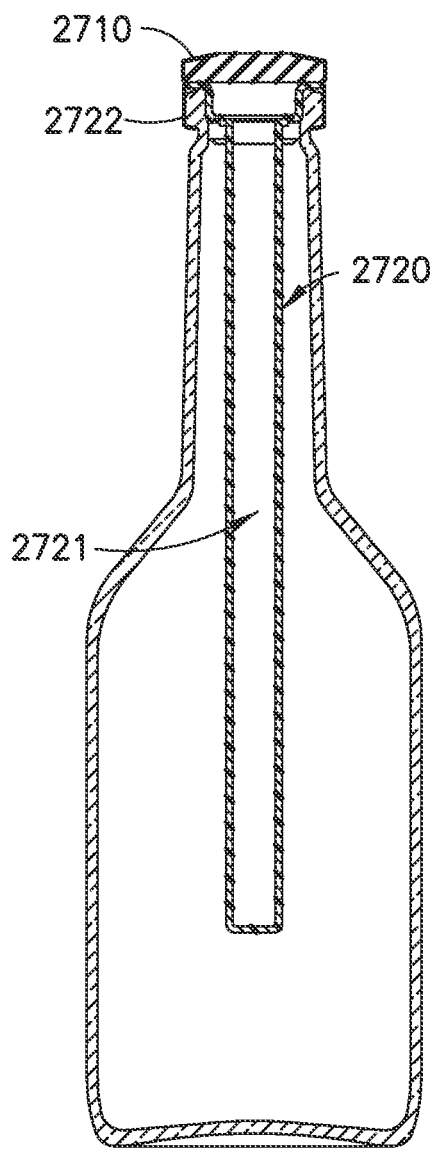
Figure 27D:
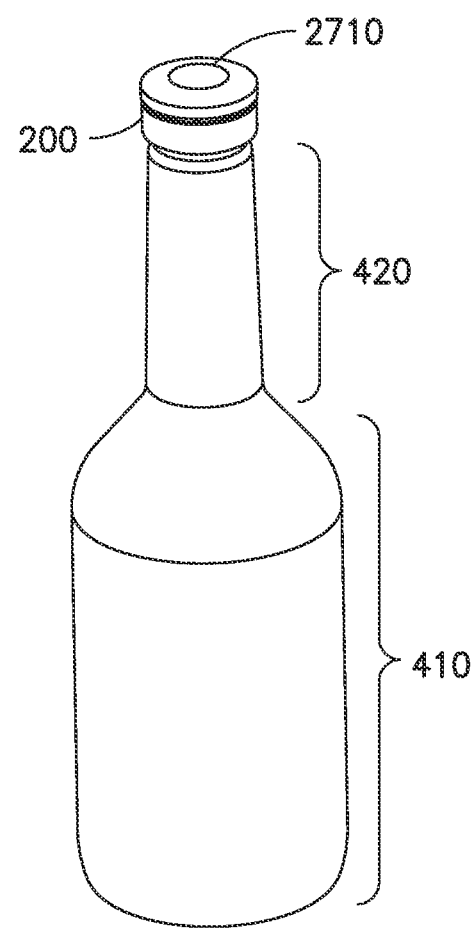

The molded insert 2720 isolates the reagents (e.g., resin 300) from the media 440 disposed in the bottom chamber 410 of the culture bottle 400 (the bottom chamber 410 filled with media 440 is 450 (not shown)) (FIGS. 27C-D). The diameter D1 of the tubular-shaped chamber 2721 may vary (FIG. 27D). In an exemplary embodiment, the chamber 2721 can hold up to about 2 ml of reagents. In alternative embodiments, the diameter D1 may be wider to hold larger volumes of liquid reagents.

In operation, a blood sample is first delivered into culture bottle 400 through a needle 509 (not shown) that penetrates the septum 2710 housed in the cap assembly 2700 and pierces (or shatters) the breakable membrane 2730. The needle 509 is advanced through the membrane 2730 to allow the blood to flow into the lower chamber 410 through the openings 2740 and bypass the chamber 2722 of the insert 2720. After the needle 509 is retrieved, the culture bottle/insert assembly is inverted several times to allow the reagents inside the insert 2720 to flow out and into the lower chamber 410 where the blood is mixed with pre-filled reagents and other media components present in the lower chamber 410. Because septum 2710 is preferably a re-sealable element, the contents of the culture bottle/insert assembly will not leak out during inversion. The blood, reagents from the insert and pre-filled culture bottle content (e.g., culture media) can also be mixed in the downstream processing steps when the culture bottle/inert assembly is placed into an agitation system in a BACTEC instrument and subjected to oscillation. The introduction of blood and resin/lytic media release mechanisms from the chamber 2721 of the molded insert 2720 can be timed and controlled automatically or manually.

Figure 28C:
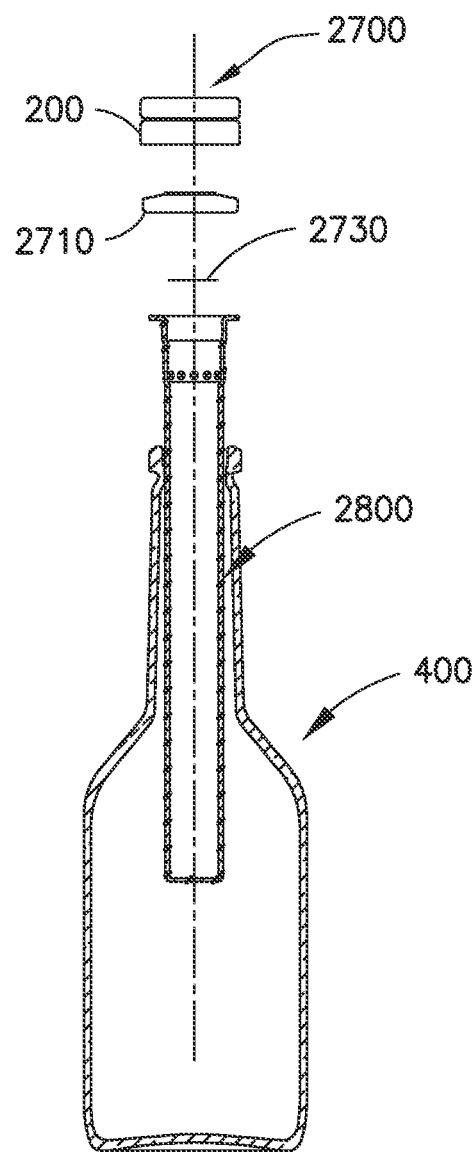
Figure 28D:
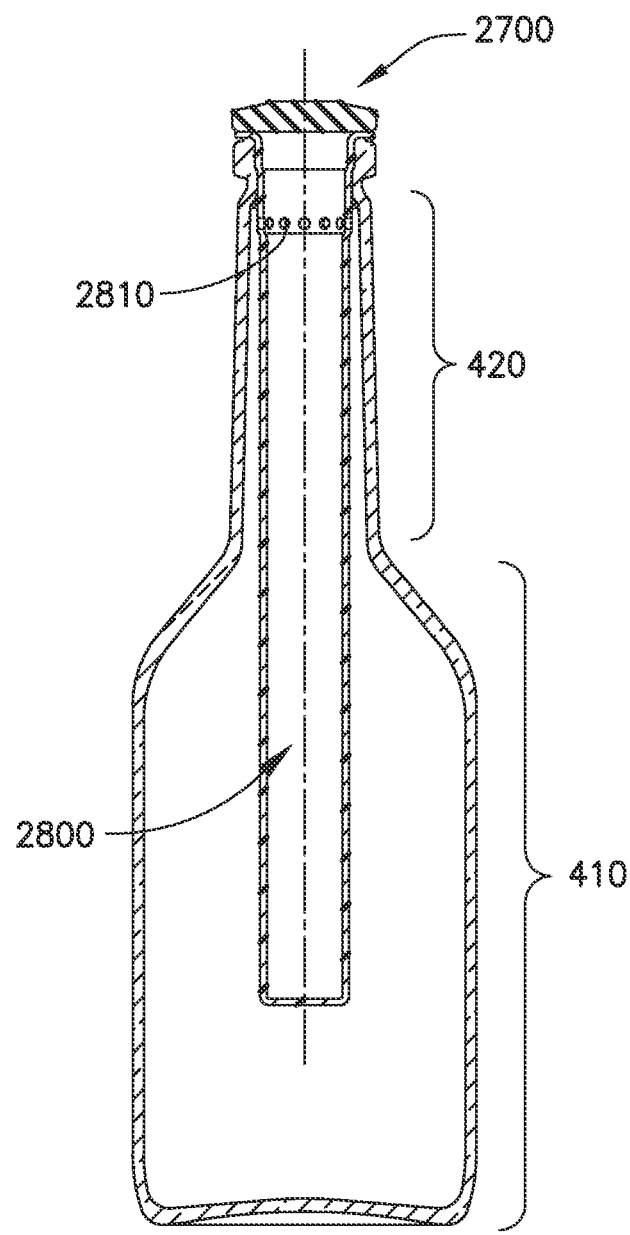

FIGS. 28A-D illustrate an alternative embodiment of the invention having a molded insert with a tubular-shaped chamber for housing resin and/or lytic media. The insert 2800 has an elongated body 2801 for placement into the culture bottle 400 and a lip 2802 that is designed to fit securely to the neck of the culture bottle 400 (FIGS. 28B, 28D). The body 2801 is a tubular-shaped chamber for holding reagents. The septum/cap assembly 2700 is situated above the narrow upper chamber 420 of the blood culture bottle 400. The cap assembly 2700 has a cap 200 for securing a septum 2710 and the molded insert 2720 to the neck of the culture bottle 400 (FIGS. 27A-B).

The insert 2800 contains openings 2810 near the top that permit fluid communication between the interior of the insert and the blood culture bottle. The blood sample is introduced into the culture bottle 400 through a needle 509 (not shown), where the needle penetrates the membrane 2730 to allow blood to flow into the culture bottle 400 and bypass the insert 2800. The membrane seal 2730 is disposed below the openings 2810 that, when broken, places the contents of the insert 2800 in fluid communication with the contents of the culture bottle 400 if the bottle/insert assembly is inverted or tilted to facilitate intermixing of the contents of the insert with the contents of the culture bottle.

The openings 2810 may be designed of various sizes and shapes to accommodate the blood and/or resin/lytic media volume and flow. The diameter D2 may vary to accommodate larger reagent volumes (FIG. 28A). In an exemplary embodiment, diameter D2 is sized to permit the molded insert to hold up to about 5 ml of liquid. The length of the insert may also vary for use with various culture bottles. The configuration and size of the culture bottle 400 may also vary to accommodate an insert 2800 of larger or smaller diameters.

Figure 29A:
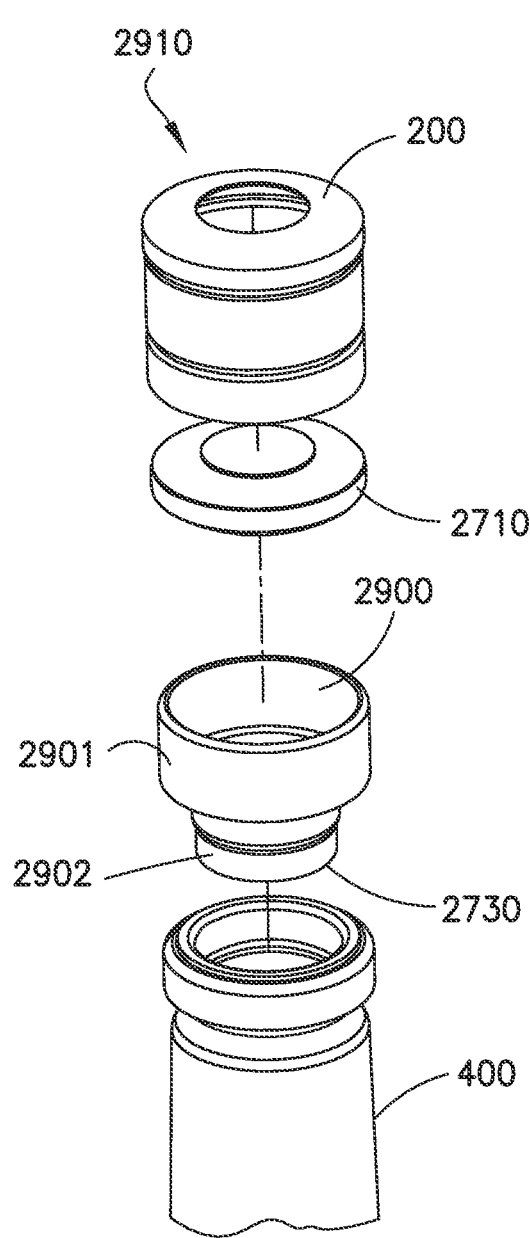
FIGS. 29A-D illustrate an alternative embodiment of the molded insert configured as a stopper that is partially suspended from the neck of the culture bottle in a perspective view (FIGS. 29A and 29D) and in a cut away side view (FIGS. 29B and 29C).
Figure 29B:
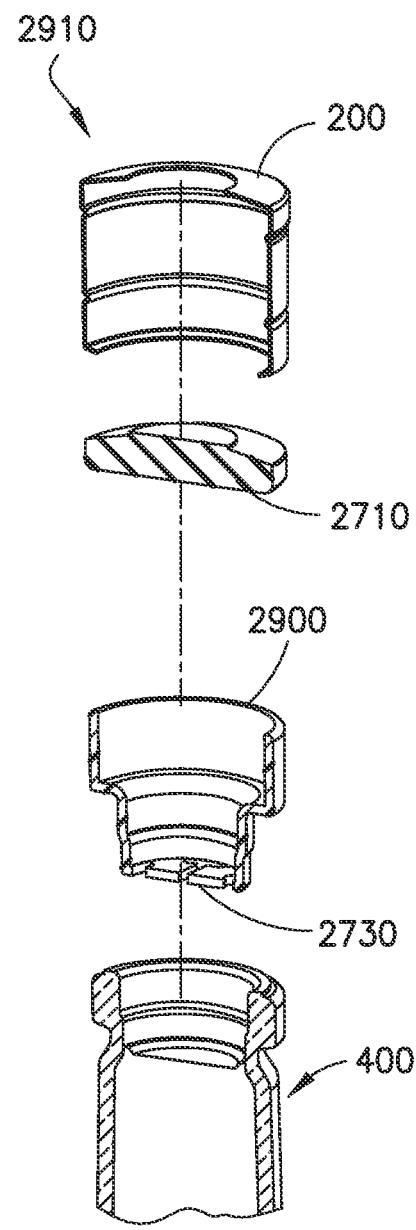
Figures 29C, 29D:
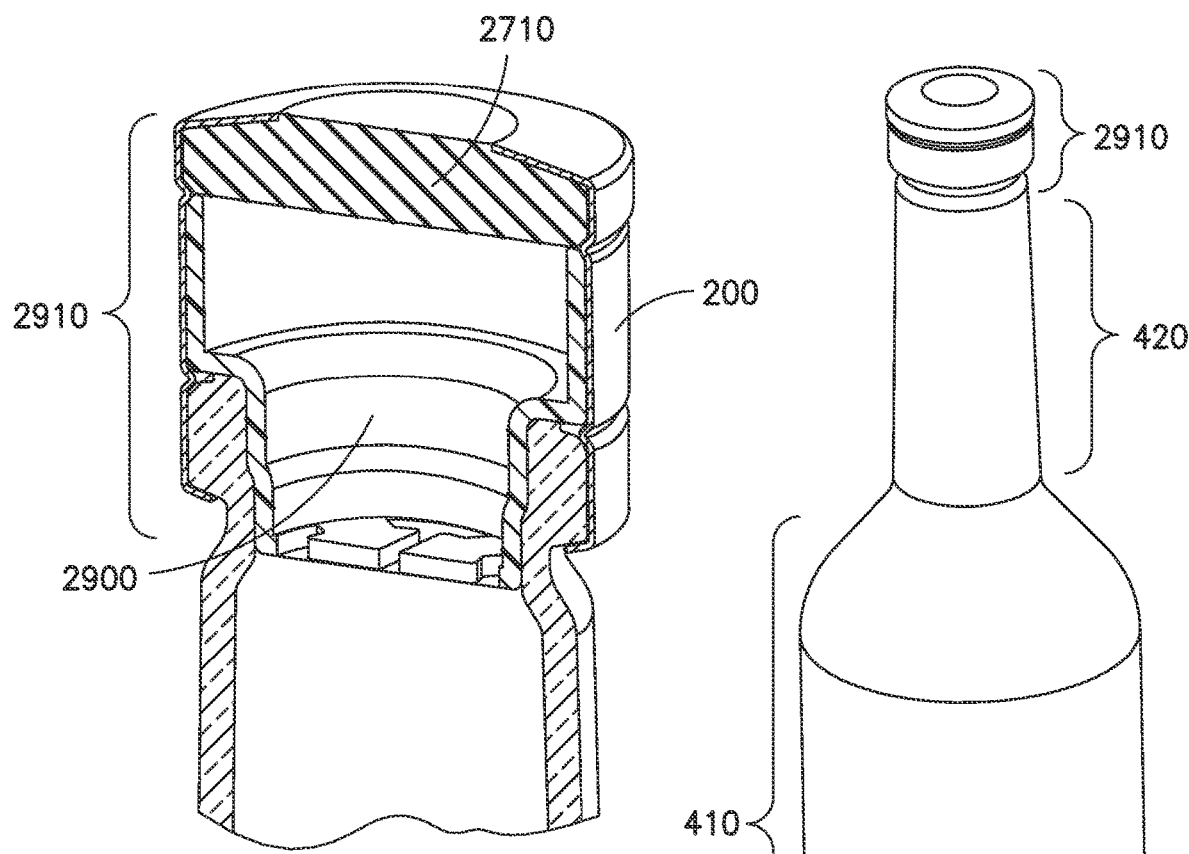

FIGS. 29A-D illustrate an alternative embodiment of the invention. The insert is configured as a stopper 2900 for housing a resin 300 and/or a lysis reagent 1601 (not shown). The stopper has a head portion 2901, a hollow body portion 2902, and a base portion 2730 (FIG. 29A). The hollow body portion 2902 is the chamber that contains the compositions/reagents to be combined with the blood and blood culture media, e.g., resin and/or lytic media. The insert 2900 is placed inside the narrow upper chamber 420 of the culture bottle 400 and secured to the bottle by a septum/cap assembly 2910 (FIGS. 29C-D) that covers the head portion 2901 of the insert 2900 and fastens the insert to the neck of the culture bottle. In this configuration, the cap 200 of the septum/cap assembly 2910 is large enough to cover the head portion 2901 of the stopper 2900 and to secure the stopper 2900 and the septum 2710 to the bottle 400. The large cap 200 and the septum 2710 are pierceable. Alternatively, the septum 2710 may be configured such that it becomes an extension of the head portion 2901 of the stopper 2900. The cap 200 may also be configured to be detached from the stopper 2900, for example, by pulling or twisting the cap before the septum 2710 is penetrated by way of a needle. The base portion of the stopper insert 2900 is the breakable membrane 2730 which seals the bottom of the insert and prevents the reagents from flowing into the bottle. The membrane 2730 can be of various shapes and configurations to facilitate tearing of the membrane. For example, the membrane 2730 can be designed in a shape of an arrow, diamond or a circle with optional serrated edges. The pierceable septum/cap assembly 2910 allows the needle 509 to advance through the septum 2710, into the stopper insert 2900 and break the membrane 2730. Advancement of the needle 509 tears or breaks the base membrane 2730 thereby allowing the blood sample and the contents of the insert to flow into the lower chamber 410 of the bottle 400 and mix with the contents already in the bottle. Alternatively, after the needle 509 is retrieved, the bottle/septum assembly may be inverted to allow the reagents to flow from the insert into the lower chamber 410 and mix with the blood and additional reagents, e.g., culture media 440 disposed inside the lower chamber 410 (not shown). In an exemplary embodiment, the stopper insert 2900 houses up to 1 ml of reagents.

Figures 30A, 30B:
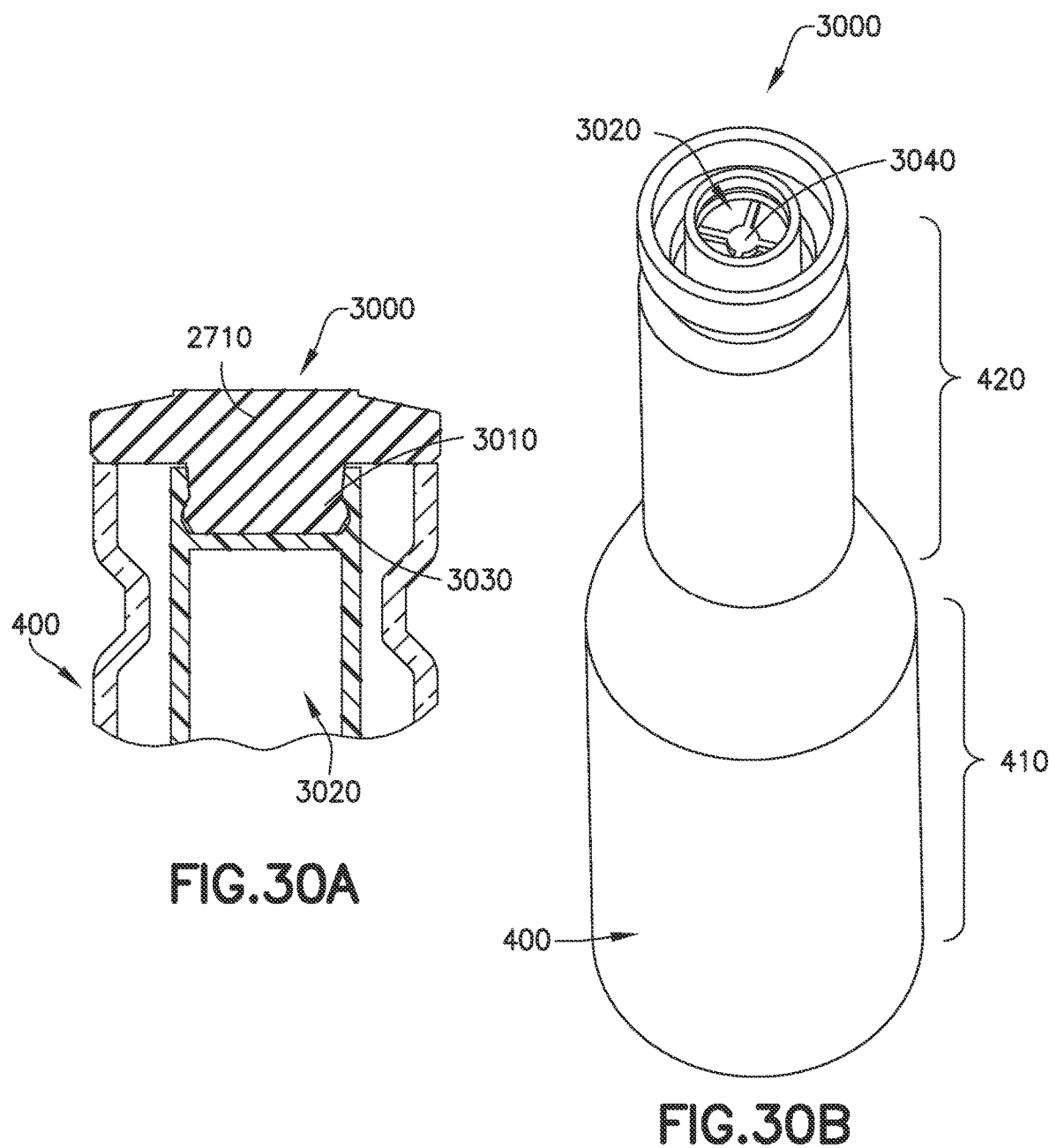
FIGS. 30A-C illustrate an alternative embodiment of the molded insert secured to the culture bottle by a septum/cap assembly in a cut away side view (FIGS. 30A and 30C) and a prospective top view (FIG. 30B).
Figure 30C:
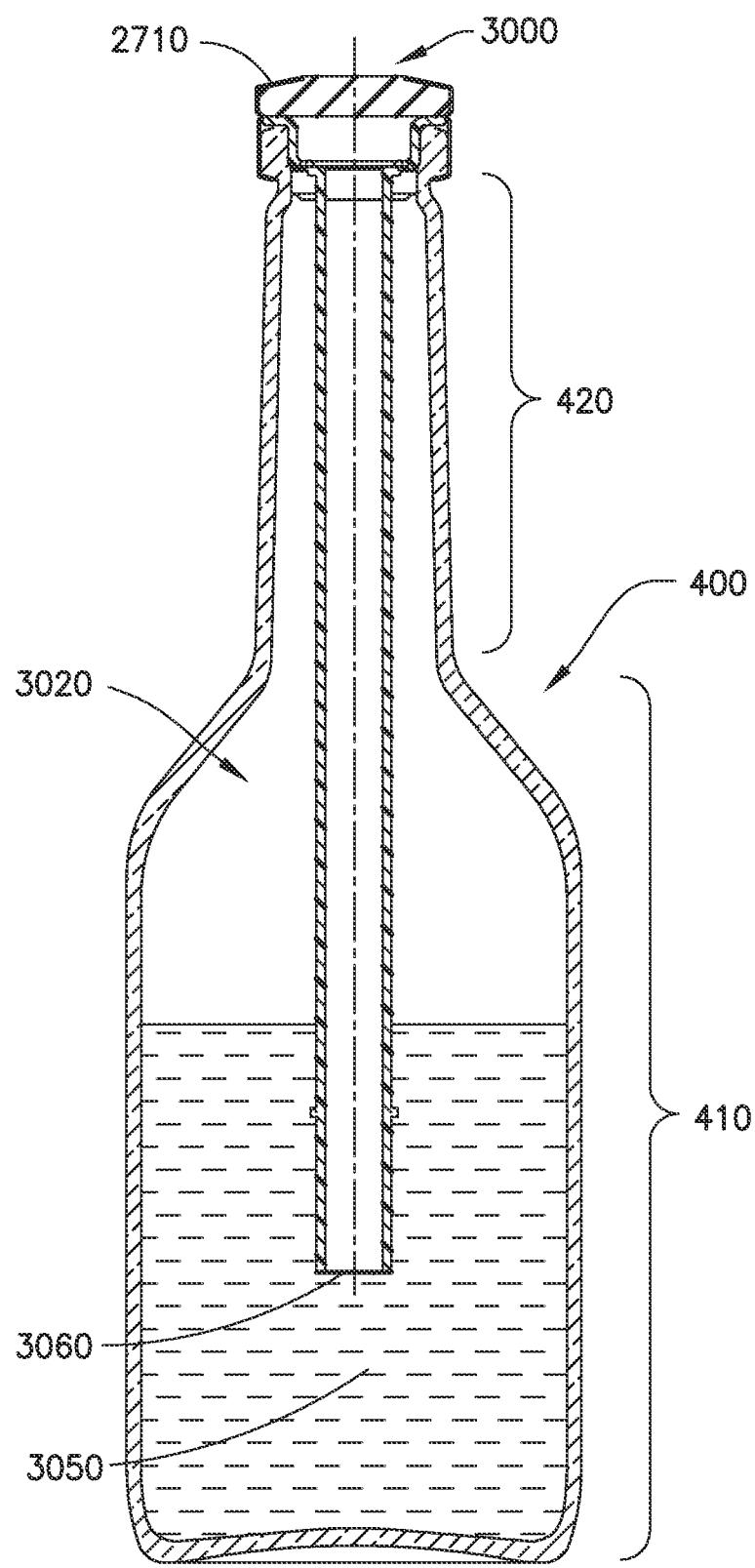

FIGS. 30A-C illustrate an alternative embodiment of the molded insert. The insert 3020 is configured to be received through the neck of the culture bottle 400 and contains a chamber for housing resin 300 and/or lytic reagent 1601 (not shown). The insert 3020 is secured to the culture bottle 400 by an assembly 3000. The assembly contains a septum 2710 that has a top wider diameter that will allow the septum to rest on the top of the culture bottle neck. The bottom portion 3010 of the septum 2710 is convex and is secured in a concave portion 3030 of the insert 3020, allowing the insert to be suspended in the culture bottle but secured to the neck by the septum. This configuration secures the insert 3020 inside the bottle without the need for a cap assembly. The top of the septum 2710 sits parallel to the neck of the narrow upper chamber 420 (shown as a dash line in FIG. 30A) to provide an airtight seal.

Beneath the septum 2710 and the upper portion of the insert 3020 is a barrier 3040 (FIG. 30B) that defines a chamber. The blood is delivered by way of a needle 509 through the septum 2710. Advancement of the needle 509 pushes the barrier 3040 and dislodges the tube 3020 into the bottle 400. The bottom portion 3060 of the insert is sealed. The action of the needle 509 (not shown) causes the insert 3020 to disengage and fall into the lower chamber 410 of the culture bottle 400. This facilitates the intermixing of the contents of the insert 3020 with the contents 3050 of the culture bottle 400 (FIG. 30C). The bottle/insert assembly can then be inverted several times to allow the reagents to flow out of insert and into the lower portion of the culture bottle 410 and mix with the content therein.

Figure 31:
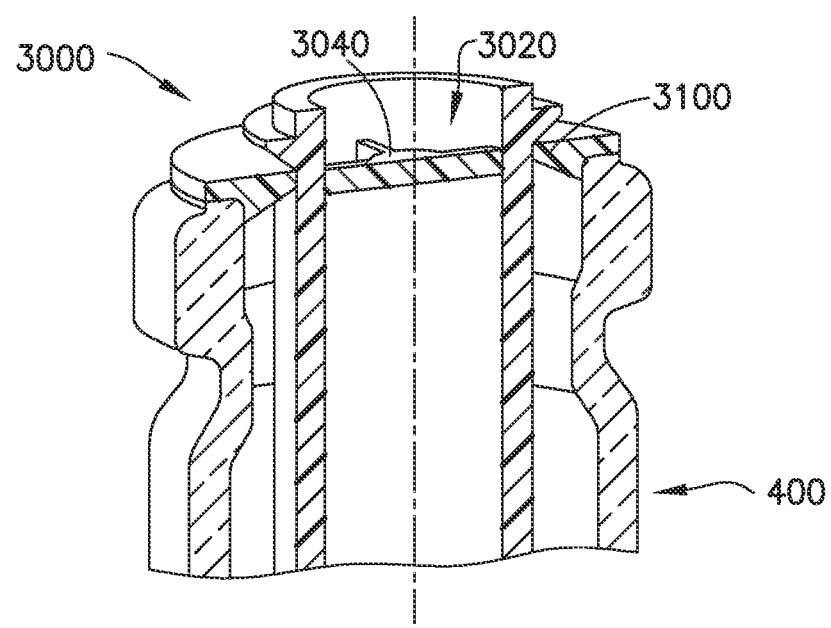
FIG. 31 is a cut away side view of a molded insert secured to the neck of the blood culture bottle by a flange.

In another embodiment, the septum 2710 can be replaced with a flange 3100 as shown in FIG. 31. In an exemplary embodiment, flange 3100 is elastomeric and has a bottom surface that is angled to help seal the bottle once vacuum pressure is applied to the system. In this configuration, advancement of the needle 509 through the barrier 3040 dislodges the molded insert 3020 from the flange into the lower chamber 410 of the culture bottle 400.

FIGS. 33A-B illustrate an alternative embodiment of the insert with a resin and/or a lytic reagent release mechanism. The insert 3300 (FIG. 33A) is received through and fastened on the neck of the blood culture bottle 400 (FIG. 33B). The insert 3300 includes an inner chamber 2720 for housing the resin or lytic reagent. A septum 2710 is placed on top of the insert assembly 3300. A cap 200 covers the septum 2710 and secures the insert 3300 to the culture bottle 400. The portion of the insert that extends into the blood culture bottle has a raised central portion 3310 that forms a tube in the bottom portion of the insert. The tube of raised central portion 3310 does not house additional reagents. The top of this tube has a seal 3320 for keeping the contents of the chamber from flowing into the culture bottle. A needle 509 is advanced through the septum 2710 and towards the seal 3320. The force exerted by the needle 509 breaks seal 3320 of the raised central portion 3310 to allow blood to flow into the bottom chamber 410 (not shown). That is, when the bottle 400 is inoculated with blood delivered by syringe, the needle disrupts seal 3320 to allow the blood to flow through the tube of raised central portion 3310 and into the culture bottle 400. The blood is then intermixed with the contents of the insert and the media 440 disposed in the bottom chamber 410 of the culture bottle 400 (the bottom chamber 410 filled with media 440 is 450). After the needle 509 is retrieved, the insert/bottle assembly may optionally be inverted to allow the reagents inside the insert to empty into the lower chamber 450 and mix with the blood/media mixture. The insert/bottle assembly may be inverted as needed to thoroughly mix the content therein. In an exemplary embodiment, the insert 2720 and the raised central portion 3310 may be made of uniform material. Alternatively, the edge of the bottom of the central portion 3310 may be made of a thinner material such that advancement of the needle 509 through the central portion 3310 breaks off and separates the raised central portion 3310 from the insert 2720. In this configuration, the blood and reagents from the insert flow directly into the bottom chamber 410 without the need to invert the bottle/insert configuration.

FIGS. 34A-B illustrate an alternative embodiment of the insert according to the invention. The insert 3400 is a septum cage that is placed inside the upper chamber 420 of a culture bottle 400. The cage can hold one or more capsules or ampoules 3410 having a resin 300 (not shown) and/or other materials that may be suitable for a particular use (e.g., lysis reagent) (FIG. 34A). The needle 509 used to inoculate the blood culture is advanced through the septum 3440 along the longitudinal axis of inert 3400 (FIG. 34B) and into the capsule 3410. Advancement of the needle 509 disrupts the capsule 3410 and releases the capsule content (not shown) into bottom chamber 410 which may be pre-filled with culture media 440. The disrupted capsule and the reagents are released through the openings of the septum cage 3420 while the cage remains intact. The blood delivered through the needle 509 is mixed with the content of the culture bottle and the capsule 3410. The capsules are not soluble in the contents of the blood culture bottle. A suitable material for the capsule includes water insoluble materials that are capable of being disrupted by a needle. In an exemplary embodiment, the capsule material may be made of DuPont™ Surlyn® film. The septum cage may be made of elastomeric or other flexible materials to allow for easy insertion of the capsule during the manufacturing assembly. Examples of such materials include DuPont™ Surlyn® film and Saran™ plastic.

Figure 35:
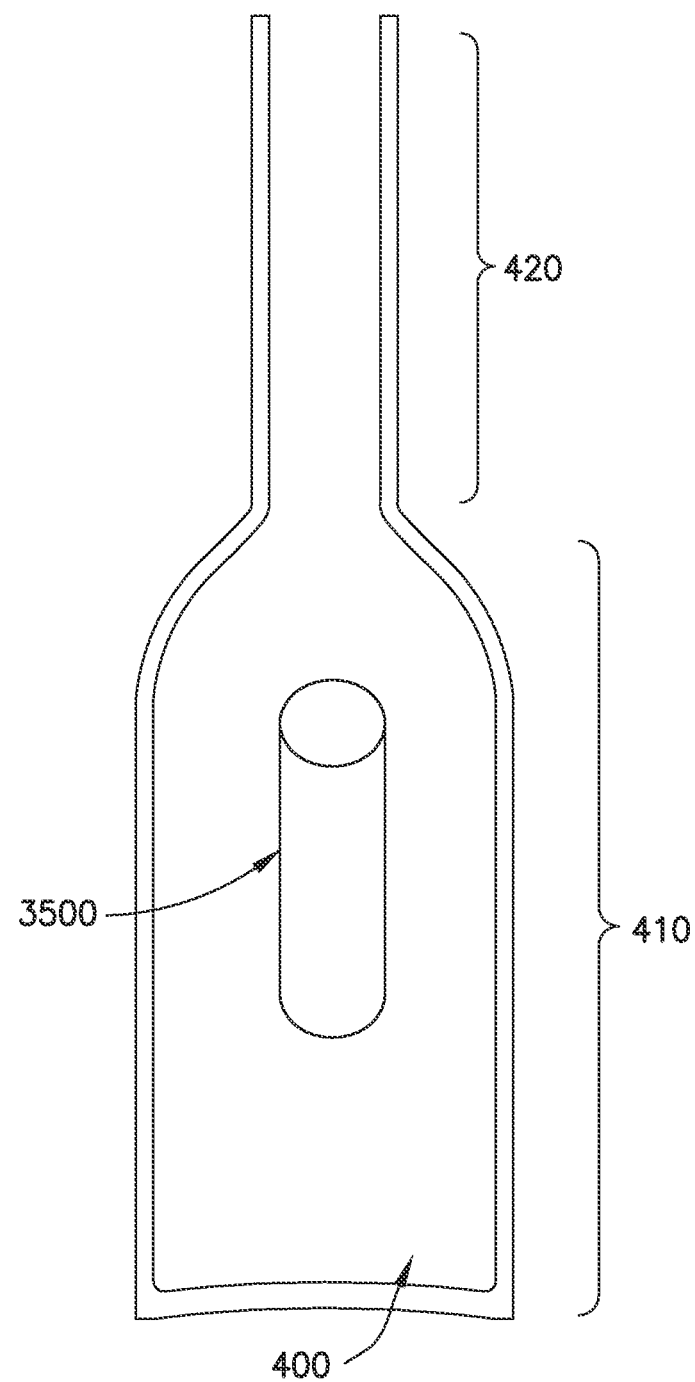
FIG. 35 is a cut away side view of the culture bottle with a suspended insert.

In the embodiments described above, the insert may be secured to the neck of the bottle or be suspended inside the culture bottle as shown in FIG. 34B. In FIG. 35, the insert 3500 is suspended inside a culture bottle 400 using any variety of conventional mechanisms well known to those skilled in the art so that it is easily disrupted. For example, the insert may be fully or partially disrupted or agitated inside the culture bottle by an external force (e.g., centrifugal, sonic, magnetic force, etc.) in order to release the content therein. The type of an external force used to agitate the insert may depend upon the insert/bottle assembly and configuration. Examples of agitation include mechanical, thermal and pressure agitations. In the embodiments where the insert is suspended inside the culture bottle unsecured, the chamber may be disrupted either before or after the blood is introduced into the culture bottle. For example, the blood can first be introduced into the chamber/bottle assembly to mix with the pre-filled media inside the bottle and incubated without disrupting the chamber to release the contents therein. Alternatively, the blood can be introduced into the culture bottle inside a container (e.g., tube) to prevent the blood from mixing with the contents of the culture bottle (e.g., pre-filled media). In these embodiments, the chamber may be disrupted by an external force to release the reagents before the blood is introduced into the culture bottle allowing the released reagents to equilibrate with media before the blood is introduced.

FIGS. 36A-D illustrate an alternative embodiment of the invention. The insert 3620 (FIG. 36D) is a barrel 3610 with a plunger 3600 that is placed inside the upper chamber 420 of a culture bottle 400. The barrel 3610 has a hollow center.

Figure 36A:
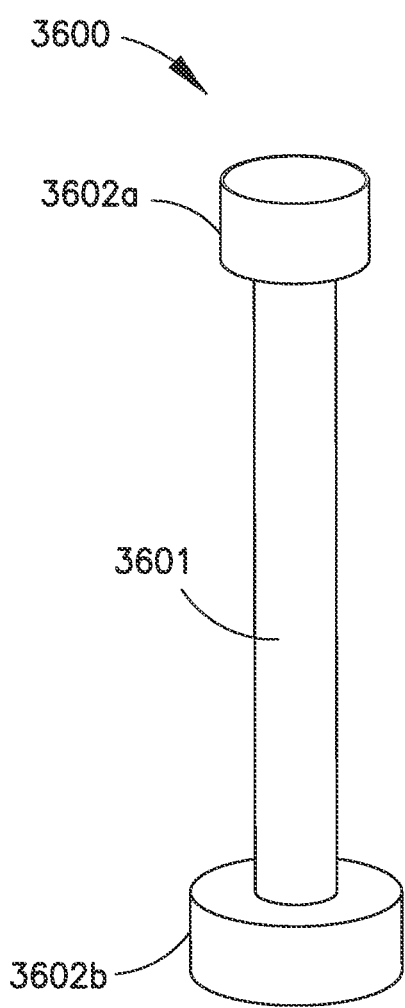
FIGS. 36A-D are cut away side views of an alternative embodiment of the insert where the chamber is a barrel with a plunger.
Figure 36B:
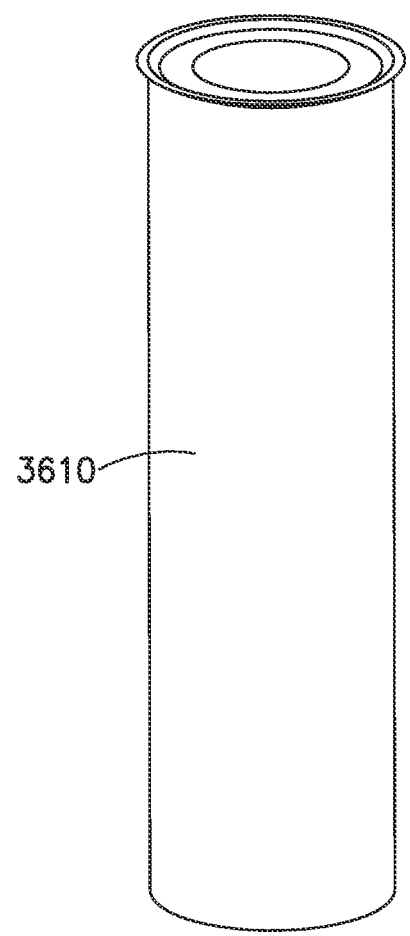
Figure 36C:
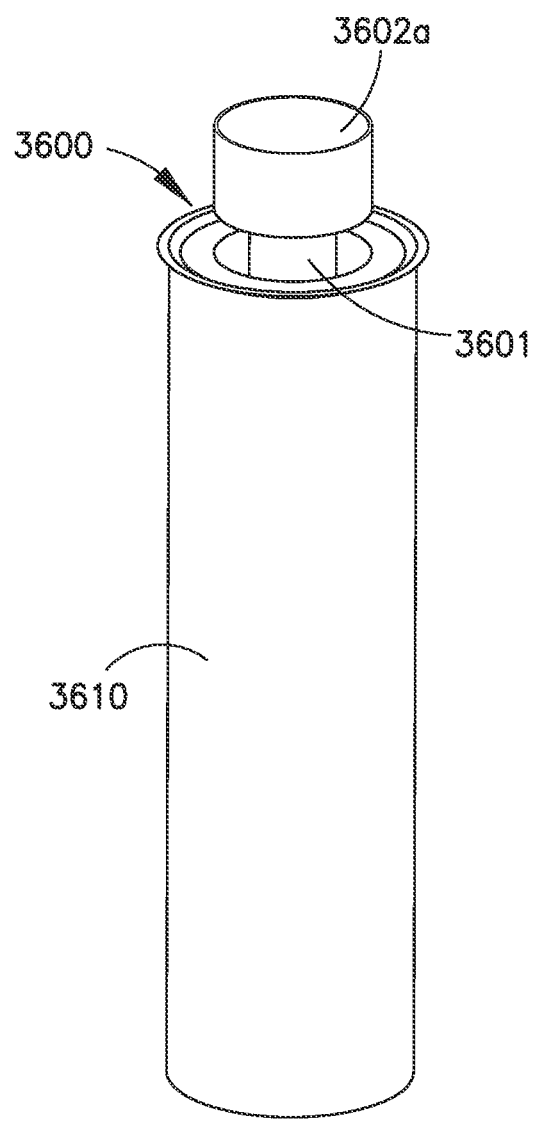
Figure 36D:
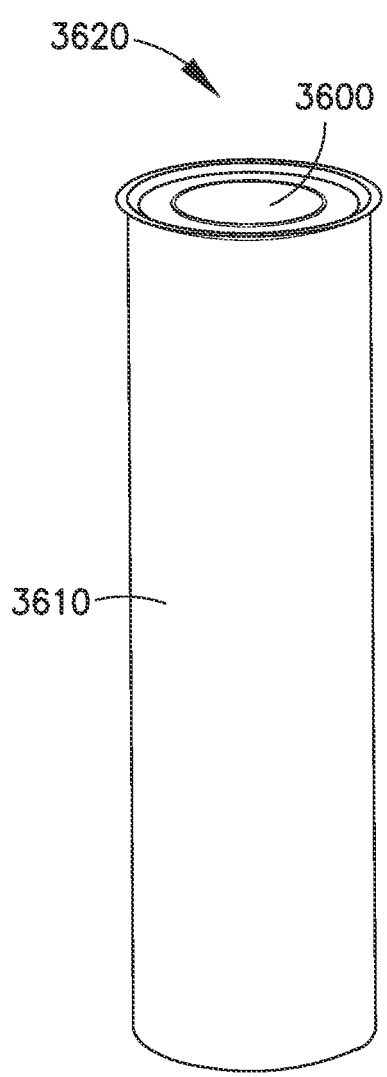
Figure 37A:
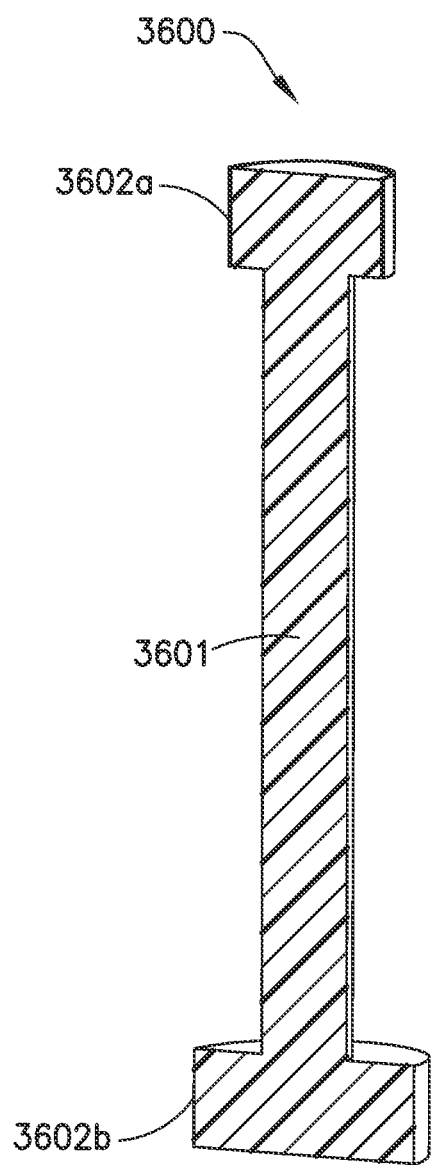
FIGS. 37A-F are perspective views of the assembly depicted in FIGS. 36A-D.
Figure 37B:
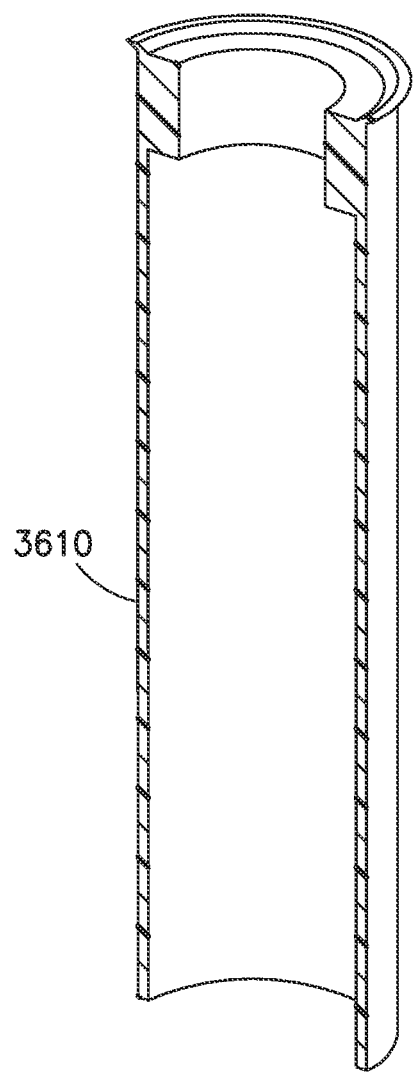
Figures 37C, 37D:
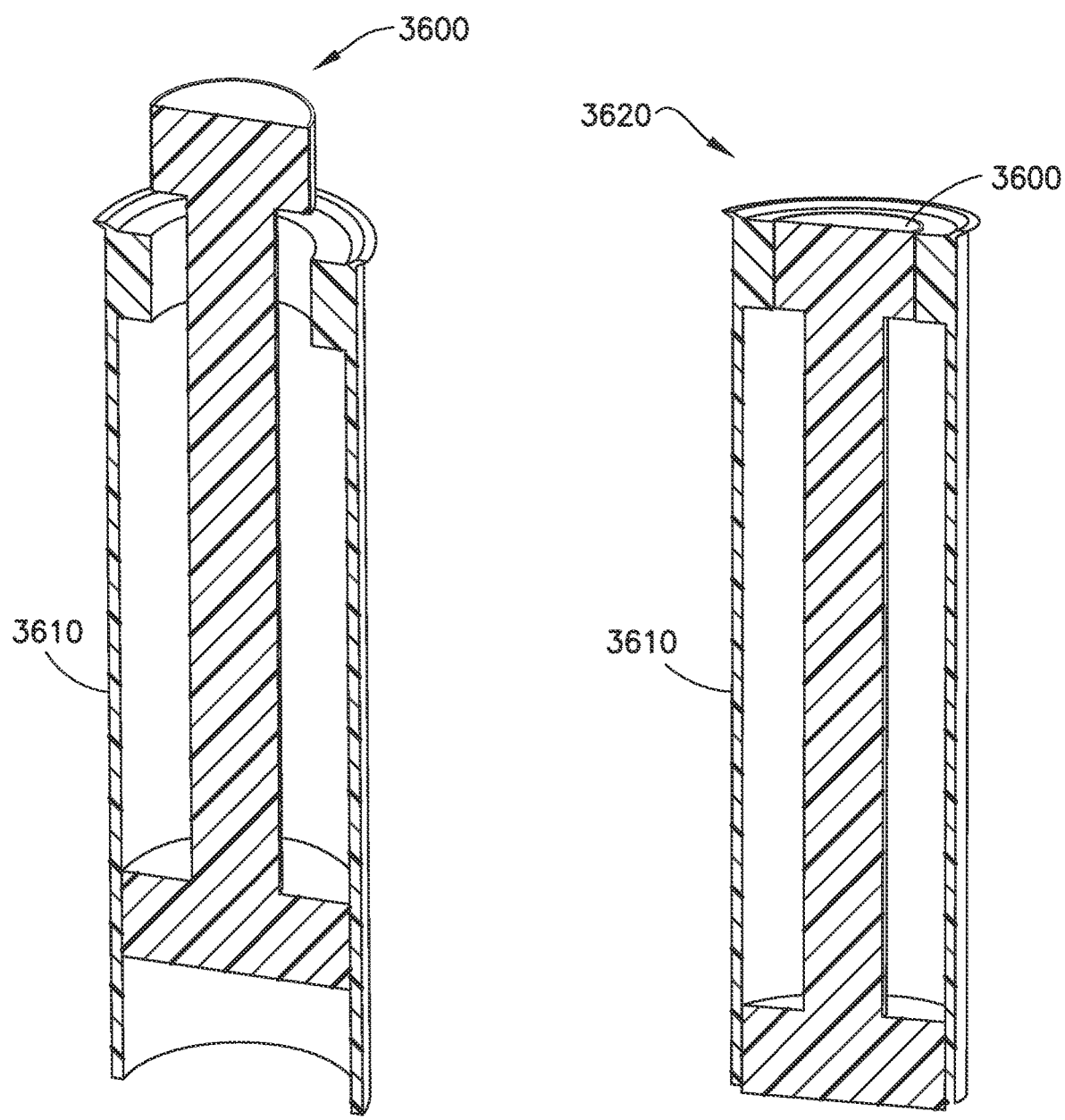
Figure 37E:
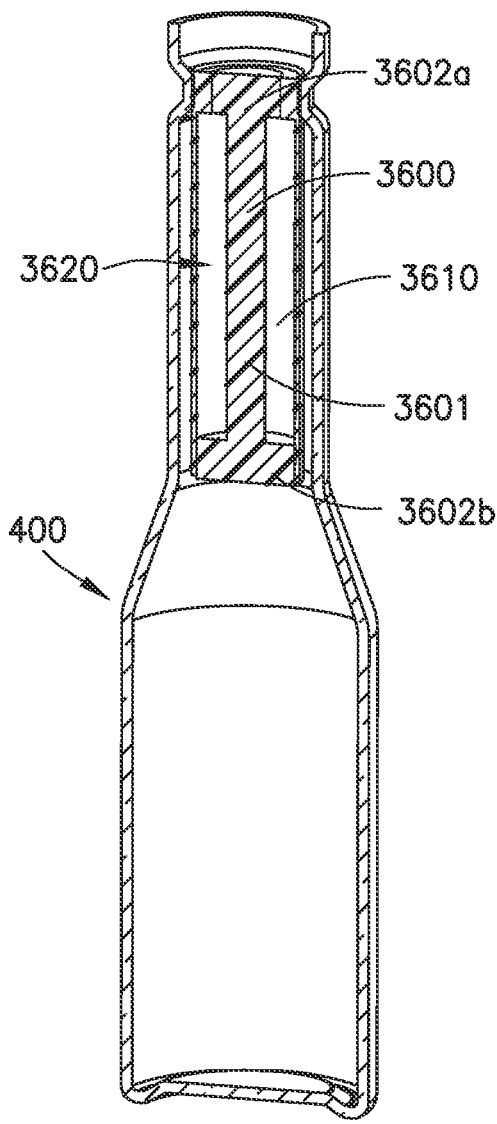
Figure 37F:
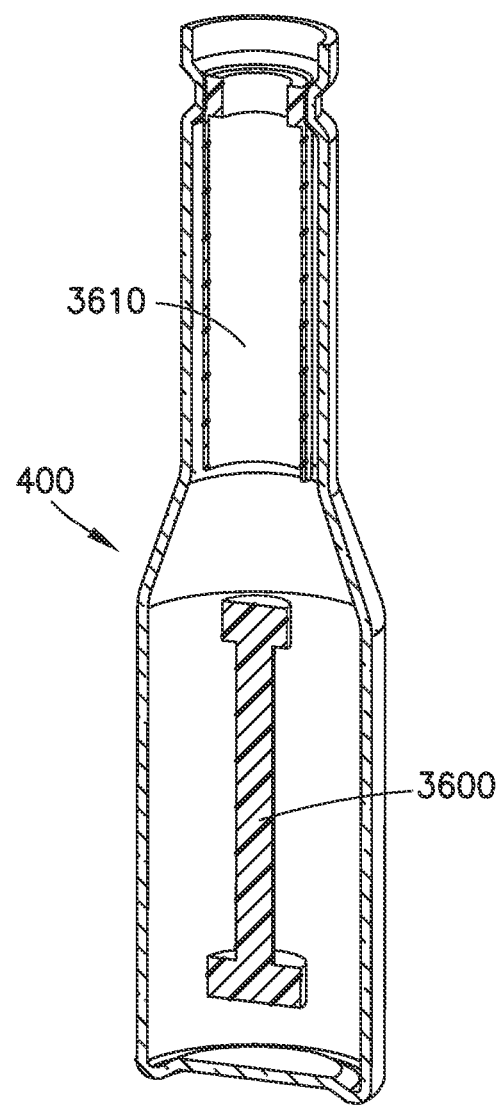

The plunger 3600 has an elongated tube 3601 having a top and a bottom circular portion 3602a and 3602b respectively. A resilient material, e.g., rubber, is wrapped around the circumference of the top and bottom portions to create a seal between the barrel 3610 and the plunger 3600 (FIG. 36A). In an exemplary embodiment, the plunger is made of an autoclavable plastic material. The plunger 3600 is first placed inside the barrel 3610 (FIG. 36C). The circumference of the bottom circular portion 3602b of the plunger is slightly larger than the top circular portion 3602a to securely fit inside the hollow bottom portion of the barrel and provide a tight seal. After the plunger 3600 is partially placed inside the barrel 3610 as shown in FIG. 36C, the barrel is filled with a liquid, e.g., resin or lytic media, and then sealed by plunger 3600. The sealed plunger/barrel assembly 3620 (FIG. 36D) is then placed inside a culture bottle 400 such that it is suspended from the neck of the bottle and secured in place with a cap 200. The blood is delivered into the culture bottle 400 by way of a needle 509 (not shown) used to inoculate the blood culture. The needle 509 is advanced through the cap 200 such that it touches the top portion 3602a of the plunger 3600. Advancement of the needle 509 pushes the top portion 3602a downward to displace the plunger 3600 and create an opening at the bottom of the barrel 3610 to release the barrel content (not shown) into the bottom chamber 410, which may be pre-filled with culture media as shown in FIGS. 37E-F. The blood delivered through the needle 509 is mixed with the content of the culture bottle and the barrel 3610. Views of the plunger and barrel configuration are shown in FIGS. 37A-D.

Figure 7A:
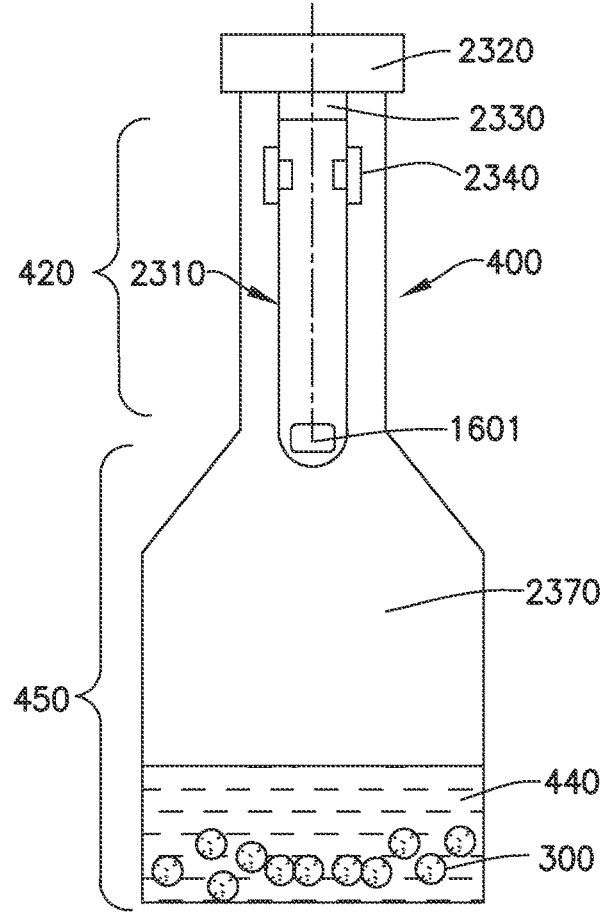
FIGS. 7A-B are cut away side views of a culture media bottle containing a vacuum chamber insert.
Figure 7B:
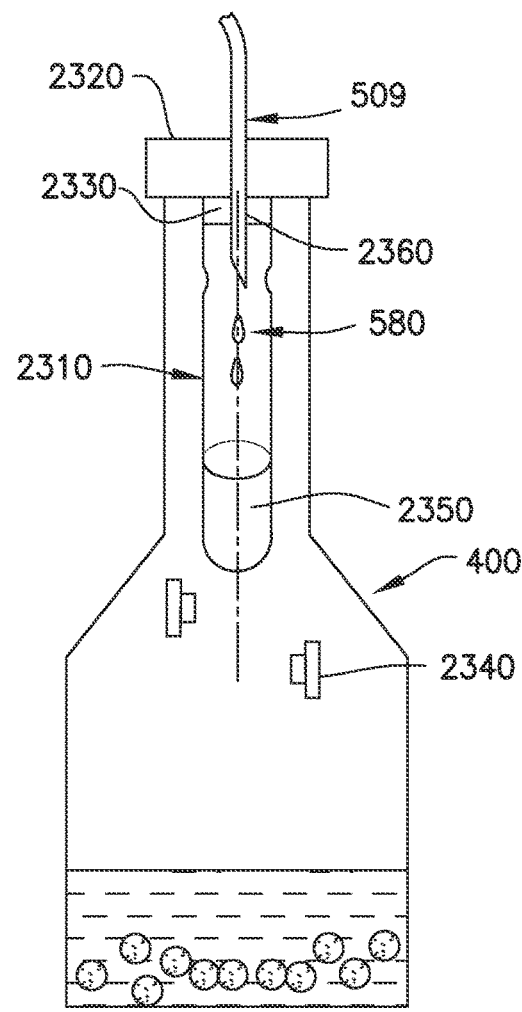

FIGS. 7A-B illustrate an alternative embodiment of the invention. The insert is a vacuum chamber 2310 containing a lysis reagent 1601. As used herein, the term "vacuum chamber" refers to a chamber having an internal pressure that is less than normal atmospheric pressure. The term "vacuum" means less than the normal atmospheric pressure as used herein. The vacuum sealed chamber 2310 is placed inside the top portion 420 of the culture bottle 400, which has an atmospheric pressure therein. By virtue of this configuration, the pressure within the vacuum chamber 2310 is less than the normal atmospheric pressure 2370 inside the lower chamber 450. The vacuum chamber 2310 has stoppers 2340 and a vacuum septum seal 2330. Although two stoppers 2340 are illustrated, the skilled person is aware that the number of stoppers is a matter of design choice. In an exemplary embodiment, the vacuum septum seal 2330 is made of a resilient material, e.g., rubber, which can be readily punctured by a needle or a syringe but still function as a vacuum seal. The culture bottle is first filled with culture media 440 and resin 300. Alternatively, the culture bottle may be filled with different reagents (FIG. 9B) depending upon the user's need. A cap 2320 is used to seal the top of the culture bottle 400 after inserting the vacuum chamber 2310 therein.

Figure 8:
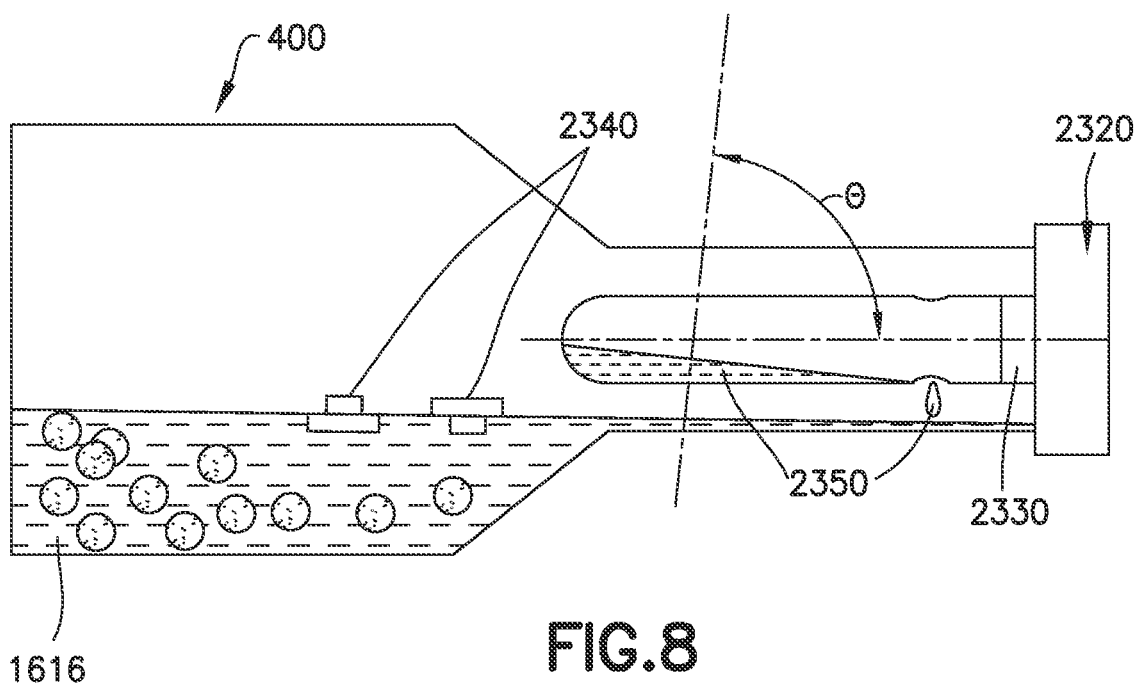
FIG. 8 is a cut away side view of a culture media bottle containing a vacuum chamber insert that is positioned horizontally.

Using a needle 509, a blood sample 580 is introduced into the vacuum chamber 2310 containing a lysis reagent 1601 to create a lysed blood mixture 2350 (FIG. 7B). The needle 509 punctures the cap 2320 and the vacuum septum seal 2330 creating a sample injection port 2360. The advancement of the needle 509 through the cap 2320 and vacuum seal 2330 causes the two vacuum stoppers 2340 to detach from the vacuum chamber 2310 by equalizing the pressure difference between the lower chamber 450 having a normal atmospheric pressure and the vacuum chamber 2310 having a pressure that is less than the normal atmospheric pressure. Detaching the stoppers leaves openings in the vacuum chamber 2310. After penetration and stopper release, the bottle/vacuum chamber assembly is then tilted or inverted to allow the lysed blood mixture 2350 (FIG. 8) to flow through the openings into the bottom chamber of the culture bottle pre-filled with resin 300 and culture media 440. Alternatively, the lysed blood mixture 2350 can be combined with the media and resin mixture 1616 by shaking or incubating the bottle/insert assembly. Apparatuses for shaking/incubating blood culture bottles are well known to those skilled in the art and are not described in detail herein. BACTEC™ instruments (commercially available from Becton Dickinson) are examples of such instruments. The blood culture bottle may have a sensor 430 disposed therein. Alternatively, the blood culture bottle may be attached to an external sensor such that the content of the culture bottle may be interrogated from the outside of the bottle.

Figure 9A:
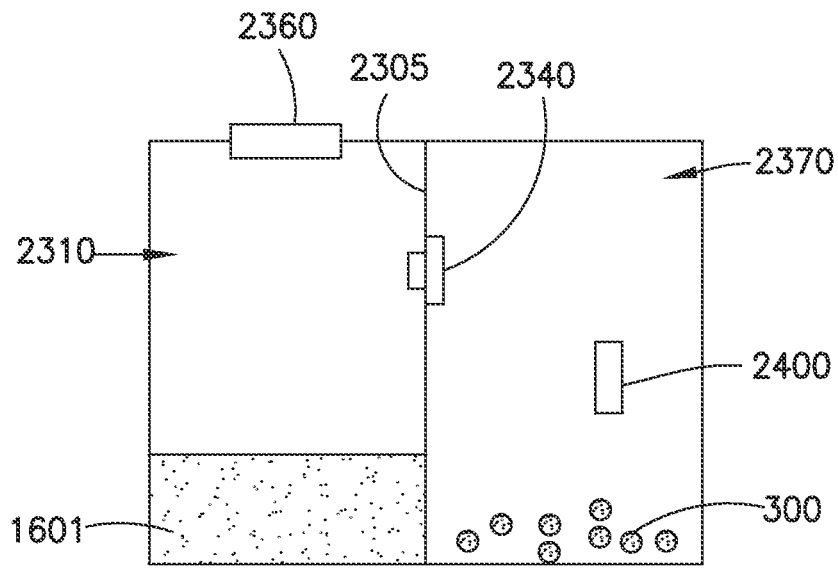
FIGS. 9A-B show schematic views of alternative embodiments of the vacuum chamber insert.
Figure 9B:
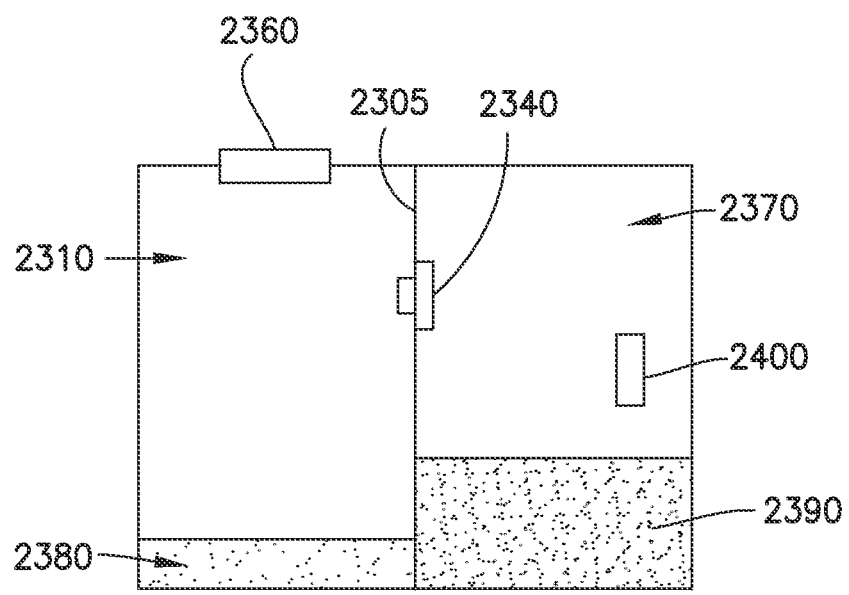

In FIGS. 9A-B, the vacuum chamber insert 2310 may include a second chamber 2370. The second chamber 2370 may have a normal atmospheric pressure. The configuration of the chambers depends upon the shape and size of the tubes, vessels, bottles, containers, etc. in which the chambers are configured. In the illustrated embodiment of FIGS. 9A-B, the vacuum chamber insert is represented schematically and does not reflect the true size/shape of the insert. A skilled person is aware that the specific configuration of the chamber inserts and how the inserts are integrated into the blood culture assembly is largely a matter of design choice. The compartments are separated by a divider 2305 with a vacuum stopper 2340 to retain pressure that is less than the atmospheric pressure in chamber 2310 until intermixing of the contents of chambers 2310 and 2370 is desired. In one embodiment, the vacuum chamber 2310 is filled with a lytic reagent 1601 and the second chamber 2370 is filled with resin 300 (FIG. 9A). In another embodiment, the vacuum chamber and the adjacent compartment may be filled with different reagents denoted as 2380 and 2390, respectively, in FIG. 9B. Second chamber 2370 has normal atmospheric pressure and has an access port 2400 from which the contents of the compartment 2370 are released or withdrawn.

The sample, e.g., blood (not shown), is received into the vacuum chamber 2310 through the sample injection port 2360 as described above. A needle or syringe can be used to advance the sample into the vacuum chamber 2310 to mix with the lytic reagent 1601. Advancement of the needle into the injection port 2360 causes the vacuum stopper 2340 to detach from the divider 2305. The device containing the two-compartment insert can then be inverted or tilted such that the content of the two chambers mix to create, for example, a blood, resin, lysing reagent and media mixture. Optionally, the sample may be advanced through the injection port 2360 either automatically or manually to create a reaction mixture (e.g., blood with lysis reagent), and cause the vacuum stopper 2340 to detach. Upon detachment of the stopper 2340, an opening is created which allows the reaction mixture from the vacuum chamber to flow into the second chamber 2370 and react with reagents therein. Alternatively, the sample may flow from the second chamber 2370 into the vacuum chamber 2310 creating a blood sample, resin, lysis reagent, and media mixture (not shown) in one of the two chambers.

Figure 32A:
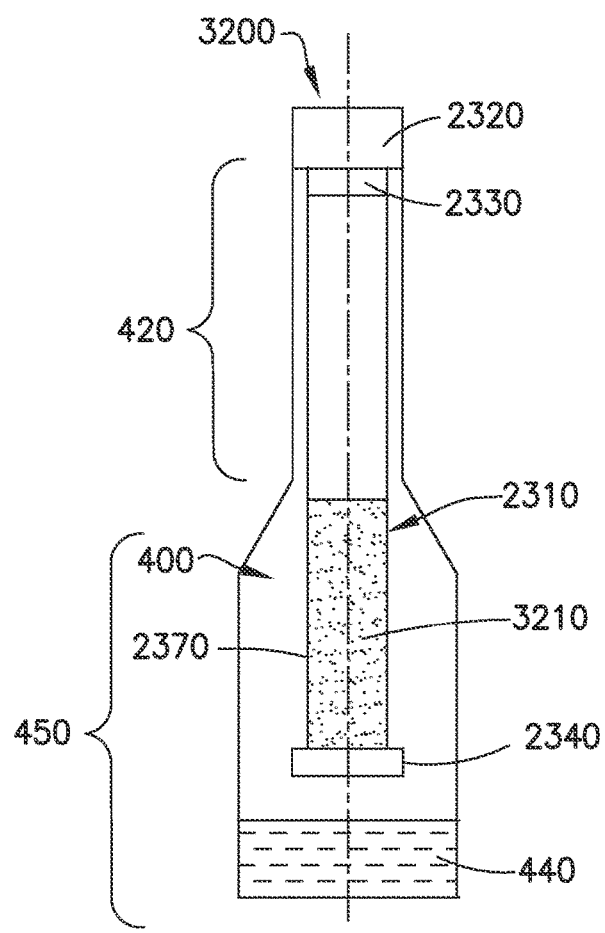
FIGS. 32A-B are cut away side views of a culture media bottle containing an alternative embodiment of the vacuum chamber insert.
Figure 32B:
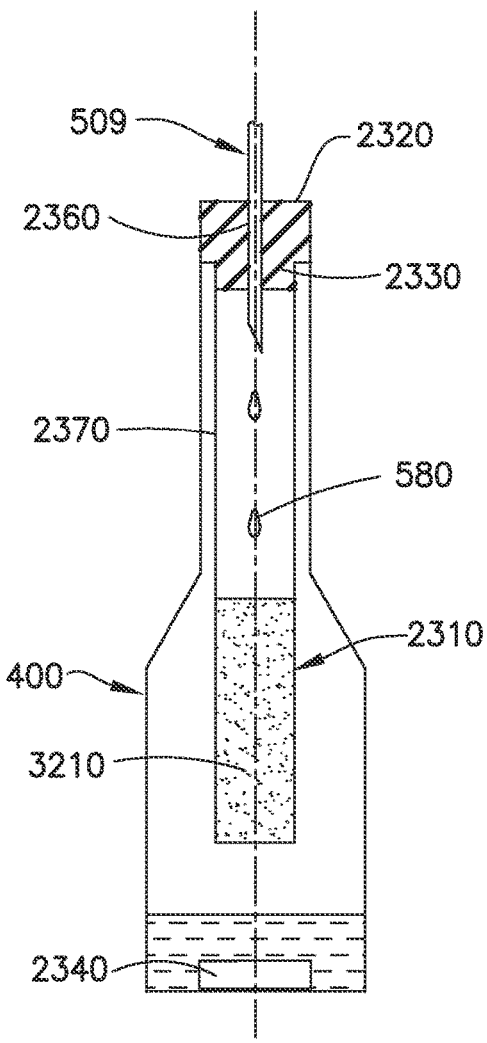

FIGS. 32A-B illustrates an alternative embodiment of the vacuum chamber insert 2310. The insert contains a resin column with media 3210. The vacuum insert 2310 is placed inside the upper chamber 420 and a portion of the lower chamber 410 of the culture bottle 400, the culture bottle having an atmospheric pressure therein. Vacuum chamber 2310 has a stopper 2340 and a vacuum septum seal 2330.

After the vacuum chamber 2310 is placed inside the bottle 400, a cap 2320 is used to secure the vacuum chamber 2310 therein. The pressure within the vacuum chamber 2310 is less than the normal atmospheric pressure 2370 inside the culture bottle 400. The pressure difference between the vacuum chamber 2310 and the culture bottle 400 holds chamber 2310 inside the bottle. In an exemplary embodiment, the vacuum septum seal 2330 and the stopper 2340 are made of a resilient material, e.g., rubber, which is readily punctured by a needle or a syringe yet still able to function as a vacuum seal. The culture bottle is first filled with culture media 440 (FIG. 32A). Alternatively, the culture bottle may be filled with different reagents.

Using a needle 509, a blood sample 580 is introduced into the vacuum chamber 2310 containing a resin column with media 3210 to absorb antibiotics that may be present in a blood culture (FIG. 32B). The needle 509 punctures the cap 2320 and the vacuum septum seal 2330 creating a sample injection port 2360. The advancement of the needle 509 through the cap 2320 and vacuum seal 2330 causes the vacuum stopper 2340 to detach from the vacuum chamber 2310 equalizing the pressure difference between the lower chamber 450 having a normal atmospheric pressure, and the vacuum chamber 2310 having a pressure that is less than the normal atmospheric pressure. Detaching bottom stopper 2340 leaves openings in the vacuum chamber 2310. After penetration and stopper release, the blood is passed through the resin column 3210 to mix with the culture media 440 in the prefilled lower chamber 410 (the mixture of blood with media is labeled as 450). In this embodiment, an upper portion of the resin column 3210 remains inside the vacuum chamber 2310 while a lower portion falls out of the vacuum chamber and into the lower chamber 410 of the culture bottle.

In the embodiments where the media is combined or is to be combined with a resin and another reagent (e.g., a lytic reagent), a plastic pouch can be used to house the lytic reagent. In one embodiment the chamber that holds the lytic reagent (not shown) is a plastic pouch attached to the bottom of the cap 200 (FIGS. 2A-D). The lytic reagent is preferably a concentrated saponin. However, other lytic reagents can also be used.

FIGS. 10A-B illustrates another embodiment of the invention with a different insert configuration. The embodiment of FIG. 10A has a cap assembly 760 with a cap 650 and a sensor 430 attached a bottle 800. A chamber insert 810 is inserted into bottle 800. Insert 810 has a sealed chamber for a sample component such as adsorption resin 300. Growth media 440 is placed in lower portion of bottle 800. A blood sample 580 is introduced through the cap 650. FIG. 10A also contains an optional safety lock 660 for use during storage. Other embodiments do not require the safety lock 660.

The FIG. 10A embodiments are also applicable where a lytic reagent is to be combined with the sample in the growth media. For example, it may be advantageous to house the lytic reagent in a separate pouch (not shown) that may be attached to the cap assembly 760. As the sample is introduced into the media, the lytic reagent is released into media 440 as well. In one embodiment, the lytic reagent is saponin. Preferably, the pouch is made of a plastic that can be easily punctured by way of a needle 509.

The operation of the cap 650 of FIGS. 10A-B, cap assembly 760, and a tapered rod 700 is illustrated in FIGS. 11A-B. Cap 650 has an outer housing 701 that contains internal screw threads 750 and has an apertures 740a and a aperture 740b. Apertures 740a, 740b allow insertion of the needle of a blood withdrawing device. The shape and size of the apertures can vary to allow access for different instruments and devices. Outer housing 701 also contains a pressure release gateway 730. Preferably, outer housing 701 is fitted over a septum liner 710. The septum liner 710 contains two recesses 711. Rod 700 has two separated parts: the rod body 700a; and a sharpened end 700b. At least one tab 712 is attached to rod body 700a and inserted into the needle penetrable liner 710. Each tab 712 are preferably received by recesses 711. A barrier 720 is advanced along the rod body 700a by way of an opening in the center of the barrier 720 either before or after the rod body 700a is assembled with the septum 710 and before the tapered portion guidance of the rod 700b is assembled with 700a. The placement of the tapered portion of the rod 700b in relation to the rod body 700a may vary such as the tapered portion 700b is positioned off-center (FIG. 10B) with respect to the cap assembly. Barrier 720 can be placed anywhere on the rod body 700a. After the barrier 720 is advanced to its location on the rod body 700a (either before or after the rod body 700a is attached to the needle penetrable liner 710), the tapered portion 700b is attached to the rod body 700a. Once all parts are configured (FIG. 11B), the cap assembly 760 is ready to be placed on bottle 800. In an exemplary embodiment, the rod 700 is centered within the cap assembly 760 when placed on bottle 800. In an alternative embodiment, the rod 700 may be positioned off-center (FIG. 10B) such that the tapered portion of the rod 700b can puncture the top and bottom seals 640a and 640b at various locations, but fully penetrate the bottom seal 640b. In the disclosed embodiments, the positioning of the tapered portion of the rod 700b is constrained by the diameter of the top 640a and bottom 640b seals, where the bottom seal 640b has a slightly smaller diameter compared to the top seal 640a. When positioned off-center as shown in FIG. 10B, the tapered portion of the rod must penetrate both the top and bottom seals 640a and 640b to create a passage between the top 600 and bottom 620 chambers of the blood culture bottle.

Figure 12:
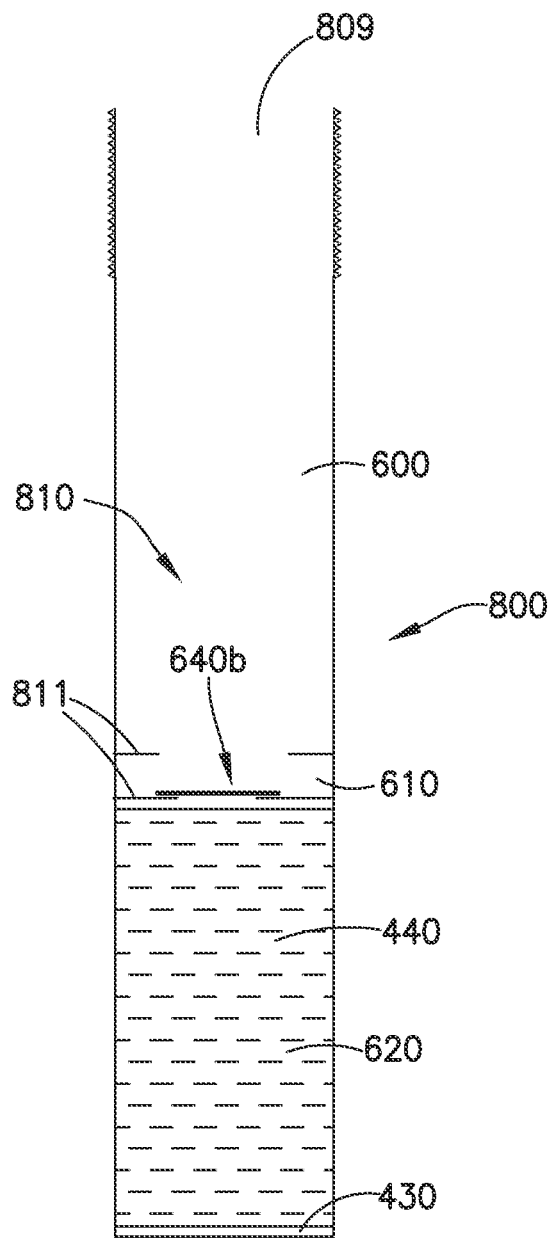
FIG. 12 is a schematic side view of a method of introducing an insert filling of a blood culture bottle and creating a chamber in the insert.

FIG. 12 illustrates a method of assembling the present invention. Chamber insert 810 contains chambers 600 and 610 for storing substances used in the mixing process. A portion of bottle 800 receives insert 810. The size and shape of bottle 800 and insert 810 may vary in different embodiments. The insert 810 contains protrusions 811 extending outwardly from the interior wall of insert 810 to define chamber 610. As shown in FIG. 10A or 12, protrusions 811 also define a top and bottom aperture of chamber 610. The insert 810 is received in the bottle 800 through an opening 809 in the top of the bottle 800. A sensor 430 is illustrated as placed at the bottom of the bottle 800. However, sensor location is largely a matter of design choice. Once the insert 810 is placed inside the bottle 800 (FIG. 10A or 12), media 440 is introduced to the bottom 620 of the housing 800. Next, a foil seal 640b is placed across the bottom portion of the defined protrusions 811.

Figure 13:
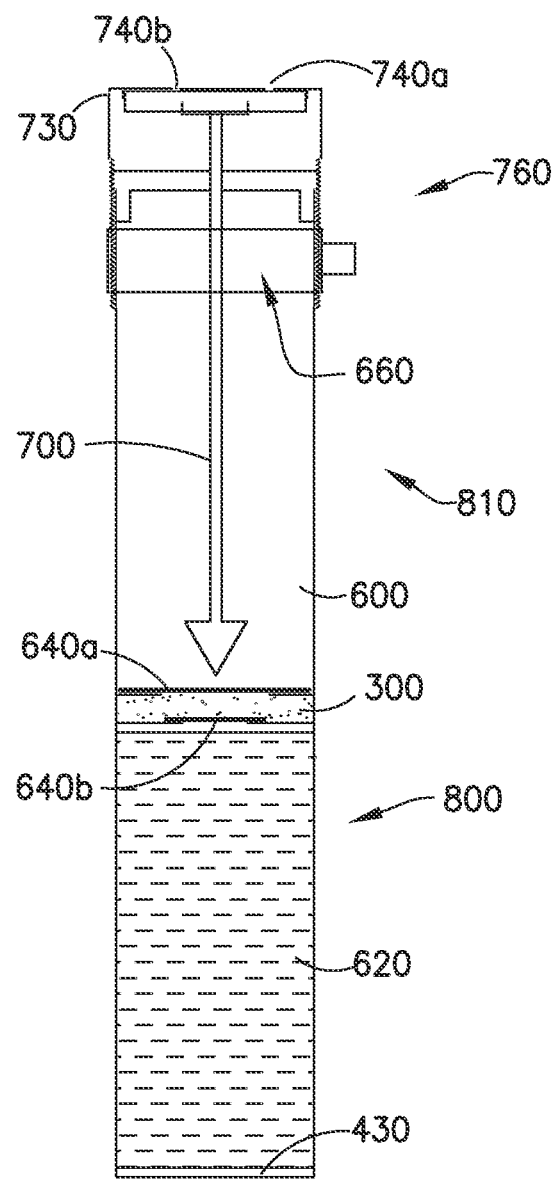
FIG. 13 is a schematic cut away side view illustrating the filling of the FIG. 12 chamber and placing the piercing mechanism on the housing.
Figure 14A:
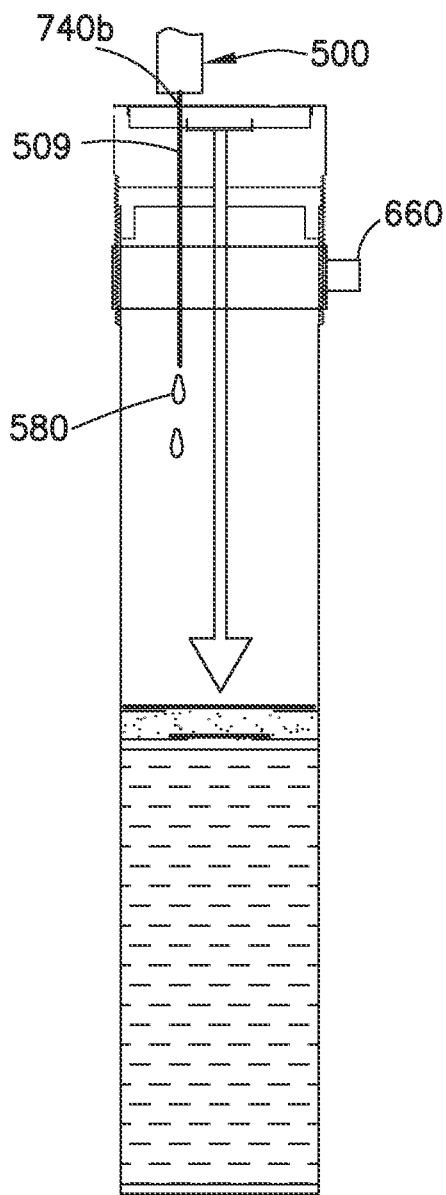
FIGS. 14A-B are schematic side views of a method of delivering a blood sample into a blood collection chamber of the device illustrated in FIG. 13B.
Figure 14B:
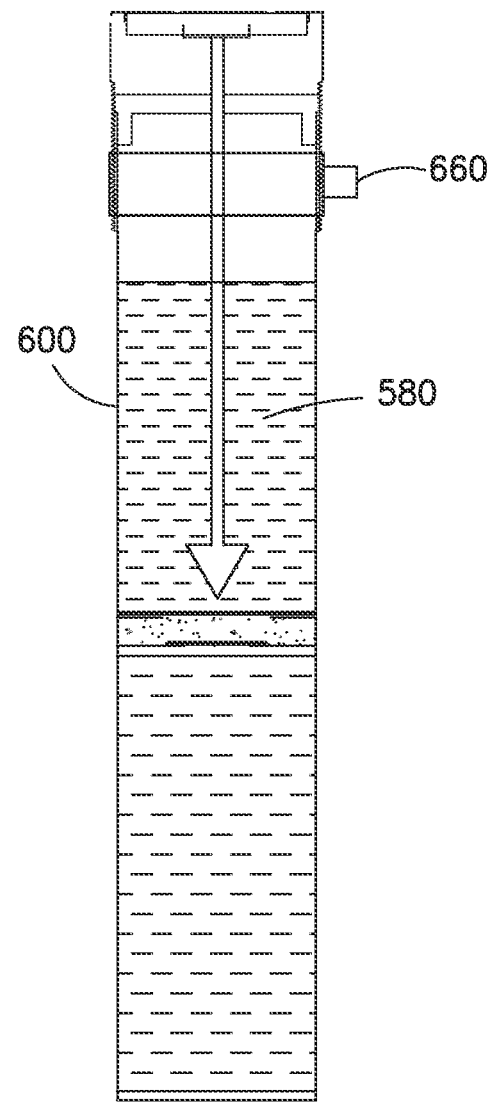

FIG. 13 illustrates further preparation and final assembly of blood culture bottle 800. In FIG. 13 the bottom aperture defined by the protrusion 811 is sealed by bottom seal 640b to separate media 440 from chamber 610. Resin 300 is added to chamber 610. Chamber 610 is subsequently sealed by disposing top seal 640a across the top aperture defined by protrusions 811 to create a resin chamber 610 separated from the chamber 620.

FIG. 13 also illustrates the placement of the cap 760 of FIGS. 11A-B. The cap 760 is placed onto the assembly with the tapered rod 700 facing downward. Either before or after the cap 760 is on the assembly, an optional safety lock 660 is placed on the outside of the assembly in a locked position to prevent undesired screwing or swirling motion that would potentially cause the seal 640 to break prematurely. As shown in FIGS. 11A-B, housing 701 of cap element 760 has inner screw threads 761 that cooperate with a corresponding set of outer screw threads 901 to fasten the cap 760 to the assembly. The blood culture bottle assembly ready for use.

FIGS. 14A-B and 15A-D illustrate the introduction of a blood sample into the blood culture bottle. Blood 580 is delivered by a blood withdrawing device 500 with a needle 509 into the blood chamber 600 as previously described. Once the chamber 600 is filled to the desired level (FIG. 14B), the safety lock 660, if attached, is removed (FIG. 15A). Next, cap 650 is twisted in direction 1120 to advance cap 650 in a downward direction to force the rod 700 downward (FIG. 15B). As the rod 700 moves downward, the tapered portion 700b of rod 700 first punctures top seal 640a, thereby allowing the blood 580 to come into communication with the resin 300. In an exemplary embodiment, the rod 700 punctures top seal 640a through its center. Optionally, the tapered portion 700b of the rod 700 can be positioned within the cap assembly 760 such that top seal 640a is punctured off-center, thereby increasing the surface area of the punctured seal. At a desired time, cap 650 is twisted further to its final position advancing the rod 700 even further downward until bottom seal 640b is punctured to allow the blood and resin mixture 1130 to be combined with the media 440, thereby creating a blood, resin, and media mixture 570 (FIG. 15C). The release can be timed and controlled automatically or manually. Referring to FIG. 15D, the blood culture bottle is inverted and the mixture 570 is extracted using a needle 1150 inserted into one of the circular openings 740a, 740b in the top of cap 650. The mixture 570 preferably flows into a collection device 1180 using a vacuum.

Different embodiments of this invention using a similarly configured blood culture bottle may have a time controlled release mechanism that uses a pushing rather than a twisting force to introduce sample components into a media. Additionally, the apparatus may have more than one chamber in the insert, and could use a different type or increased quantity of substances, depending upon the requirements of a particular assay. Additionally, the location of the sensor may vary as well as the number of sensors placed in the apparatus.

Figure 16A:
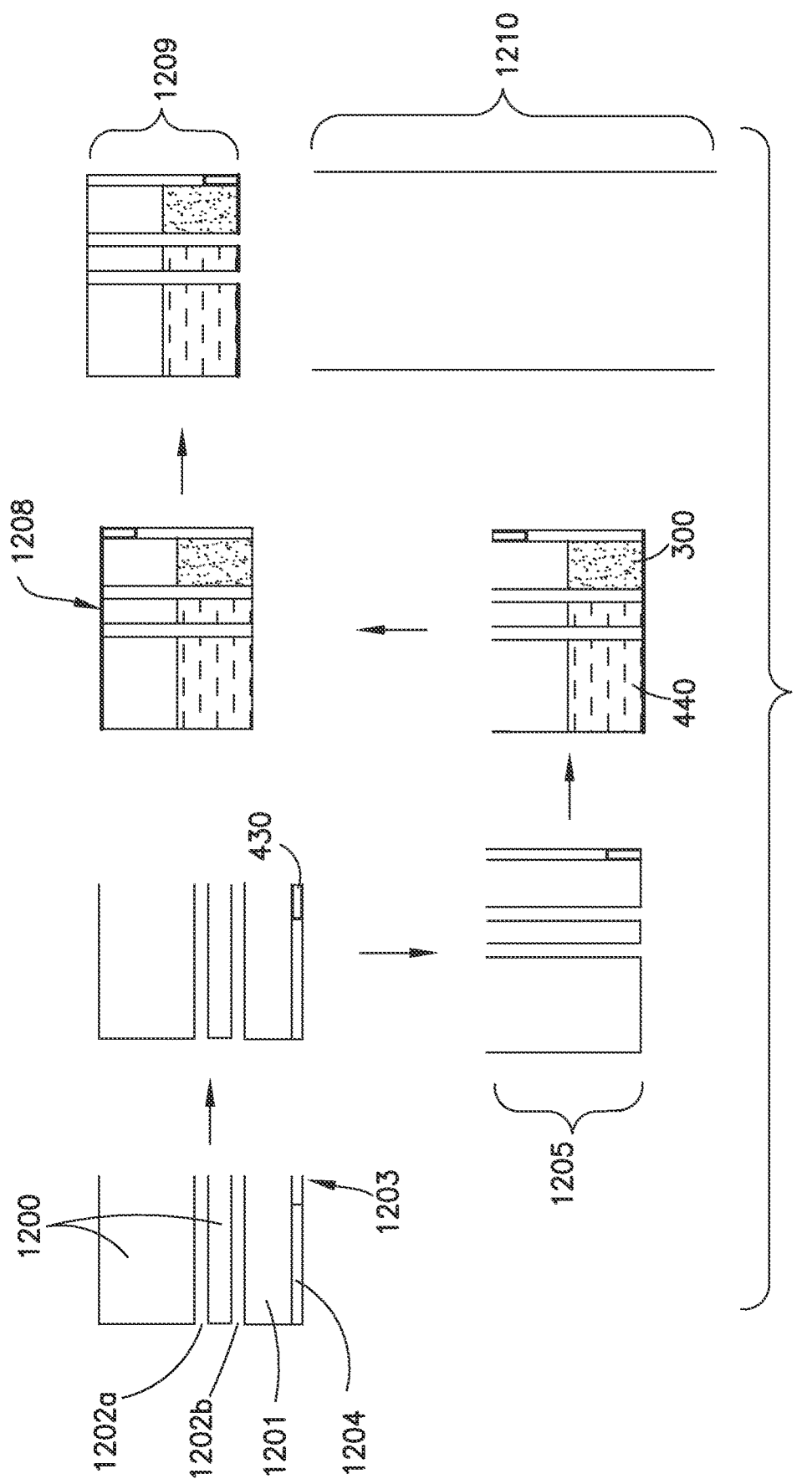
FIGS. 16A-B are schematic side views of alternative insert configurations for a blood culture bottle.

In yet another embodiment of this invention, a two chamber insert is configured as shown in FIG. 16A. The insert has two media chambers 1200 and resin chamber 1201. The insert has two passages 1202 that separate the media chambers 1200 from the resin chamber 1201. One passage on the side 1202a is for the tapered rod 1212 to pass through. The second passage 1202b receives the needle (not shown) used for blood sample delivery. The wall 1204 of the resin chamber 1201 contains a recess 1203 that receives a sensor 430. The insert has a seal 1208, e.g., a foil seal, which provides a separation barrier for the media chambers 1200, resin chamber 1201, and chamber tunnels 1202. Prior to applying the foil seal 1208, the media chamber 1200 and resin chamber 1201 are filled with a predetermined amount of media 440 and resin 300, respectively, and the sensor 430 is inserted into the sensor housing 1203. Once completed, the seal 1208 is applied on the insert, enclosing the various chambers 1200, 1201 and chamber tunnels 1202 under specified temperature and headspace gas, preferably oxygen, carbon dioxide, nitrogen, or any mixture thereof. In other embodiments of this invention, the location, size, and shape of the sensor housing 1203 and chamber tunnels 1202 may vary. Once fully configured, the media and resin chamber construction 1209 is inverted and fitted into one end of tubular receptacle 1210 such as Becton Dickinson's BACTEC FX 9000 series. In an exemplary embodiment, the tubular receptacle 1210 is open on both ends.

Figure 16B:
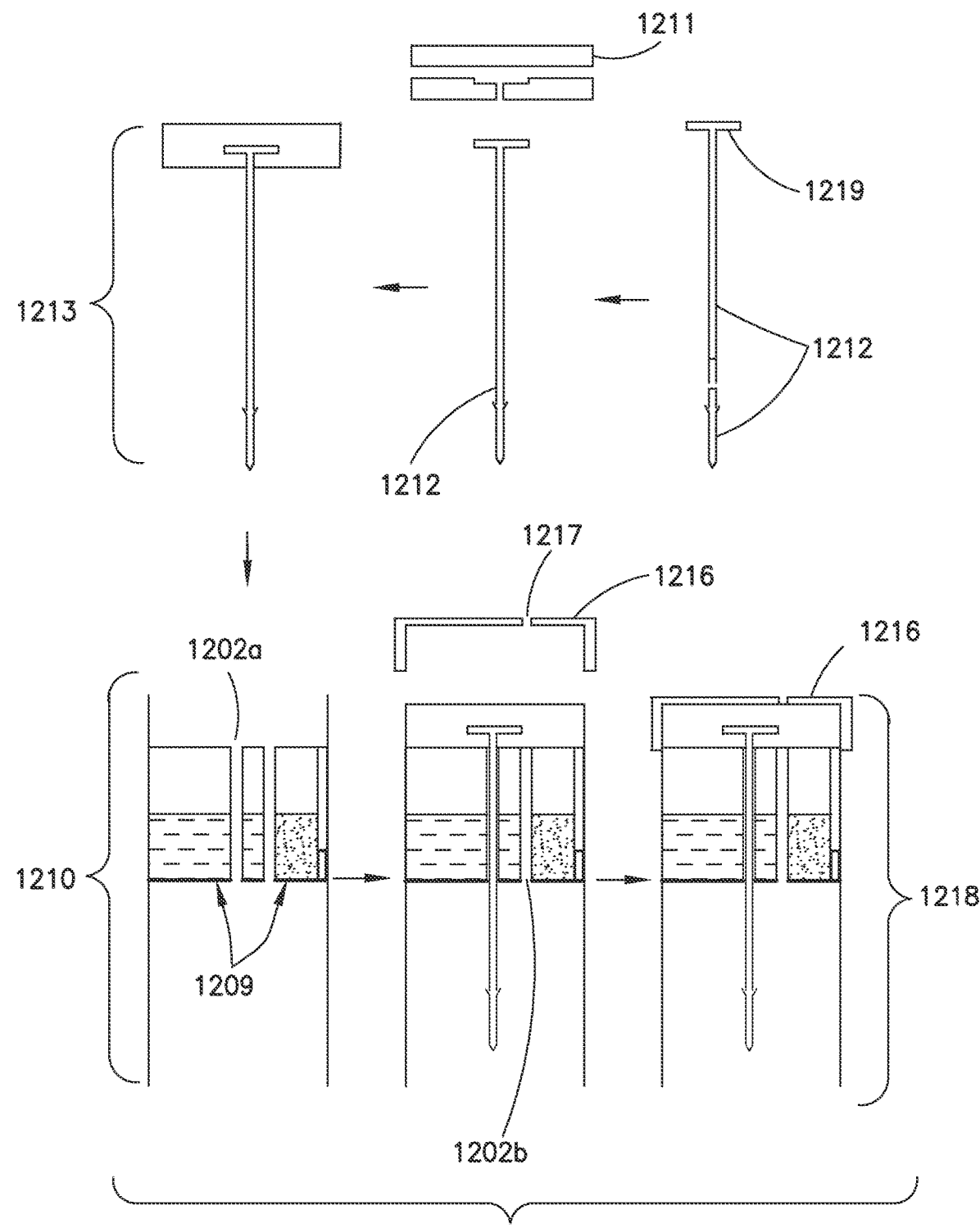

FIG. 16B illustrates the assembly of a tapered rod 1212 and cap 1211, which cap 1211 is fitted to the top portion of a blood culture bottle 1210. The rod has a flange 1219 that fits into the cap 1211. When assembled with the insert 1209 and tube 1210, the rod 1212 is configured with the tapered end inserted through passage 1202a. The rod 1212 can be inserted before or after the flange 1219 is placed in the cap 1211. Once the cap 1211 and rod 1212 are fitted together as assembly 1213, the assembly 1213 is inserted into the center passage 1202a of the media and resin chamber insert 1209, where the cap 1211 seals the tubular receptacle 1210. A metal closure 1216 is fitted with an opening 1217 that aligns with the side passage 1202b. The metal closure 1216 is placed over the cap 1211 and the top portion of the blood culture tube 1210, which creates the fully configured top assembly 1218 of the blood culture tube 1210. A perspective view of the assembly 1218 is shown in FIG. 17.

Figure 18:
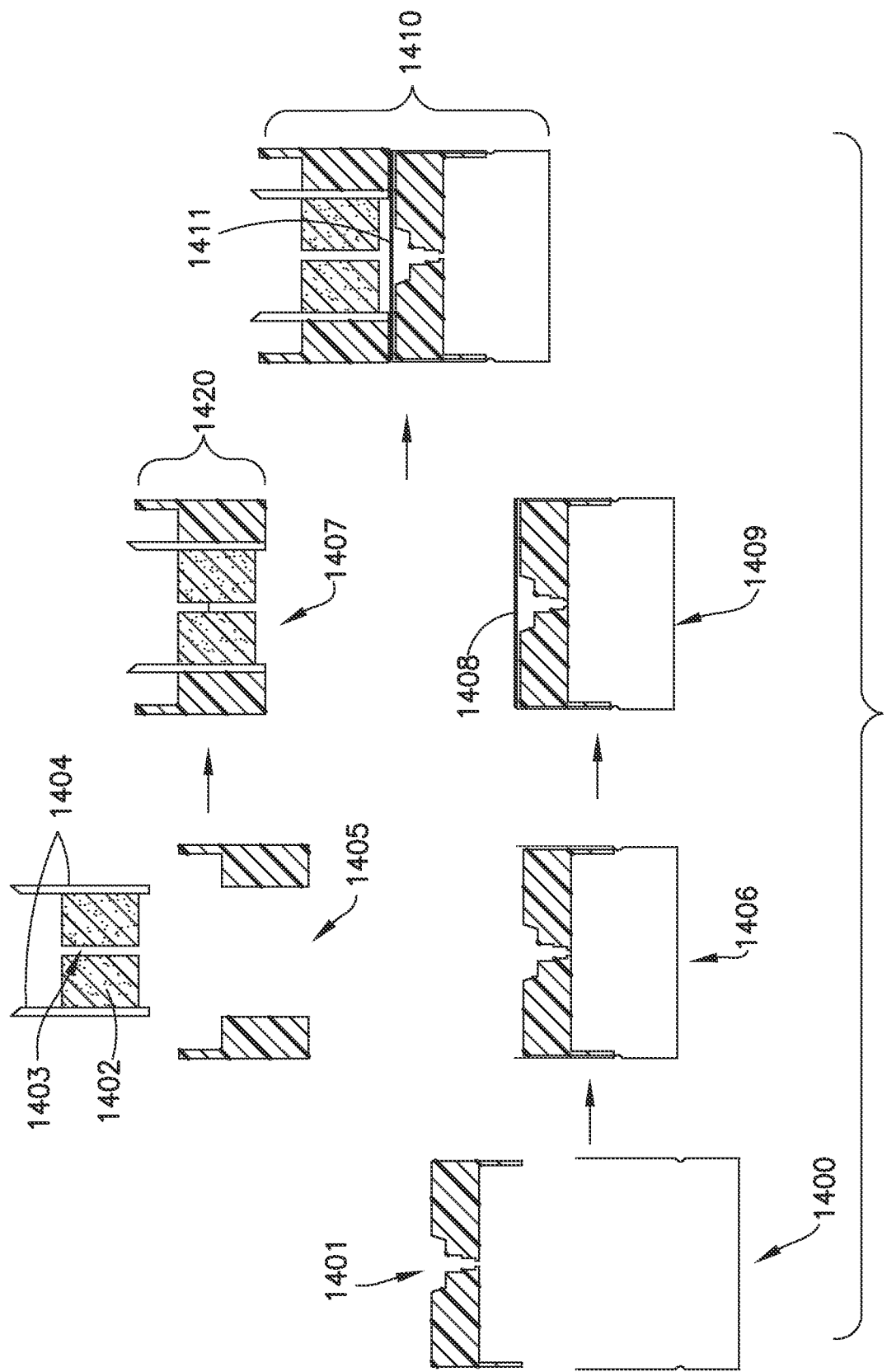
FIG. 18 is a series of cut away side views of a filter assembly configured as a bottom portion of a culture bottle assembly.

FIG. 18 illustrates the method of constructing the bottom portion assembly 1410 of the blood culture tube 1210. The assembly 1410 houses a filter 1402. A filtrate control gate 1401 is fitted into the opening of the filtrate collection reservoir 1400. The filtrate control gate 1401 has an opening 1403 to receive the rod 1212. The opening tapers in a stepped design to aid in the filtration process. The filtrate control gate 1401 is covered with a pierceable seal 1408, e.g., a foil seal, which forms a barrier between the filtrate control gate 1401 and plunger 1405.

Figure 19:
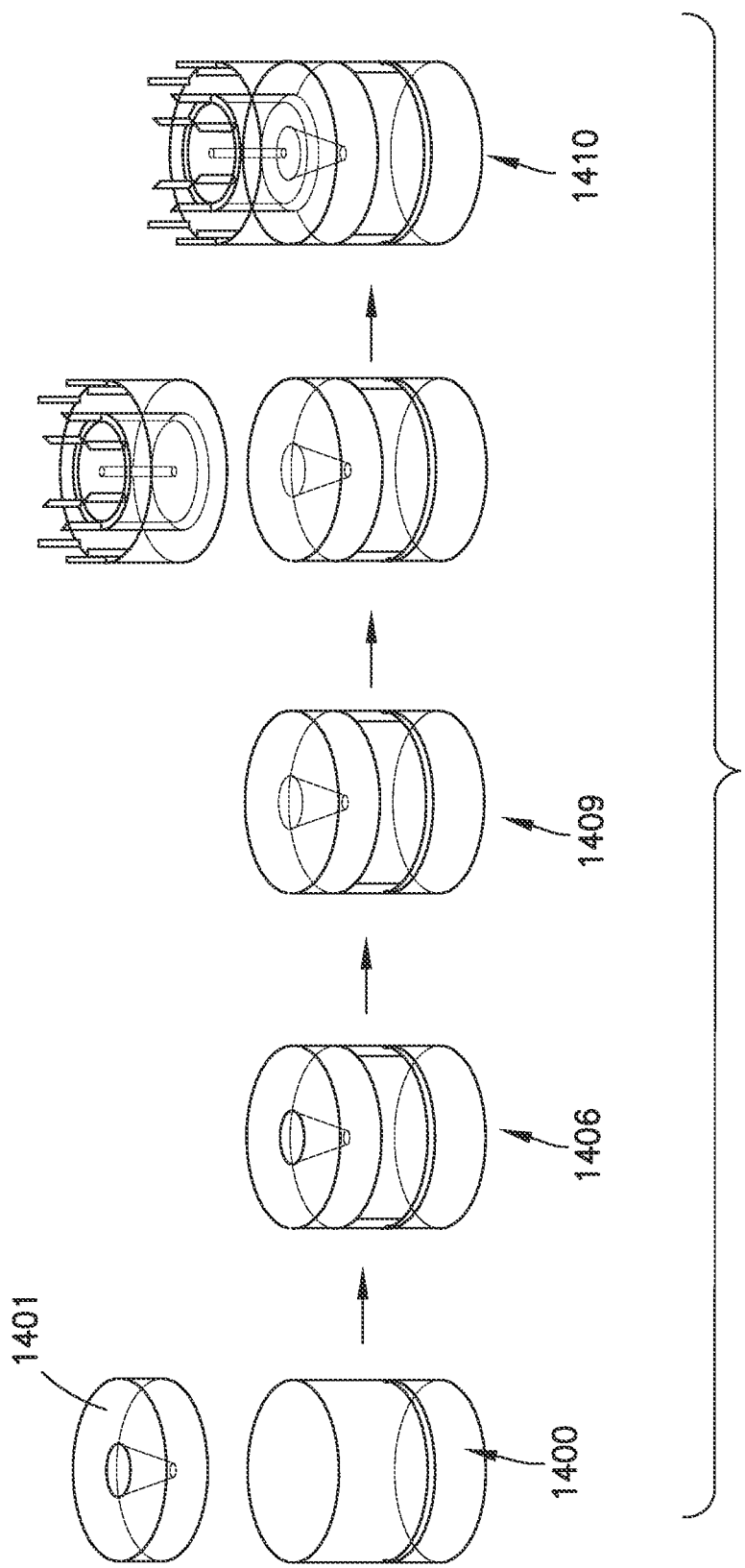
FIG. 19 is a series of perspective views of the assembly depicted in FIG. 18.

The plunger 1405 is made of a pliable material, e.g., rubber, which houses a filter 1402 having a passage in the center 1403 to receive the rod 1212. The filter 1402 can be a simple mesh filter, a multilayer filter or a packed filtration mass. The skilled person will select a suitable filter material and pore size for the specific application. The filter 1402 has, at its perimeter, one or more spikes 1404 that puncture the foil seal 1208 (FIG. 16A) of the top portion 1218 of the blood culture tube 1210 (FIG. 16B) when the top and bottom portions of the culture tube/filter assembly are advanced toward each other. Lastly, plunger 1405 and filter assembly 1420 are placed on top of the filtrate collection assembly 1409. The passage 1403 in the filter 1402 is with an opening 1411 under the filter 1402 when the bottom portion 1410 of the blood culture chamber is fully configured. Different embodiments of this invention may configure the bottom portion filtration system 1410 with different filtering mechanisms or may vary the placement and number of spikes. A perspective view of the assembly of the bottom portion 1410 of the blood culture bottle is shown in FIG. 19.

Figure 20:
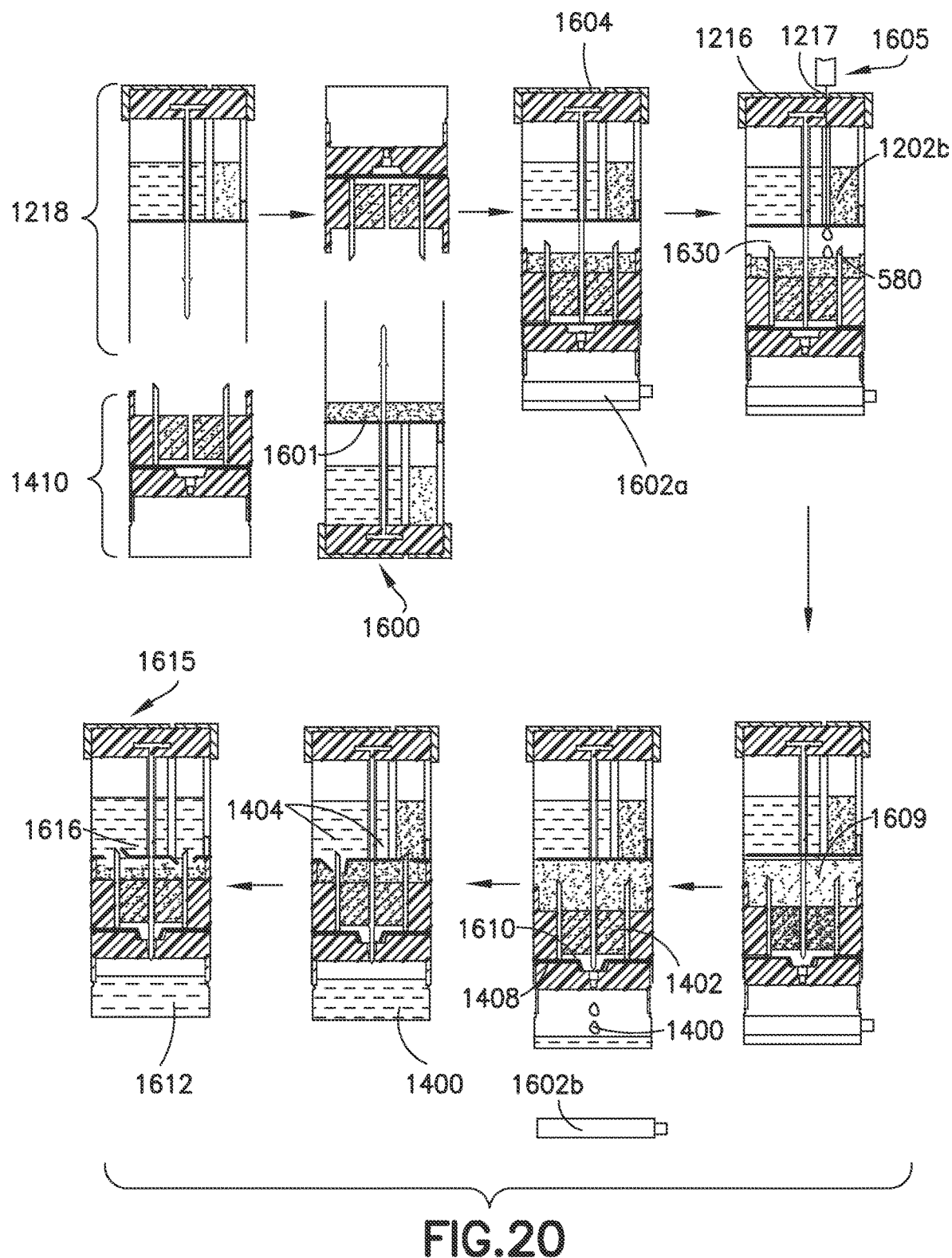
FIG. 20 is a series of cut away side views of the operation of a device formed from top and bottom portions, the bottom portion as illustrated in FIG. 19.

FIG. 20 illustrates how the sample components are combined and the substance filtered into a filtration collection reservoir 1400. First, the top assembly 1218 is inverted and an optional pre-treatment reagent 1601, for example, a lysis reagent, is introduced under a specific temperature and headspace gas, preferably oxygen, carbon dioxide, or nitrogen or any mixture of the aforementioned gases. If the content of the assembly contains gas in the headspace 1630, the top and bottom portions are assembled in a hood with desired gas temperature. A vacuum needle can be used after the two portions have been assembled to pull out most of the gas out of the headspace via the off-center channel 1202b. An adequate pressure in the confined headspace 1630 is required to automatically draw blood into the device assembly. In a preferred embodiment, an adequate pressure in the headspace is less than the normal atmospheric pressure.

Figure 21:
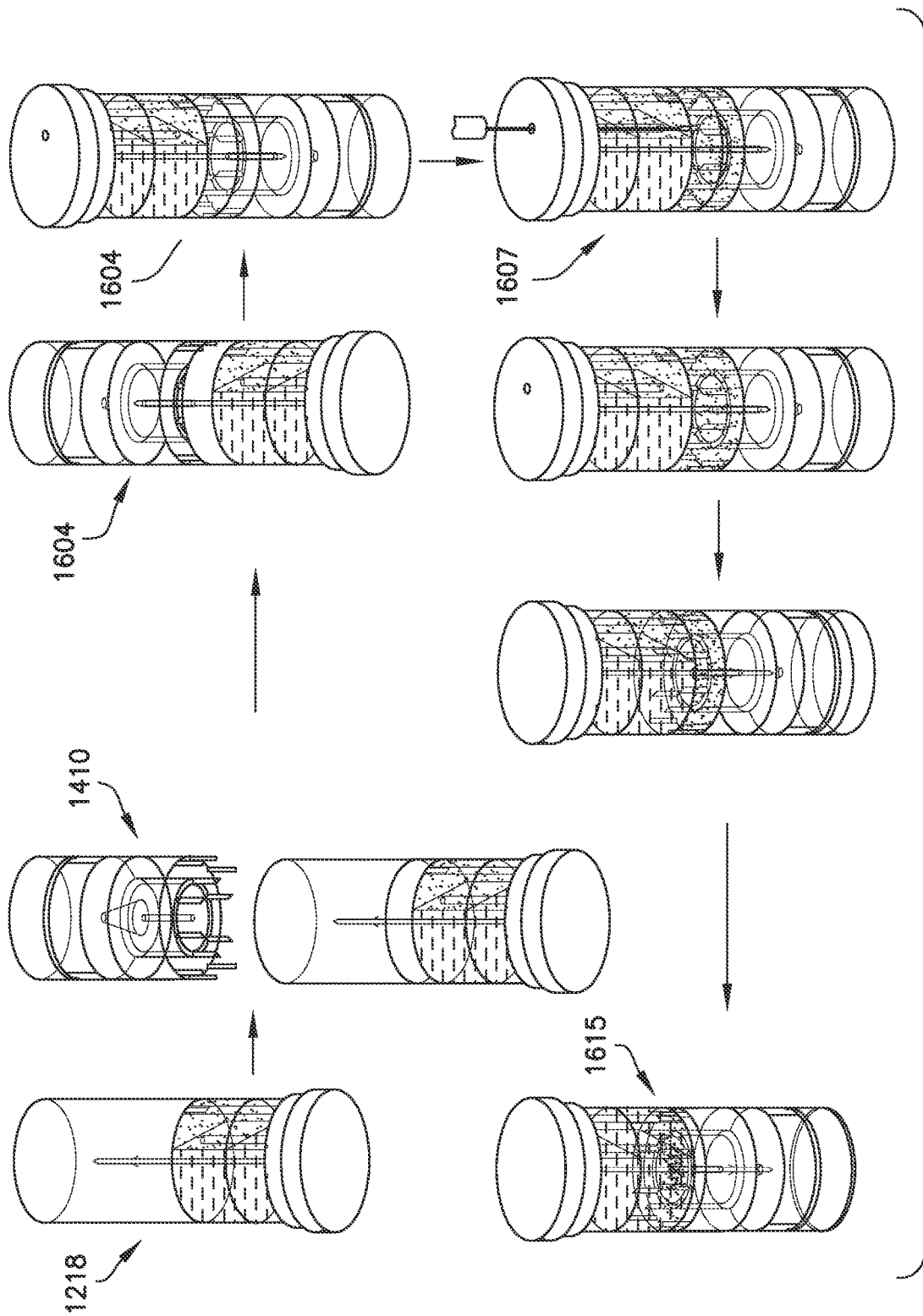
FIG. 21 is a perspective view of the device of FIG. 20.
Figure 22A:
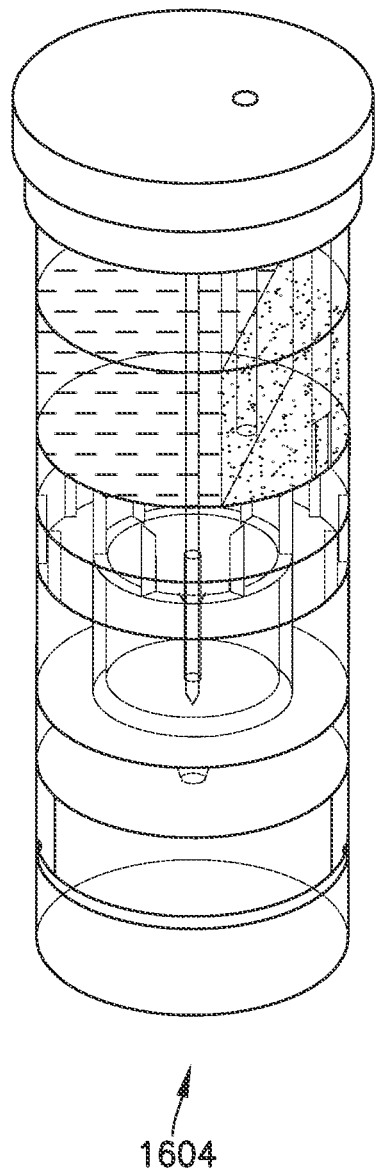
Figure 22B:
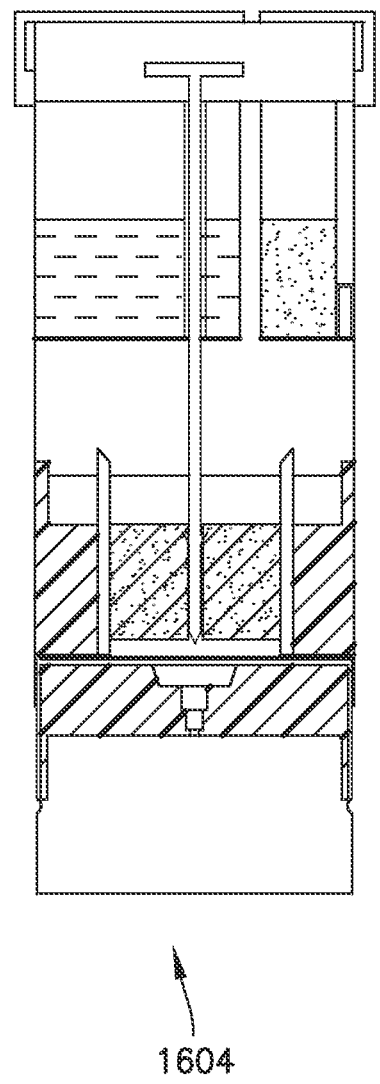

Suitable lysis reagents include saponin and BACTEC™ lytic media. Second, the bottom assembly 1410, which is also inverted, is advanced into the open end of the assembly 1218. Once the bottom assembly 1410 is fitted into the top assembly 1218, then the full culture bottle is inverted as assembly 1604. An optional safety lock 1602*a* is added, to prevent accidental "pressing/filtration" action. Next, blood 580 is introduced by a blood sample withdrawing device 1605, using a vacuum force, through the opening 1217 in the metal closure 1216 that aligns with the side chamber tunnel 1202*b*. Blood 580 is deposited in the headspace 1630 created between the top portion 1218 and bottom portion 1410 of the inverted blood culture bottle assembly 1604 creating a blood and reagent mixture 1609. Next, the safety lock 1602*a* is removed 1602*b*. The removal of the safety lock can be accomplished both manually and/or automatically. Then, also either automatically or manually, the top portion 1218 and bottom portion 1410 are advanced toward each other as the tapered end of the rod 1212 breaks the foil seal 1408. The spikes 1404 break the seal 1208 (not shown) that separates the resin 300 and media 440 from the blood and reagent mixture 1609. Once the seal 1208 is broken, the resin 300 and media 440 combine with the blood and reagent mixture 1609 to create a blood, lysis reagent, resin, and media concentrate 1616. Preferably, the penetration of the spikes 1404 and the rod 1212 is sequential. The spikes 1404 break the seal 1208 of the top portion 1218 before the tapered end of the rod 1212 breaks seal 1408 of the bottom portion 1410. This sequence allows concentrate 1616 to form before the excess liquid or residual by-product 1612 flows through filter 1402 into the filtrate collection reservoir 1400. After a desired period of time, the top portion 1218 and the bottom portion 1410 are further advanced toward each other. The final concentrate 1616 remains in the top portion 1218 for further retrieval and processing. The residual by-product 1612 remains in the filtrate collection reservoir 1400, from which the by-product is eventually discarded. A perspective view of this embodiment of the invention is shown in FIG. 21. FIGS. 22A-D depicts the initial position of the blood culture bottle assembly 1604 in both a side view and a perspective view. FIG. 22C-D show a side and perspective view of the final active position 1615 of the blood culture bottle assembly 1604 after all substances have been mixed to form a final concentrate 1616 and after the residual by-product 1612 has passed through the filter and into the filtrate collection reservoir 1400.

Different embodiments of the invention that use a culture bottle with a similar configuration may deploy a screw-type time controlled release mechanism rather than the pressing mechanism previously described. The number of chambers and passages between the chambers may also vary in other embodiments in order to accommodate different testing environments. These substances may be solids, gasses or liquids or any combination thereof.

Figure 23A:
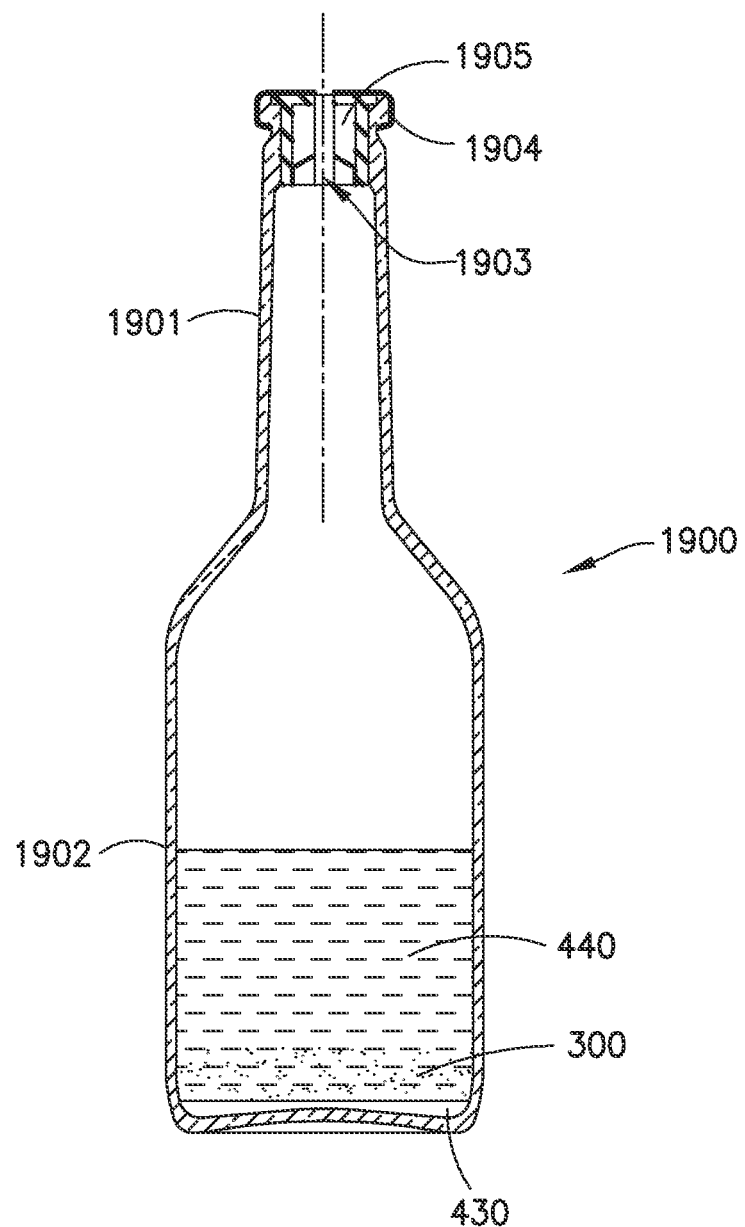
FIG. 23A is a cut away side view of a blood culture bottle containing a chamber insert according to another embodiment.

FIG. 23A illustrates a side view of a blood culture bottle 1900 configuration of yet another embodiment of the invention. The blood culture bottle 1900 contains a sensor 430, resin 300 and media 440 in a bottom chamber 1902, while the top chamber 1901 contains a chamber insert 1903 and a cap 1904. The chamber insert 1903 contains a lysis reagent 1905. Commercially available blood culture bottles such as Becton Dickinson's BACTEC FX 9000 series can be used as blood culture bottle configurations for this embodiment and other embodiments of the invention using a similar culture bottle configuration.

Figure 23B:
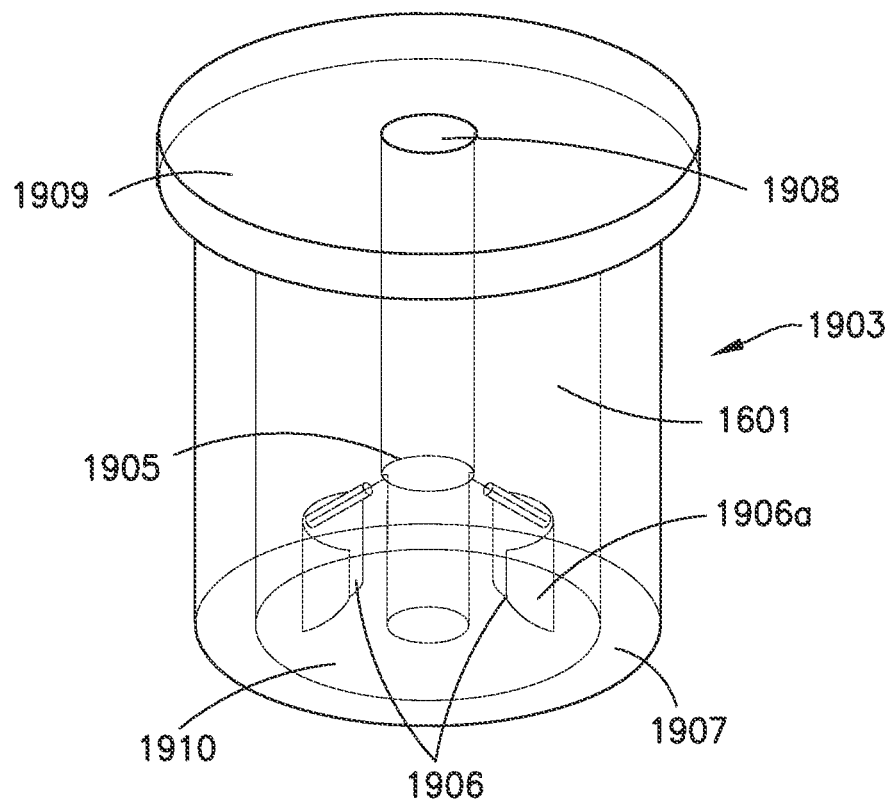
FIGS. 23B-C are perspective views of the chamber insert having a ferromagnetic cutter.
Figure 23C:
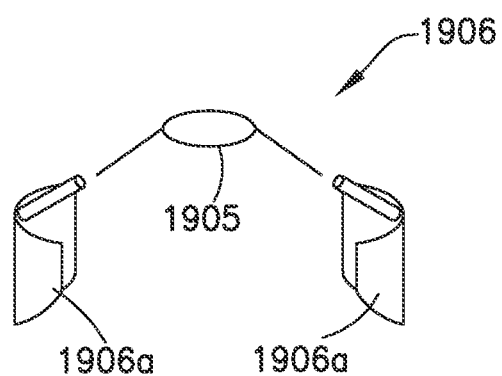
Figures 25A, 25B:
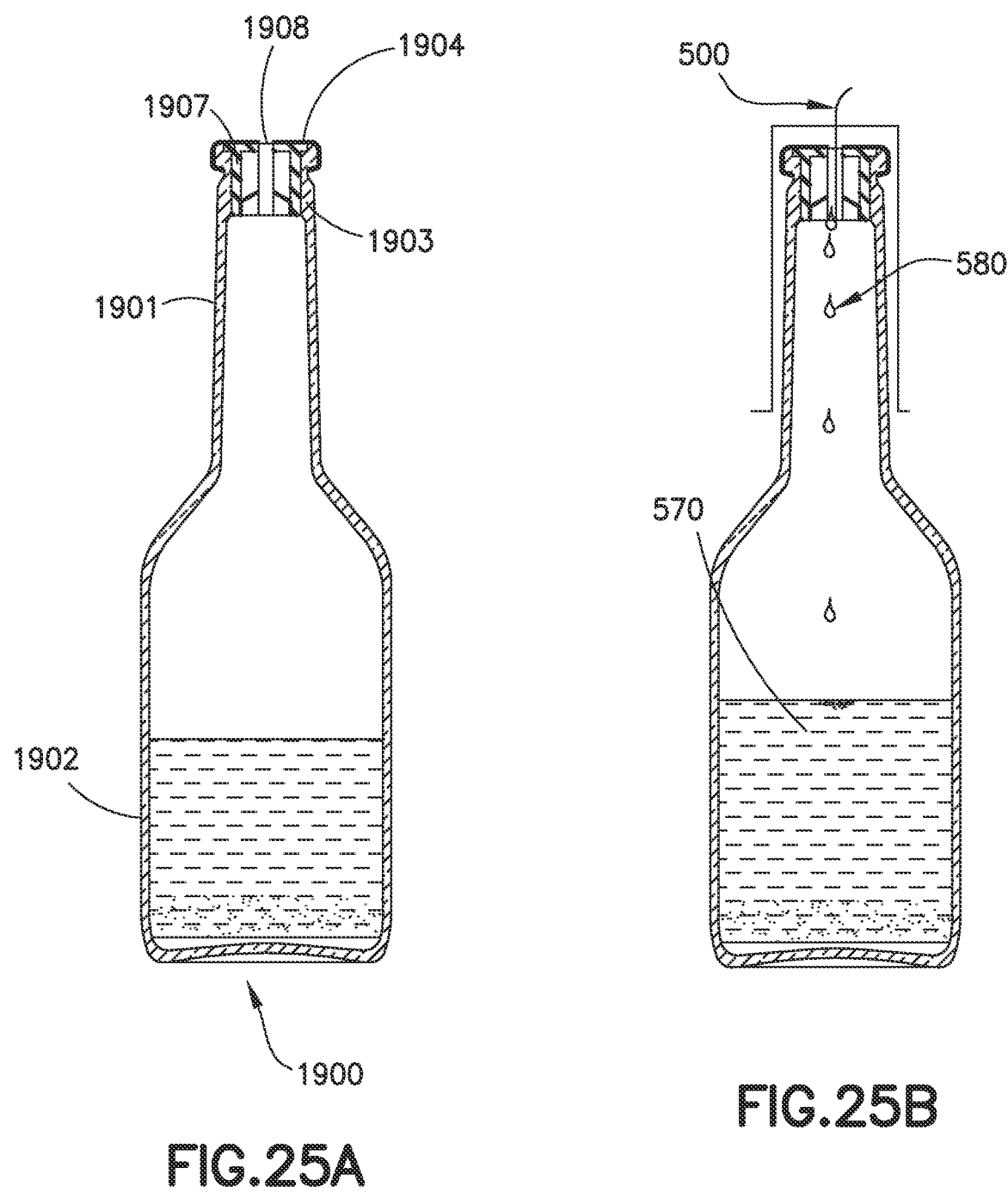
FIGS. 25A-E illustrate the release of the ferromagnetic cutter into the bottle contents.
Figure 25C:
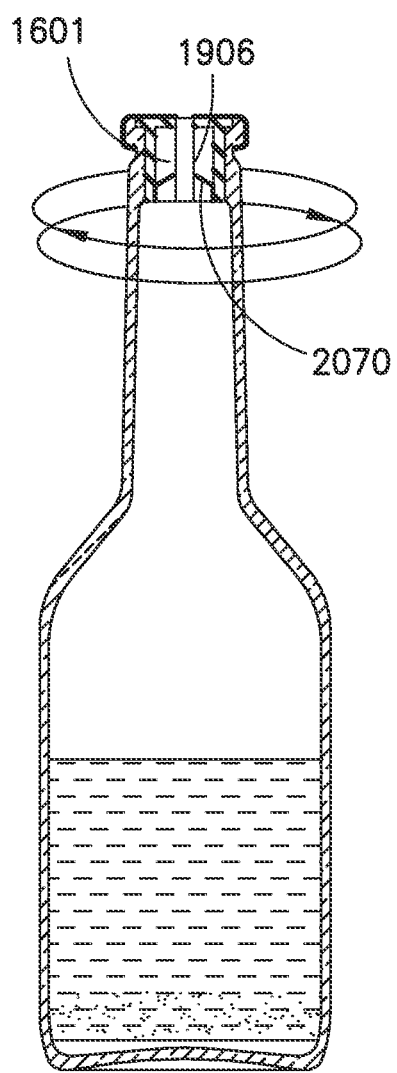
Figure 25D:
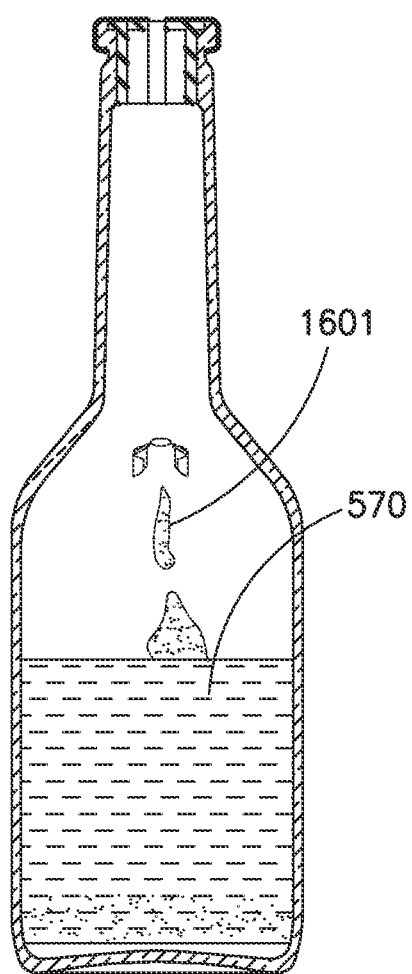
Figure 25E:
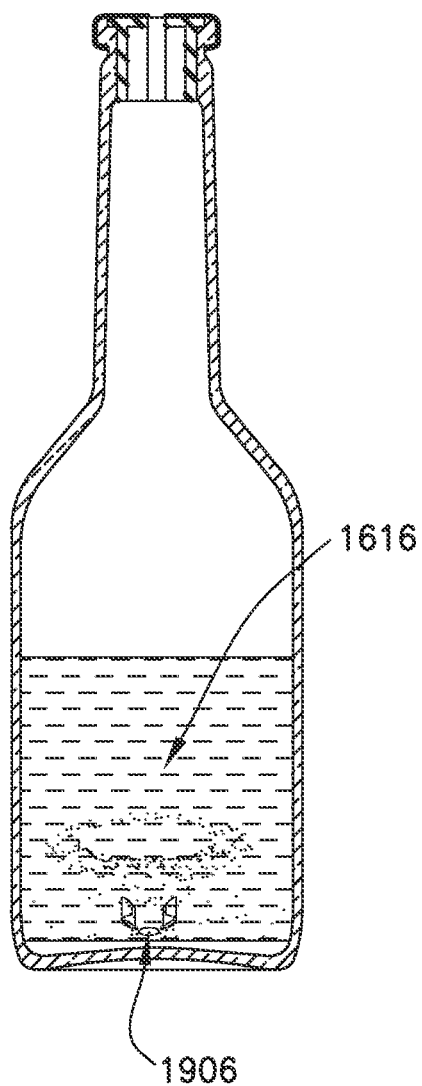

FIGS. 23B-C illustrate the configuration of the lysing reagent chamber insert 1903. The chamber insert 1903 has a housing 1907 which is tubular so as to fit in top chamber 1901 (FIG. 23B). The top portion 1909 of the housing 1907 has a circumference greater than the lower portion in order to rest on top of the blood culture bottle 1900 once inserted therein. Housing 1907 has a passage 1908 through its center creating openings at the top 1909 and bottom 1910 of the housing 1907. A rotational cutter mechanism 1906 is disposed around the passage 1908. The rotational cutter mechanism 1906 has a tether 1905, in this instance made of a ferromagnetic wire. Curved wings 1906*a* having inserts extending at an angle are fitted over the tether 1905 to create the rotational cutter mechanism. The wings 1906*a* have a sharpened edge that points downward when assembled with the tether 1905. In this instance, the wings 1906*a* are made of plastic, but the wings 1906*a* could be made of a different material and various configurations. A skilled person can choose an alternative configuration as a matter of design choice.

FIG. 24A-I illustrates the method of assembling the lysing reagent chamber insert 1903 and its placement within the blood culture bottle 1900. Each letter designation in FIGS. 24A-I represents a method step. Housing 1907 is illustrated in step A. In step B, the housing is inverted. Once inverted, the rotational cutter mechanism 1906 is placed over the center tube 1908. In step C, the lysing reagent 1601, or other desired substance, is added to the housing. In step D, a seal 2070 is placed over the bottom of the housing 1907 and the lysing reagent chamber insert 1903 is inverted to its upright position in step E. The lysing reagent chamber insert 1903 is then placed into the opening 2005 at the top 2006 of the blood culture bottle 1900. The lip 1909 of the housing 1907 sits on the lip 2007 of the blood culture bottle 1900 in step G. In step H, a septum 2060 is placed over the housing 1907 and blood culture bottle 1900 to secure the lysing reagent chamber insert 1903 on the blood culture bottle 1900. Finally, in step I, a metal cap 1904 is placed over the septum 2060. The metal cap has an opening that fits over the passage 1908 to accommodate needle access to the contents of the chamber insert 1903. Optionally, the metal cap is secured with an additional cap (e.g., a plastic or a paper cap) (not shown) to secure the septum and provide protection against contamination. The additional cap is removed prior to use.

FIGS. 25A-E illustrate the method of releasing sample components into a liquid media in the embodiment illustrated in FIGS. 23A-24I. As before, each letter designation in FIGS. 25A-D represents a method step. First the optional plastic cap that is used to secure the metal cap 1904 over the septum 2060 must be opened, exposing the passage 1908 in housing 1907. The blood 580 is delivered by a blood withdrawing device 500 through the passage 1908 in the housing 1907 and into the bottom chamber 1902 where the blood 580 combines with the media 440 and resin 300. In step C, after a predetermined amount of time, an external force, in this instance, an exterior magnetic spinner, is applied to the assembly, either automatically or manually, and the rotational cutter mechanism 1906 begins to spin downward along the passage 1908, piercing the seal 2070 that retains the lysing reagent in the insert 1903. In alternative embodiments, an external force (e.g., an exterior magnetic spinner) can be re-positioned such that the rotational cutter mechanism 1906 continues to spin after it has been released from the chamber insert 1903. The lysing reagent 1601 is released and combined with the resin, media, and blood mixture 570, in step D. In this embodiment, a lysing reagent 1601 is added to the resin, media and blood mixture 570 (shown as 1616 in step E). The time to release the lysing reagent 1601 can be controlled manually and/or automatically such that the lysing reagent 1601 is released when the resin 300 has adsorbed most of the antibiotics, if present, in the media and blood mixture 570. In step E, the rotational cutter 1906 is released into the resin, media, blood and lysing mixture 1616 and, optionally, continues to spin further mixing the substances until the mixture 1616 is ready for inoculation.

Other embodiments of the invention using a similar blood culture bottle configuration can vary in size and shape as long as the lysing reagent chamber insert 1903 is able to be inserted into and fixed inside of a container. Additionally, substances in any of the chambers may vary depending on need. The location and number of sensors can also vary. The rotational cutter mechanism 1906 can be designed to be heavier or lighter than or equal to the density of the mixture of substances in the bottom chamber 1902 of the blood culture bottle 1900 in order to function as a stirrer at any depth in the volume of the mixture. Further, the rotational cutter may achieve its spinning function either mechanically or by an appropriate automation apparatus.

Figure 26A:
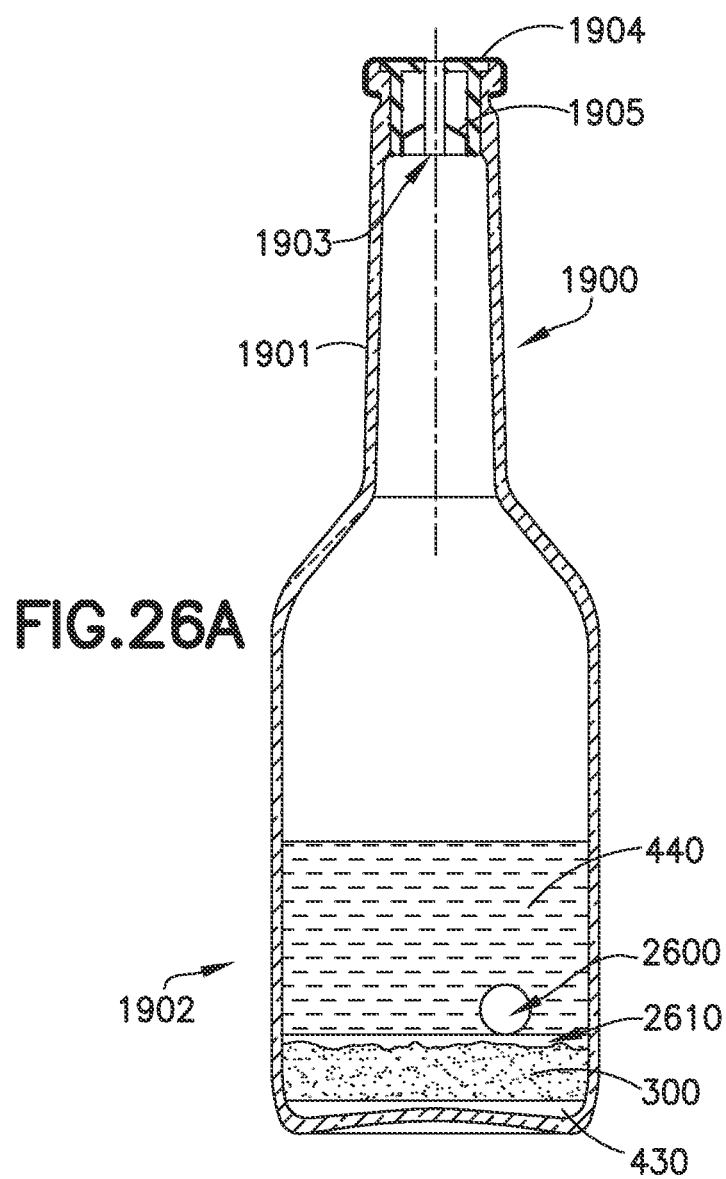
FIG. 26A is a cut away side view of a blood culture bottle containing an abrasive magnetic bead.

FIG. 26A illustrates a side view of yet another embodiment of the invention. The bottle 1900 is described as a blood culture bottle with reagents for that application and environment. However, the inventive aspects of this embodiment are not to be limited to blood culture bottles, but are applicable to any environment where controlled combination of reagents is sought.

In this embodiment, a seal is used to separate a bottom portion 1902 of the bottle 1900 from a top portion 1901. Consistent with previous descriptions the bottom portion 1902 is referred to as a "bottom chamber." Similarly, the top portion 1901 is referred to as a "top chamber." This is not a conventional use of the term "chamber" as there is no structural delineation between the top 1901 and bottom 1902 portions. In using the word chamber, applicants are exercising their ability to act as their own lexicographer in order to provide consistency among the many embodiments described herein.

The blood culture bottle 1900 contains a sensor 430, resin 300 and media 440 in a bottom chamber 1902. The top chamber 1901 has a cap 1904 configured to receive a blood sample therethrough by conventional mechanisms for introducing blood sample into a culture bottle. For example, cap 1904 may be a septum cap pierced by a needle to inject blood into the culture bottle. Such mechanisms are well known to one skilled in the art and are not described in detail herein. In the illustrated embodiment, the sensor 430 is one in which an indicator material is disposed in a silicone matrix. Such sensors are well known to one skilled in the art and are not described in detail herein. Typically such sensors are formed as a layer on the bottom surface of the container and cured. The resin 300 is disposed directly on top of the sensor 430. The resin is then covered by a thin layer of a biologically inert polymer such as for example room temperature vulcanized (RTV) silicone barrier 2610 to separate the resin 300 from what is disposed on top of the barrier 2610 (i.e., growth media 440 in this embodiment). Preferably, the RTV silicone barrier 2610 is attached to the sidewalls of the bottom chamber 1902 to securely hold the resin at the bottom of the chamber and separate from the media 440.

After a blood sample (not shown) is introduced into the top chamber 1901 of the blood culture bottle 1900, the resin 300 is allowed to mix with the culture media and blood sample by using one or more agitation bead(s) 2600 which, when activated, abrades the barrier 2610. As the barrier 2610 is abraded and pulverized, the resin 300 intermixes with the media 440. The magnetic bead 2600 is disposed in the bottom chamber 1902. The magnetic bead is made of a biologically inert injection moldable polymer, preferably a polypropylene or polyester, blended with iron oxide. Those skilled in the art are aware that the ratio of polymer to iron oxide must be such that the resulting magnetic bead supports magnetic agitation in order to abrade the barrier 2610 when activated (or agitated). In the exemplary embodiment, the magnetic bead is spherical, however other shapes such as a rod-shaped element are also contemplated so long as the magnetic bead abrades the barrier 2610 sufficiently to release the resin 300 into the media 440. The outermost layer of the magnetic bead 2600 (not shown) is an abrasive or textured surface with protrusions that are about 5 to about 25 thousands of an inch in height to effectively rupture the barrier 2610 upon agitation of the magnetic bead.

Figure 26B:
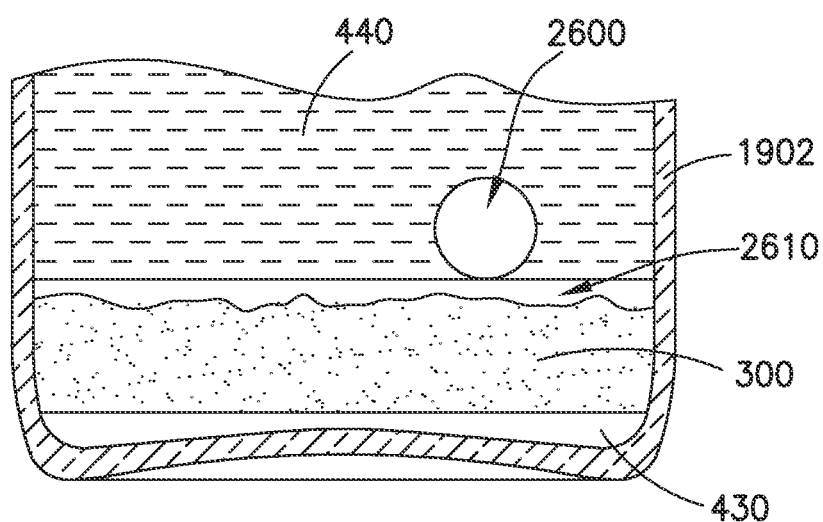
FIG. 26B is a cut side view of the bottom portion of the blood culture bottle containing the abrasive magnetic bead with a resin layer and a barrier.

FIG. 26B illustrates an enlarged view of the bottom chamber 1902 containing a sensor 430, a resin 300 covered with a barrier 2610, a media 440, and a magnetic bead 2600. The magnetic bead 2600 is activated by an external force (e.g., a magnetic agitator) that is located in close proximity to the blood culture bottle. In an exemplary embodiment, the magnetic bead is activated by an externally applied magnetic force (e.g., an automated magnetic agitation system or a magnetic stirrer). One skilled in the art is aware of instruments or sources of magnetic force that can be used to activate the magnetic bead. For example, any instrument that provides an external magnetic force can be deployed where the placement of the culture bottle 1900 therein activates the magnetic bead, which in turn abrades the RTV barrier 2610 to release the resin 300 into the blood (not shown) and liquid media 440.

In all embodiments of the invention, commercially available BACTEC FX 9000 series blood culture bottles can be configured to perform the methods of the invention. Additionally, the BACTEC FX 9000 series can be used to automatically perform the methods of this invention.

Many of the various elements and features described above are common to other embodiments of the present invention described herein. These common elements are described herein using alternate terms in some embodiments. For example, "caps" and "cap elements" are also described as "septums" and "septum/cap assemblies (see, e.g. the septum/cap assembly 2700, which includes a cap having a sub-element (i.e. the septum). Caps with additional features are included in the term "cap elements." Likewise, "sealing element" includes the embodiments such as the foil seal 310, the membrane 2730, the barrier 3040, and other structures described herein that perform a sealing function. The "vessel insert" is also referred to as a chamber or compartment in some embodiments. The body portion of the vessel that receives the vessel insert is also referred to as a chamber or compartment in some embodiment. Some elements and functions are further described by their inherent physical or geometric properties, or by their arrangement with other components of the apparatus described herein, including those arrangement and relationships inherent in FIGS. 1-37D. For example, many features are described in terms of proximate and distal, upper and lower, or top and bottom with respect to the other features with which they are combined. Such descriptions find support in FIGS. 1-37D. Likewise, references to interior and exterior portions of a feature find support from the drawings, which illustrate interior and exterior aspects of the vessel insert, body portion of the vessel, etc. Such relational terms are well understood by a person or ordinary skill in the art. Also references to conditions are not made in absolute terms, but relative to normal conditions. For example, any references to "vacuum pressure" or "vacuum" are made relative to atmospheric pressure and, as such include any degree of pressure that is less than atmospheric pressure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for a controlled combination of reagents, the apparatus comprising:
   a vessel adapted for receiving a biological sample having a neck portion and a body portion wherein the body portion of the vessel contains a culture media prior to receiving the biological sample and wherein the body portion of the vessel comprises one or more sensors for monitoring conditions in the culture media or a headspace gas in the vessel;
   a cap element attached to the vessel;
   a vessel insert secured in the neck portion of the vessel by the cap element and adapted for receiving at least one reagent wherein the at least one reagent is selected from the group consisting of adsorption resin, culture medium, lytic reagent, and a combination thereof, wherein the culture media is a lytic media adapted to grow microorganisms therein, the microorganisms selected from the group consisting of aerobic microorganisms, anaerobic microorganisms, mycobacteria, fungi, and yeast and wherein the culture media is in liquid or lyophilized form;
   wherein the cap element further comprises a pierceable aperture through which is received the biological sample into the vessel or vessel insert;
   at least one sealing element separating the at least one reagent received by the vessel insert from the body portion of the vessel, and
   a rod having a proximal end and a distal end positioned within the vessel so that the proximal end is adjacent to the cap element and distal end is in a first position proximal to the at least one sealing element; and
   wherein force applied to the proximal end of the rod results in the distal end of the rod moving from the first position to a second position thereby disrupting the at least one sealing element to allow contents of the vessel insert to release into the body portion of the vessel, and wherein the apparatus is operable to initiate disruption separately from and after receiving of the biological sample via the pierceable aperture into the vessel or vessel insert.

2. The apparatus of claim 1, wherein the vessel insert is tubular-shaped and wherein the distal end of the rod is tapered.

3. The apparatus of claim 2, wherein the force is applied either automatically or manually to the proximal end of the tapered rod, and wherein the distal end of the tapered rod pierces the vessel insert thereby disrupting the at least one sealing element and releasing the contents of the vessel insert into the body portion of the vessel wherein the vessel insert is sealed by the at least one sealing element, and wherein the tapered rod pierces the at least one sealing element.

4. The apparatus of claim 3, wherein the cap element is threaded onto the neck portion of the vessel and twisting the cap element downward onto the neck portion of the vessel causes the tapered rod to advance and pierce the at least one sealing element thereby disrupting the vessel insert and releasing the contents of the vessel insert into the body portion of the vessel.

5. The apparatus of claim 1, wherein the vessel insert comprises a tubular body having a constant diameter extending into the neck portion of the vessel and the rod has an elastomeric seal at each end that is adapted to seal the tubular bodied vessel insert, wherein advancing the rod distally within the tubular vessel insert disrupts the sealing element thereby releasing the contents of the vessel insert into the body portion of the vessel.

6. The apparatus of claim 1, wherein the pierceable aperture of the cap element is a resealable septum portion and is adapted to seal the vessel and secure the vessel insert in the vessel.

7. The apparatus of claim 1, wherein a proximal end of the vessel insert comprises an annular ring and the sealing element, wherein the cap element comprises a deformable flange with an internal opening, the deformable flange being adapted to secure the vessel insert in the vessel when the annular ring is located adjacent to the internal opening, and wherein disrupting the sealing element also advances the annular ring through the deformable flange thereby releasing the contents of the vessel insert into the body portion of the vessel wherein the deformable flange is elastomeric, and wherein a distal surface of the deformable flange is angled to seal the vessel upon reducing the a pressure in the vessel insert to less than atmospheric pressure.

8. The apparatus of claim 2, wherein the vessel insert defines an internal chamber within the neck portion of the vessel for receiving the reagent, the internal chamber having a floor with a raised central portion extending proximally from the floor to a proximal portion comprising the at least one sealing element thereby defining a tube, wherein disrupting the at least one sealing element allows the release of the contents of the vessel insert into the body portion of the vessel and wherein a portion of the floor is thinner than a remainder of the vessel insert, and wherein disrupting the at least one sealing element and causes the raised central portion to break off and separate from the vessel insert.

9. The apparatus of claim 1, wherein a proximal end of the vessel insert comprises at least one opening and the at least one sealing element, the at least one sealing element being adapted to seal a body portion of the vessel insert, the opening allowing for fluid communication with the body portion of the vessel wherein sample is introduced into the body portion of the vessel through the opening, wherein the cap element comprises a cap and a septum, the cap being adapted to secure the vessel insert and the septum to the proximal end of the vessel, and wherein disrupting the at least one sealing element places the vessel insert in fluid communication with the body portion of the vessel and wherein the at least one opening is located between the proximal end of the vessel and the at least one sealing element.

10. The apparatus of claim 1, wherein the vessel insert has a head portion and a body portion, the head portion having a surface sized to rest upon a proximal end of the vessel to support the vessel insert in the vessel, the at least one sealing element located distally from the proximal end of the vessel, wherein the cap element comprises a cap and a septum, the cap being adapted to secure the vessel insert and the septum to the proximal end of the vessel, and wherein disrupting the at least one sealing element releases the contents of the vessel insert into the body portion of the vessel.

11. The apparatus of claim 1, wherein the biological sample is a sterile body fluid and the sterile body fluid is introduced into the vessel by a sample delivery device comprising a cannula within a needle through which the sterile body fluid flows from the sample delivery device.

12. The apparatus of claim 3, wherein the at least one sealing element is made of at least one thin material selected from a group consisting of foil, glass, molded polymer, and a combination thereof.

13. The apparatus of claim 12, wherein the at least one sealing element is a membrane having a sealed interior cavity filled with carbon, glass or at least one reagent.

14. The apparatus of claim 13, wherein the at least one reagent is selected from the group consisting of adsorption resin, culture medium, lytic reagent, and a combination thereof.

15. A method of operating the apparatus of claim 1, comprising the steps of:
   obtaining the apparatus of claim 1 and
   introducing the biological sample into the vessel through the cap element;
   wherein after introduction of the biological sample, the rod is operated so as to disrupt a portion of the vessel insert and release of the contents of the vessel insert into the body portion of the vessel containing the culture media thereby combining the at least one reagent, the biological sample and the culture media in the vessel.

16. The apparatus of claim 8, wherein the internal chamber of the vessel insert contains the at least one reagent; and the body portion of the vessel contains a culture media; wherein when a force is applied to the proximal sealing element so as to disrupt the proximal sealing element thereby disrupting the vessel insert; and wherein, after the vessel insert is disrupted, the vessel is tilted to release the contents of the internal chamber into the body portion of the vessel.

17. The apparatus of claim 1, wherein the vessel insert comprises a tubular body and a stopper secured to the tubular body by a vacuum force, wherein the tubular body of the vessel insert contains the at least one reagent and a pressure in the vessel insert is less than atmospheric pressure; and further wherein after the biological sample is introduced into the vessel insert through the cap, the rod disrupts the seal and vacuum force so as to detach the stopper and release the contents of the vessel insert into the body portion of the vessel.

* * * * *